United States Patent
Halazy et al.

(10) Patent No.: US 8,053,436 B1
(45) Date of Patent: Nov. 8, 2011

(54) 9-(PIPERAZINYLALKYL) CARBAZOLES AS BAX-MODULATORS

(75) Inventors: Serge Halazy, Vetraz-Monthoux (FR); Dennis Church, Commugny (CH); Bruno Antonsson, Billiat (FR); Agnes Bombrun, Monnetier-Mornex (FR); Patrick Gerber, Villars-Sous-Yens (CH); Jean-Claude Martinou, Versonnex (FR)

(73) Assignee: Merck Serono SA, Coinsins (CH)

( * ) Notice: Subject to any disclaimer, the term of this patent is extended or adjusted under 35 U.S.C. 154(b) by 1297 days.

(21) Appl. No.: 10/110,199

(22) PCT Filed: Oct. 18, 2000

(86) PCT No.: PCT/IB00/01497
§ 371 (c)(1),
(2), (4) Date: Aug. 15, 2002

(87) PCT Pub. No.: WO01/29028
PCT Pub. Date: Apr. 26, 2001

(30) Foreign Application Priority Data

Oct. 18, 1999  (EP) .................................. 99810944

(51) Int. Cl.
*A61K 31/497* (2006.01)
*C07D 403/06* (2006.01)
*C07D 413/14* (2006.01)

(52) U.S. Cl. .............. 514/253.09; 514/254.08; 544/364; 544/369; 544/372

(58) Field of Classification Search .................. 544/364, 544/369, 372; 514/253.09, 254.08
See application file for complete search history.

(56) References Cited

U.S. PATENT DOCUMENTS

| 4,379,160 A | 4/1983 | Harfenist et al. |
| 5,958,919 A | 9/1999 | Olney et al. |

FOREIGN PATENT DOCUMENTS

| FR | 1 167 510 | 11/1958 |
| JP | 3-251564 | * 11/1991 |
| JP | 6-228095 | * 8/1994 |
| SO | 787352 | 11/1978 |
| SU | 1 584 341 | 3/1995 |
| WO | 96 06863 | 3/1996 |
| WO | 97 01635 | 1/1997 |
| WO | 97/14865 | 4/1997 |
| WO | 97 26881 | 7/1997 |

OTHER PUBLICATIONS

Hromatka et al., Mh. Chem., 92, 1242 (1961).*

Michael D. Jacobson: "Apoptosis: Bcl-2-related proteins get connected" Current Biology, 7:R277-R281 1997.
Guido Kroemer: "The proto-oncogene Bcl-2 and its role in regulating apoptosis" Nature Medicine, vol. 3, No. 6, pp. 614-620 Jun. 1997.
John C. Reed: "Double identity for proteins of the Bcl-2 family" Nature, vol. 387, pp. 773-776 Jun. 19, 1997.
Ameeta Kelekar et al.: "Bcl-2-family proteins: the role of the BH3 domain in apoptosis" Trends in Cell Biology, vol. 8, pp. 324-330 Aug. 1998.
Isabelle Martinou et al.: "Viral proteins E1B19K and p35 protect sympathetic neurons from cell death induced by NGF deprivation" The Journal of Cell Biology, vol. 128, No. 1-2, pp. 201-208 Jan. 1995.
Thomas L. Deckwerth, et al.: "BAX is required for nuronal death after trophic factor deprivation and during development" Neuron, vol. 17, pp. 401-411 Sep. 1996.
Gloria I. Perez et al.: "Prolongation of ovarian lifespan into advanced chronological age by Bax-deficiency" Nature Genetics, vol. 21, pp. 200-103 Feb. 1999.
N.A. Komissarenko et al.: "Synthesis of 1-lw-(benzhydrypiperazin-1-yl)alkyl[indoles, 9-[3-(4-benzhydrylpiperazin-1-yl)propyl)carbazole and its derivatives and their antiallergic activity" Khim. Farm. Zh., vol. 24, No. 10, pp. 54-56 1990.
Tetsuto Tsunoda et al.: "Mitsunobu-type alkylation with active methine compounds" Tetrahedron Letters, vol. 37, No. 14, pp. 2459-2462 1996.
Domenico Albanese et al.: "Chemoselective N-alkylation of 2-hydroxycarbazole as a model for the synthesis of N-substituted pyrrole derivatives containing acidic functions" Tetrahedron Letters, vol. 51, No. 19, pp. 5681-5688 1995.
Keith Smith et al.: "A new method for bromination of carbazoles, B-carbolines and iminodibenzyls by use of N-bromosuccinimide and silica gel" Tetrahedron Letters, vol. 48, No. 36, pp. 7479-7488 1992.
T. Ross Kelly et al: "Structure revision of the APHEs through synthesis" Tetrahedron Letters, vol. 40, pp. 1857-1860 1999.
D.A. Patrick et al.: "Anti-pneumocystis carinii pneumonia activity of dicationic carbazoles" Eur. J. Med. Chem, vol. 32, pp. 781-793 1997.
Koert Gerzon et al.: "Structure-activity relationship of some diamine, bis-epoxIdes in mouse leukaemia" Journal of Medicinal and Pharmaceutical Chemistry, vol. 1, No. 3, pp. 223-243, 1959.
Solange Desagher et al.: "Bid-induced conformational change of Bas is responsible for miotchondrial cytochrome c release during apoptosis" The Journal of Cell Biology, vol. 144, No. 5, pp. 891-901 Mar. 8, 1999.
Robert E. King, phD., Pharmaceutical Preparations and Their Manufacture, Remington's Pharmaceutical Sciences 17th Edition, Part 8, pp. 1409-1677.

* cited by examiner

*Primary Examiner* — Rebecca Anderson
(74) *Attorney, Agent, or Firm* — Oblon, Spivak, McClelland, Maier & Neustadt, L.L.P.

(57) ABSTRACT

The present invention is related to piperazine derivatives of carbazole of formula (I) notably for use as pharmaceutically active compounds, as well as to pharmaceutical formulations containing such piperazine derivatives of carbazole. Said piperazine derivatives of carbazole are efficient modulators, in particular efficient inhibitors, of the Bax function and/or activation. The present invention is furthermore related to novel piperazine derivatives of carbazole as well as methods of their preparation.

20 Claims, No Drawings

9-(PIPERAZINYLALKYL) CARBAZOLES AS BAX-MODULATORS

CROSS-REFERENCE TO RELATED APPLICATIONS

This application is a 371 of PCT/IB00/01497 filed Oct. 18, 2000.

FIELD OF THE INVENTION

The present invention is related to piperazine derivatives of carbazole notably for use as pharmaceutically active compounds, as well as pharmaceutical formulations containing such piperazine derivatives of carbazole useful for the treatment of disorders associated with apoptosis, including neurodegenerative disorders, diseases associated with polyglutamine tracts, epilepsy, ischemia, infertility, cardiovascular disorders, renal hypoxia, hepatitis and AIDS. Said piperazine derivatives of carbazole display a modulatory and most notably an inhibitory activity of the cellular death agonist Bax and the activation pathways leading to Bax and allows therefore to block the release of cytochrome c. The present invention is furthermore related to novel piperazine derivatives of carbazole as well as to methods of their preparation.

BACKGROUND OF THE INVENTION

Apoptosis denotes the complex contortions of the membrane and organelles of a cell as it undergoes the process of programmed cell death. During said process, the cell activates an intrinsic suicide program and systematically destroys itself in a controlled manner or by a self-regulated process. The following series of events can be observed:

The cell surface begins to bleb and expresses pro-phagocytic signals. The whole apoptotic cell then fragments into membrane-bound vesicles that are rapidly and neatly disposed of by phagocytosis, so that there is minimal damage to the surrounding tissue.

The cell then separates from its neighbors.

The nucleus also goes through a characteristic pattern of morphological changes as it commits genetic suicide. The chromatin condenses and is specifically cleaved to fragments of DNA.

Neuronal cell death plays an important role in ensuring that the nervous system develops normally. It appears that the death of developing neurons depends on the size of the target that they innervate: cells with fewer synaptic partners are more likely to die than those that have formed multiple synapses. This may reflect a process, which balances the relative number of pre- to postsynaptic neurons in the developing nervous system. Although neuronal cell death is assumed to be apoptotic, it is only recently that neurons in developing rodent brain were conclusively shown to undergo apoptosis as classified by morphology and DNA fragmentation.

Neuronal death occurs via either apoptotic or necrotic processes following traumatic nerve injury or during neurodegenerative diseases. Multiple components are emerging as key players having a role in driving neuronal programmed cell death. Amongst the components leading to neuronal apoptosis are protein members belonging to the Bcl-2 family (see Jacobson, M. D. 1997. *Current Biology* 7:R 277-R281; Kroemer, G. C. 1997. *Nature Medicine:* 614-620; Reed, J. C. 1997. *Nature* 387:773-776).

Bcl-2 is a 26 kDa protein that localizes to the mitochondrial, endoplasmatic reticulum and perinuclear membranes. It is known by a person skilled in the art that the entire Bcl-2 family comprises both anti-apoptotic (Bcl-2, Bcl-$x_L$, Bcl-w, Mcl-1, A1, NR-13, BHRF1, LMW5-HL, ORF16, KS-Bcl-2, E1B-19K, CED-9) and pro-apoptotic (Bax, Bak, Bok, Bik, Blk, Hrk, BNIP3, Bim$_L$, Bad, Bid, EGL-1) molecules (see Kelekar, A., and C. B. Thompson 1998. *Trends in Cell Biology* 8:324-330). Said proteins can form homo- and heterodimers that involve amino acid sequences known as Bcl-2 homology (BH) domains. So far, four of said domains (BH1 to 4) have been identified, the BH3 having been attributed a particularly prominent role in view of the death-promoting cascade. Said BH3 domain of the pro-apoptotic members appears to be required for the interaction between anti and pro-apoptotic molecules. The principal site of action of some of the Bcl-2 family members seems to be the mitochondria. Mitochondria have been shown to play a major role in many types of apoptosis. In particular, this organelle has been shown to release Apoptosis Inducing Factor and cytochrome c, a hemoprotein which is bound to the outer surface of the inner mitochondrial membrane. Said cytochrome c has been shown to trigger caspase 9 activation through Apaf-1/caspase 9 complex formation. Bcl-2 family members play a key role in regulating cytochrome c release. While Bcl-2 and Bcl-$x_L$ have been shown to suppress cytochrome c release, Bax has been found to stimulate this event both in vitro using isolated mitochondria as well as in intact cells following heterologous expression (Martinou et al.; 1995 *The Journal of Cell Biology,* 128, 201-208). The mechanisms by which these proteins perform their function are currently unknown. The three-dimensional structure of Bcl-xL and Bid revealed structural similarities between these proteins and the channel-forming domains of the bacterial toxins colicins and diphtheria toxins. Consistent with such structural similarity, some members of this family including Bax were also found able to form ion channels in synthetic lipid membranes. The channel forming activity of these proteins has not yet been demonstrated in vivo.

Studies performed with Bax-deficient mice led to the conclusion that Bax plays a prominent role within the apoptosis pathways, notably in neuronal apoptosis. Bax is viewed to be essential for apoptosis induced by NGF deprivation in neonatal sympathetic neurons or for apoptosis induced in cerebellar granule cells by potassium deprivation from the culture medium. Moreover, it was found that in the Bax-deficient mice (knock-out) neonatal moto-neurons from the facial nucleus can survive following axotomy (see Deckwerth, T. L., Elliott J. L., Knudson C. M. et al. 1996. *Neuron* 17, 401-41). Hence, the inhibition of the Bax activity leading to the prevention of cytochrome c release from mitochondria during apoptosis, is viewed to be useful to protect neurons and also other cell types from various cell death stimuli.

In WO 97/01635 (Neurex Corp.) the inhibition of apoptosis in an effort to promote cell survival is suggested to be achieved by introducing into the cell a chimeric gene containing a polynucleotide encoding a Bax-ω-polypeptide being operably linked to a promoter effective to cause transcription of the polynucleotide in the cell. It is reported that the expression of the Bax-ω-polypeptide is effective to inhibit apoptosis in the cell.

WO 96/06863 claims agents for inducing apoptosis, notably for cancer therapy. Such agents interact with extracellular or cell surface membrane bound opiod-like molecules or their receptors. Such agents may be coupled to peptides which assist in the transport of the agents through the cell membrane to promote internalisation and accumulation in the cell nucleus if this is the site at which the agent produces apoptosis.

Perez et al. in *Nat. Genet.* 1999, 21(2), 200-203 have indicated that apoptosis plays a fundamental role in follicular atresia and they suggest to selectively disrupt the Bax function in order to extend the ovarian lifespan.

Bax inhibition could indeed represent an interesting therapy for all diseases associated with apoptosis, including neurodegenerative diseases (e.g. Alzheimer's disease, Parkinson's disease, diseases associated with polyglutamine tracts including Huntington's disease, spinocerebellar ataxias and dentatorubral-pallidoluysian atrophy; amyotrophic lateral sclerosis, retinitis pigmentosa and multiple sclerosis, epilepsy), ischemia (stroke, myocardial infarction and reperfusion injury), infertility (like pre-mature menopause, ovarian failure or follicular atresia), cardiovascular disorders (arteriosclerosis, heart failure and heart transplantation), renal hypoxia, hepatitis and AIDS.

Hence, it is an objective of the present invention to provide compounds enabling the treatment of a whole variety of apoptosis-related disorders, including notably the above mentioned diseases.

It is specifically an objective of the present invention to provide a treatment of apoptosis related disorders by specifically modulating, e.g. by inhibiting, the Bax function or by inhibiting the Bax activation.

It is notably an objective of the present invention to provide relatively small molecule pharmaceuticals, more specifically non-proteinaceous molecules that avoid essentially all of the drawbacks arising from the use of large bio-peptides or bio-proteins (e.g. their restricted bio-availability as well as problems arising from possible in vivo intolerance), however, which are suitable for the treatment of diseases associated with abnormal apoptosis. It is particularly an objective of the present invention to provide relatively small molecule chemical compounds which are suitable Bax modulators (e.g. compounds inhibiting the Bax function or inhibiting the Bax activation) so to be available for a convenient method of treating diseases involving abnormal apoptosis. Moreover, it is an objective of the present invention to provide methods for preparing said small molecule chemical compounds. It is furthermore an objective of the present invention to provide new pharmaceutical formulations for the treatment of diseases which are caused by abnormal apoptosis, more specifically by Bax. It is finally an objective of the present invention to provide a method of treating diseases that are caused by abnormal apoptosis.

DESCRIPTION OF THE INVENTION

The aforementioned objectives have been met according to the independent claims which are set out hereinafter in the description. Preferred embodiments are set out within the dependent claims.

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetra-hydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"Alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"Alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"Acyl" refers to the group —C(O)R where R includes "$C_1$-$C_6$-alkyl", "aryl", "heteroaryl", "$C_1$-$C_6$-alkyl aryl" or "$C_1$-$C_6$-alkyl heteroaryl".

"Acyloxy" refers to the group —OC(O)R where R includes "$C_1$-$C_6$-alkyl", "aryl", "hetero-aryl", "$C_1$-$C_6$-alkyl aryl" or "$C_1$-$C_6$-alkyl heteroaryl".

"Alkoxy" refers to the group —O—R where R includes "$C_1$-$C_6$-alkyl" or "aryl" or "hetero-aryl" or "$C_1$-$C_6$-alkyl aryl" or "$C_1$-$C_6$-alkyl heteroaryl". Preferred alkoxy groups include by way of example, methoxy, ethoxy, propoxy, butoxy, phenoxy and the like.

"Alkoxycarbonyl" refers to the group —C(O)OR where R includes "$C_1$-$C_6$-alkyl" or "aryl" or "heteroaryl" or "$C_1$-$C_6$-alkyl aryl" or "$C_1$-$C_6$-alkyl heteroaryl".

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl heteroaryl".

"Acylamino" refers to the group —NR(CO)R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"Halogen" refers to fluoro, chloro, bromo and iodo atoms.

"Sulfonyl" refers to group "—$SO_2$—R" wherein R is selected from H, "aryl", "heteroaryl", "$C_1$-$C_6$-alkyl", "$C_1$-$C_6$-alkyl" substituted with halogens e.g. an —$SO_2$—$CF_3$ group, "$C_1$-$C_6$-alkyl aryl" or "$C_1$-$C_6$-alkyl heteroaryl".

"Sulfoxy" refers to a group "—S(O)—R" wherein R is selected from H, "$C_1$-$C_6$-alkyl", "$C_1$-$C_6$-alkyl" substituted with halogens e.g. an —SO—$CF_3$ group, "aryl", "heteroaryl", "$C_1$-$C_6$-alkyl aryl" or "$C_1$-$C_6$-alkyl heteroaryl".

"Thioalkoxy" refers to groups —S—R where R includes "$C_1$-$C_6$-alkyl" or "aryl" or "hetero-aryl" or "$C_1$-$C_6$-alkyl aryl" or "$C_1$-$C_6$-alkyl heteroaryl". Preferred thioalkoxy groups include thiomethoxy, thioethoxy, and the like.

"Substituted or unsubstituted": Unless otherwise constrained by the definition of the individual substituent, the above set out groups, like "alkyl", "alkenyl", "alkynyl", "aryl" and "heteroaryl" etc. groups may optionally be substituted with from 1 to 5 substituents selected from the group consisting of "$C_1$-$C_6$-alkyl", "$C_1$-$C_6$-alkyl aryl", "$C_1$-$C_6$-alkyl heteroaryl", "$C_2$-$C_6$-alkenyl", "$C_2$-$C_6$-alkynyl", primary, secondary or tertiary amino groups or quarter-nary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Alternatively, said substitution could also comprise situations where neighboring substituents have undergone ring closure, notably when viccinal functional substituents are involved, thus forming e.g. lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of formula I that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, trifluoroacetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and polygalacturonic acid. Said compounds can also be administered as pharmaceutically acceptable quaternary salts known by a person skilled in the art, which specifically include the quarternary ammonium salt of the formula —NR,R',R"$^+$Z$^-$, wherein R, R', R" is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by an essentially enantiomeric synthesis or a synthesis comprising an enantioselective step, whereby a surplus of one enantiomer in the order of at least about 52% ee is yielded. In the absence of an enantiomeric synthesis, racemic products are usually obtained that do however also have the inventive set out activity as Bax inhibitors.

Quite surprisingly, it was now found that the piperazine derivatives of carbazole according to formula I are suitable pharmaceutically active agents, notably by effectively modulating the Bax function or the Bax activation.

Compounds of formula I according to the present invention are those wherein $R^0$ and $R^1$ are selected independently from each other from substituents including or consisting of hydrogen, halogen, cyano, sulfonyl, sulfoxy, substituted or unsubstituted $C_1$-$C_6$-thioalkoxy, nitro, primary, secondary or tertiary amine or sulfonamide, aminocarbonyl, aminothiocarbonyl, hydroxy, substituted or unsubstituted $C_1$-$C_6$-alkoxy, aryloxy, heteroaryloxy, carboxylic amide, alkoxycarbonyl, carboxylic ester, carboxylic acid, substituted or unsubstituted $C_1$-$C_6$-alkyl carbonyl, substituted or unsubstituted arylcarbonyl or hetero-arylcarbonyl, substituted or unsubstituted saturated or unsaturated $C_3$-$C_8$-cycloalkylcarbonyl, substituted or unsubstituted $C_1$-$C_6$-alkyl, substituted or unsubstituted $C_2$-$C_6$-alkenyl, substituted or unsubstituted $C_2$-$C_6$-alkynyl, substituted or unsubstituted aryl or heteroaryl, substituted or unsubstituted 3-8 membered saturated or unsaturated cyclic alkyl.

$R^2$ is selected from the group comprising or consisting of hydrogen, substituted or unsubstituted $C_1$-$C_6$-alkyl, substituted or unsubstituted $C_2$-$C_6$-alkenyl, substituted or unsubstituted $C_2$-$C_6$-alkynyl, substituted or unsubstituted aryl or heteroaryl, substituted or unsubstituted 3-8 membered saturated and unsaturated cyclic alkyl, sulfoxy, sulfonyl, sulfonamide, carboxylic amide, aminocarbonyl, alkoxycarbonyl, hydrazine acyl, substituted or unsubstituted carbonyl-$C_1$-$C_6$-alkyl, substituted or unsubstituted arylcarbonyl or heteroarylcarbonyl, substituted or unsubstituted saturated or unsaturated $C_3$-$C_8$-cycloalkylcarbonyl, alkoxy, $C_1$-$C_6$-thioalkoxy.

$R^3$ is selected from the group comprising or consisting of hydrogen, halogen, substituted or unsubstituted $C_1$-$C_6$-alkyl, substituted or unsubstituted $C_2$-$C_6$-alkenyl, substituted or unsubstituted $C_2$-$C_6$-alkynyl, substituted or unsubstituted aryl or heteroaryl, substituted or unsubstituted 3-8 membered saturated and unsaturated cyclic alkyl, alkoxycarbonyl, carboxylic amide, $C_1$-$C_6$-alkoxy, substituted or unsubstituted aryloxy, substituted or unsubstituted hetero-aryloxy, hydroxy, substituted or unsubstituted $C_1$-$C_6$-alkyl carbonyl, substituted or unsubstituted arylcarbonyl or heteroarylcarbonyl, substituted or unsubstituted saturated or unsaturated $C_4$-$C_8$-cycloalkylcarbonyl, or $R^3$ could be an oxo (=O) group.

k and l are independently from each other an integer from 0 to 4, preferably they are both independently from each other between 0 and 2 and most preferred either 0 or 1.

X is a substituted methylene group, i.e. a group of the formula —(CR'R")—, whereby at least one of R' and/or R" is not hydrogen but a substituent containing at least one heteroatom. Thus, R' and/or R" is selected from the group comprising or consisting of a substituted $C_1$-$C_6$-alkyl, an unsubstituted or substituted aryl or heteroaryl, a substituted or unsubstituted $C_1$-$C_6$-alkoxy, substituted or unsubstituted $C_2$-$C_6$-alkenyl, substituted or unsubstituted $C_2$-$C_6$-alkynyl, a primary, secondary or tertiary amino, a quaternary ammonium salt of the formula —NR,R',R"$^+$Z$^-$, wherein R, R', R" is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate); or R' and/or R" could be an acylamino, amino-carbonyl, $C_1$-$C_6$-alkoxycarbonyl, a carboxylic ester acid or amide, halogen, hydroxy, sulfonyl, sulfonamide, $C_1$-$C_6$-thioalkyl, $C_1$-$C_6$-thioalkoxy or X could be a C=O or a C=S group.

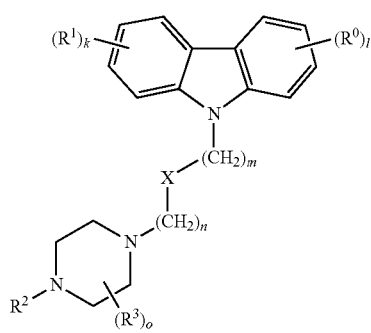

I m and n are independently from each other an integer from 1 to 3, preferably both m and n are 1. o is an integer from 0 to 8. Preferably o is an integer from 0 to 2, most preferred is o=0 or 2.

Specifically, $R^0$ and $R^1$ of formula I are selected independently from each other of the group comprising or consisting of hydrogen, halogen, cyano, substituted or unsubstituted and $C_1$-$C_6$-alkyl, substituted or unsubstituted 3-8 membered saturated or unsaturated cyclic alkyl, C(=O)ORa, C(=O)NRaRb, C(=O)NRaRc, C(=O)Ra, C(=O)Rc, CRa(=N—N-Rb), CRa(=N—N-Rc), CRa(=N—O-Rb), $C_1$-$C_6$-alkylene, trifluoromethyl, trifluoromethoxy, ORa, ORc, NRaRb, NRaRc, NRaC(=O)NRaRb, NRaC(=O)NRaRc, NRaC(=O)Rb, SRa, SRc, NRaC(=O)Rc, OC(=O)Ra, OC(=O)Rc, NRa(SO$_2$Rb), NRa(SO$_2$Rc), SO$_2$NRaRb, SO$_2$NRaRc, NO$_2$, CH$_2$NRaRb, CH$_2$NRaRc, CH$_2$NRaC(=O)NRaRb, CH$_2$NRaC(=O)NRaRc, CH$_2$NRaC(=O)Rb, CH$_2$NRaC(=O)Rc, CH$_2$NRa(SO$_2$Rb), CH$_2$NRa(SO$_2$Rc), OSO$_2$-trifluoromethyl.

Alternatively, $R^0$ and $R^1$ according to formula I could also be independently from each other selected from an aryl or a 5-6-membered heterocyclic group containing at least one hetero atom selected from oxygen, nitrogen and sulfur, being optionally substituted by at least one $C_1$-$C_6$-alkyl, C(=O)ORa, $C_1$-$C_6$-alkylene, trifluoromethyl, trifluoromethoxy, ORa, OC(=O)Ra, OC(=O)Rc, NRaRb, CH$_2$—NRaRb, SRa, SRc, NO$_2$, cyano, halogen, SO$_2$NRaRb, SO$_2$NRaRc, NRaSO$_2$Ra, NRaSO$_2$Rc, $C_1$-$C_4$-alkylene C(=O)ORa, OSO$_2$-trifluoromethyl.

According to a further preferred embodiment $R^2$ within formula I is selected from the group comprising or consisting of hydrogen, substituted or unsubstituted $C_1$-$C_6$-alkyl, substituted or unsubstituted 3-8 membered saturated cyclic alkyl, C(=O)ORa, C(=O)NRaRb, C(=O)NRaRc, C(=O)Ra, C(=O)Rc, CRa(=N—N-Rb), CRa(=N—N-Rc), CRa(=N—O-Rb), $C_1$-$C_6$-alkylene, trifluoromethyl, trifluoromethoxy, RaC(=O)NRaRc, RaC(=O)Rb, RaC(=O)Rc, Ra(SO$_2$Rb), Ra(SO$_2$Rc), SO$_2$NRaRb, SO$_2$NRaRc, CH$_2$NRaRb, CH$_2$NRaRc, CH$_2$NRaC(=O)NRaRb, CH$_2$NRaC(=O)NRaRc, CH$_2$NRaC(=O)Rb, CH$_2$NRaC(=O)Rc, CH$_2$NRa(SO$_2$Rb), CH$_2$NRa(SO$_2$Rc), OSO$_2$-trifluoromethyl.

Alternatively, $R^2$ within formula I could also be independently from each other selected from $C_1$-$C_6$-alkylaryl, $C_1$-$C_6$-alkylheteroaryl, an aryl or a 5-6-membered heterocyclic group containing at least one hetero atom selected from oxygen, nitrogen and sulfur, both the aryl, heterocyclic group being optionally substituted by at least one $C_1$-$C_6$-alkyl, C(=O)ORa, $C_1$-$C_6$-alkylene, trifluoromethyl, trifluoromethoxy, ORa, OC(=O)Ra, OC(=O)Rc, NRaRb, CH$_2$—NRaRb, NO$_2$, cyano, halogen, SO$_2$NRaRb, SO$_2$NRaRc, NRaSO$_2$Ra, NRaSO$_2$Rc, $C_1$-$C_6$-allyleneC(=O)ORa, OSO$_2$-trifluoromethyl.

According to a further preferred embodiment $R^3$ of formula I is selected from the group comprising or consisting of hydrogen, $C_1$-$C_6$-alkyl, ORa, ORc, C(=O)ORa, C(=O)ORc C(=O)NRaRb, C(=O)NRaRc, C(=O)Ra, C(=O)Rc, RaC(=O)NRaRc, RaC(=O)Rb, RaC(=O)Rc, Ra(SO$_2$Rb), Ra(SO$_2$Rc), or a (=O) group (oxo).

Alternatively, $R^3$ of formula I could also be independently from each other selected from an aryl or a 5-6-membered heterocyclic group containing at least one heteroatom selected from oxygen, nitrogen and sulfur, both the aryl, heterocyclic group being optionally substituted by at least one $C_1$-$C_6$-alkyl, C(=O)ORa, C(=O)ORc, $C_1$-$C_6$-alkylene, trifluoromethyl, trifluoromethoxy, ORa, OC(=O)Ra, OC(=O)Rc, NRaRb, CH$_2$—NRaRb, NO$_2$, cyano, halogen, SO$_2$NRaRb, SO$_2$NRaRc, NRaSO$_2$Ra, NRaSO$_2$Rc, $C_1$-$C_6$-alkyleneC(=O)ORa, OSO$_2$-trifluoromethyl.

In the above set out definitions Ra and Rb are the same or different and they are independently selected from hydrogen and $C_1$-$C_6$-alkyl, being optionally substituted by at least one halogen, a $C_1$-$C_6$-alkoxy or an amino group.

Furthermore, Rc does represent therein an unsubstituted or substituted phenyl, an unsubstituted or substituted benzyl or a 3-8-membered unsubstituted or substituted saturated 3-8-membered cyclic alkyl.

The present invention also includes the geometrical isomers, the optically active forms, enantiomers, diastereomers of compounds according to formula I, as well as their racemates. It also includes the pharmaceutically acceptable salts, e.g. hydrates, acid addition salts there-of, as well as the pharmaceutically active derivatives of the carbazole derivatives of formula I. Preferred pharmaceutically acceptable salts of the compound I, are acid addition salts formed with pharmaceutically acceptable acids like hydrochloride, hydro-bromide, sulfate or bisulfate, phosphate or hydrogen phosphate, acetate, benzoate, succinate, fumarate, maleate, lactate, citrate, tartrate, gluconate, methanesulfonate, benzenesulfonate, trifluoroacetate and para-toluenesulfonate salts.

For the purpose of inhibiting Bax, the piperazine derivatives of carbazole according to the present invention are those compounds of formula I, wherein X is not an unsubstituted alkyl group, but a moiety which contains at least one heteroatom, preferably between 1-6, more preferably 1-3, and most preferred 1 or 2 heteroatoms. Preferred heteroatoms are O, F, Cl, N. The preferred methylene groups include the —CF$_2$-group, the —C=O group or a methylene group —CHR', where R' is selected of halogen, ORa, NRaRb, NHSO$_2$Ra, NHC(=O)NHRa, NHC(=O)ORa, NHC(=O)Ra, OC(=O)Ra, OC(=O)NHRa, OC(=O)Rc, SRa, SRc; or R' represents CF$_3$. Most preferred are compounds according to formula I, wherein X is —CHF or —CHOH.

According to a preferred embodiment the substituent $R^2$ of formula I is $C_1$-$C_6$-alkylaryl (e.g. benzyl), $C_1$-$C_6$-alkylheteroaryl containing at least one heteroatom selected from oxygen, nitrogen and sulfur, said aryl or heteroaryl or heterocyclic group being optionally substituted by at least one $C_1$-$C_6$-alkyl, C(=O)ORa, $C_1$-$C_4$-alkylene, trifluoromethyl, trifluoromethoxy, ORa, ORc, SRa, SRc, OC(=O)Ra, OC(=O)Rc, NRaRb, CH$_2$—NRaRb, NO$_2$, cyano, halogen, SO$_2$NRaRb, SO$_2$NRaRc, NRaSO$_2$Ra, NRaSO$_2$Rc, $C_1$-$C_4$-alkylene, C(=O)ORa, OSO$_2$-trifluoromethyl.

According to a further particularly preferred embodiment, $R^2$ is H, benzyl or heterocyclic group.

A still further preferred embodiment consists in those piperazine derivatives of carbazole of formula I that are suitable as a pharmacological tool. For such compounds of formula I, $R^2$ is a fluorescent moiety. Preferred fluorescent moieties $R^2$ include (4,4-difluoro-1,3,5,7-tetramethyl-4-bora-3a,4a-diaza-s-indacene-2-yl)acetamide, [(4,4-difluoro-5,7-dimethyl-4-bona-3a,4a-diaza-s-indacene-3-yl)methyl]acetamide, (4,4-difluoro-1,3,5,7-tetramethyl-4-bora-3a,4a-diazas-indacen-8-yl)methyl, 2-(6-hydroxy-3-oxo-3H-xanthen-9-yl)-4-(aminoacetyl)benzoic acid, (6,7-dimethoxy-2H-chromen-2-one)-4-methyl, 4,4-difluoro-1,3,5,7-tetramethyl-4-bora-3a,4a-diaza-s-indacene-8-propionyl, 4-nitro-(2,1,3-benzoxadiazol)-7-yl.

The fluorescent labelled compounds may be used to study interactions with target proteins, cell permeability and the intracelleular localisation. This is useful for understanding the mode of action of the Bax inhibiting compounds.

For the purpose of inhibiting Bax, particularly potent carbazole derivatives according to formula I are those wherein R⁰ and R¹ represent hydrogen or lipophilic substituents, including notably, bromine, chlorine, aryl, or $C_1$-$C_6$-alkyl, preferably methyl.

The piperazine moiety within formula I could basically be substituted with up to 8 residues (up to 8 substituents R³), but according to a preferred embodiment R³ is hydrogen or a $C_1$-$C_6$-alkyl and most preferred is R³=hydrogen so that said piperazine moiety is attached to the central alkyl group by its position 1 nitrogen whereas the para nitrogen (position 4) is optionally substituted by the further group R².

The most preferred Bax inhibitors according to the present invention are those carbazole derivatives of formula I, wherein X is a —CF₂-group, a —C═O group, CH—OH, CH—F, or a methylene group —CHR' where R' is selected of, alkoxy, amino or amide, R⁰ and R¹ represent hydrogen or lipophilic substituents, including notably, bromine, chlorine, aryl, or $C_1$-$C_6$-alkyl, preferably methyl, n and m are both 1, while o is 0 and R² is H or benzyl.

Specific examples of compounds of formula I include the following:

(±)-1-(4-Benzyl-piperazin-1-yl)-3-(2-methyl-carbazol-9-yl)-propan-2-ol
(±)-4-(3-Carbazol-9-yl-2-hydroxy-propyl)-piperazine-1-carboxylic tert-butyl ester
(±)-1-Carbazol-9-yl-3-piperazin-1-yl-propan-2-ol
(±)-4-[3-(3,6-Dibromocarbazol-9-yl)-2-hydroxy-propyl]-piperazine-1-carboxylic tert-butyl ester
(±)-1-(3,6-Dibromocarbazol-9-yl)-3-piperazin-1-yl-propan-2-ol
(±)-1-(4-Benzyl-piperazin-1-yl)-3-(3,6-dibromo-carbazol-9-yl)-propan-2-ol
(±)-1-(4-Benzyl-piperazin-1-yl)-3-carbazol-9-yl-propan-2-ol
(±)-4-[3-(3-Bromo-carbazol-9-yl)-2-hydroxy-propyl]-piperazine-1-carboxylic tert-butyl ester
(±)-1-(3-Bromocarbazol-9-yl)-3-piperazin-1-yl-propan-2-ol
(±)-1-(4-Benzyl-piperazin-1-yl)-3-(2-hydroxy-carbazol-9-yl)-propan-2-ol
(S)-4-[3-(3,6-Dibromocarbazol-9-yl)-2-hydroxy-propyl]-piperazine-1-carboxylic tert-butyl ester
(R)-4-[3-(3,6-Dibromocarbazol-9-yl)-2-hydroxy-propyl]-piperazine-1-carboxylic tert-butyl ester
(S)-4-[3-(3-Bromo-carbazol-9-yl)-2-hydroxy-propyl]-piperazine-1-carboxylic tert-butyl ester
(R)-4-[3-(3-Bromo-carbazol-9-yl)-2-hydroxy-propyl]-piperazine-1-carboxylic tert-butyl ester
(S)-1-(3,6-Dibromocarbazol-9-yl)-3-piperazin-1-yl-propan-2-ol
(R)-1-(3,6-Dibromocarbazol-9-yl)-3-piperazin-1-yl-propan-2-ol
(S)-1-(3-Bromocarbazol-9-yl)-3-piperazin-1-yl-propan-2-ol
(R)-1-(3-Bromocarbazol-9-yl)-3-piperazin-1-yl-propan-2-ol
(±)-1-[(3,4-Dichloro-phenyl)-piperazin-1-yl]-3-(2-methyl-carbazol-9-yl)-propan-2-ol
(±)-1-[(3,4-Dichloro-phenyl)-piperazin-1-yl]-3-(carbazol-9-yl)-propan-2-ol
(±)-1-[(4-Benzo[1,3]dioxol-5-yl-methyl)-piperazin-1-yl]-4-carbazol-9-yl)-propan-2-ol
(±)-1-Carbazol-9-yl-3-[4-(4-fluoro-benzyl)-piperazin-1-yl]-propan-2-ol
(±)-1-(3,6-Dibromo-carbazol-9-yl)-3-[4-(4-fluoro-benzyl)-piperazin-1-yl]-propan-2-ol
(±)-1-[4-(4-Fluoro-benzyl)-piperazin-1-yl]-3-(3-phenyl-carbazol-9-yl)-propan-2-ol
(±)-9-(2-Hydroxy-3-piperazin-1-yl-propyl)-carbazole-3,6-dicarbonitrile
(±)-1-(3-Nitrocarbazol-9-yl)-3-piperazin-1-yl-propan-2-ol
(±)-1-(3-Phenylcarbazol-9-yl)-3-piperazin-1-yl-propan-2-ol
(±)-1-(2-Hydroxycarbazol-9-yl)-3-piperazin-1-yl-propan-2-ol
(±)-1-(3,6-Diphenylcarbazol-9-yl)-3-piperazin-1-yl-propan-2-ol
(±)-1-(3,6-Dibromo-carbazol-9-yl)-3-[4-(3-phenyl-propyl)-piperazin-1-yl]-propan-2-ol
(±)-1-Carbazol-9-yl-3-[4-(3-phenyl-propyl)-piperazin-1-yl]-propan-2-ol
(±)-3,6-Dibromo-9-(2-fluoro-3-piperazin-1-yl-propyl)-carbazole
(±)-1-(3-Amino-carbazol-9-yl)-3-piperazin-1-yl-propan-2-ol
(±)-N-[9-(2-Hydroxy-3-piperazin-1-yl-propyl)-carbazol-3-yl]-acetamide
(±)-1-[4-(3-Carbazol-9-yl-2-hydroxy-propyl)-piperazin-1-yl]-2-phenoxy-ethanone
(±)-1-[4-(3-Carbazol-9-yl-2-hydroxy-propyl)-piperazin-1-yl]-1-phenyl-methanone
(±)-1-[4-(3-Carbazol-9-yl-2-hydroxy-propyl)-piperazin-1-yl]-2-(4-hydroxy-phenoxy)-ethanone
(±)-1-[4-(3-Carbazol-9-yl-2-hydroxy-propyl)-piperazin-1-yl]-1-(4-hydroxy-phenyl)-methanone
(±)-1-[4-(3-Carbazol-9-yl-2-hydroxy-propyl)-piperazin-1-yl]-1-(4-fluoro-phenyl)-methanone
(±)-1-(4-Benzenesulfonyl-piperazin-1-yl]-3-carbazol-9-yl-propan-2-ol
(±)-9-[3-(4-Benzyl-piperazin-1-yl)-2-methoxy-propyl]-carbazole
(±)-1-(3,6-Dibromo-carbazol-9-yl)-3-piperazin-1-yl-propan-2-one
(±)-1-(3,6-Dibromo-carbazol-9-yl)-3-[4-(2-hydroxy-3-methylamino-propyl)-piperazin-1-yl]-propan-2-ol
1-(3,6-Dibromo-carbazol-9-yl)-3-[4-(3-phenyl-1,2,4-thiadiazol-5-yl)-piperazin-1-yl]-propan-2-ol
(±)-1-(4-Cyclohexylmethylpiperazin-1-yl)-3-(3,6-dibromo-carbazol-9-yl)-propan-2-ol
(±)-1-[(4-Fluorophenyl)-piperazin-1-yl]-3-(3,6-dibromocarbazol-9-yl)-propan-2-ol
(±)-1-(Carbazol-9-yl)-3-[4-(4-nitrobenzyl)piperazin-1-yl]propan-2-ol
(±)-1-(Carbazol-9-yl)-3-[4-(4-methoxybenzyl)piperazin-1-yl]propan-2-ol
(±)-1-[4-(4-Fluorobenzyl)piperazin-1-yl]-3-{3-[4-(trifluoromethyl)phenyl]-carbazol-9-yl}propan-2-ol
(±)-1-[4-(4-Fluorobenzyl)piperazin-1-yl]-3-{3-[4-(trifluoromethoxy)phenyl]-carbazol-9-yl}propan-2-ol
(±)-1-(Carbazol-9-yl)-3-[4-(3-fluorobenzyl)piperazin-1-yl]propan-2-ol
(±)-1-(Carbazol-9-yl)-3-[4-(thien-2-ylmethyl)piperazin-1-yl]propan-2-ol
(±)-1-(4-Butylpiperazin-1-yl)-(3-carbazol-9-yl)propan-2-ol
(±)-4-({4-[3-carbazol-9-yl)-2-hydroxypropyl]piperazin-1-yl}methyl)phenol
(±)-1-[4-(4-tert-Butylbenzyl)piperazin-1-yl]-3-(carbazol-9-yl)propan-2-ol
(±)-1-(Carbazol-9-yl)-3-[4-(3,4-dichlorobenzyl)piperazin-1-yl]propan-2-ol
(±)-1-(Carbazol-9-yl)-3-{4-[4-(methylsulfonyl)benzyl])piperazin-1-yl}propan-2-ol
(±)-1-(3,6-Dibromocarbazol-9-yl)-3-[4-(thien-2-ylmethyl)piperazin-1-yl]propan-2-ol
(±)-1-(3,6-Dibromocarbazol-9-yl)-3-[4-(thien-3-ylmethyl)piperazin-1-yl]propan-2-ol
(±)-1-(3,6-Dibromocarbazol-9-yl)-3-[4-(pyridin-3-ylmethyl)piperazin-1-yl]propan-2-ol (±)-1-(3,6-Dibromocarbazol-9-yl)-3-[4-(4-methoxybenzl)piperazin-1-yl]propan-2-ol
(±)-1-(3,6-Dibromocarbazol-9-yl)-3-[4-(4-tert-butylbenzyl)piperazin-1-yl]propan-2-ol
(±)-1-(3,6-Dibromocarbazol-9-yl)-3-[4-(4-trifluoromethylbenzyl)piperazin-1-yl]propan-2-ol
(±)-1-[4-(1,3-Benzodioxol-5-ylmethyl)piperazin-1-yl]-3-(3,6-dibromo-carbazol-9-yl)propan-2-ol
(±)-1-(4-Cyclohexylmethylpiperazin-1-yl)-3-(3-phenylcarbazol-9-yl)-propan-2-ol
(±)-3,6-Dibromo-9-{3-[4-(cyclohexylmethyl)piperazin-1-yl]-2-fluoropropyl}-carbazole
(±)-9-{3-[4-(Cyclohexylmethyl)piperazin-1-yl]-2-fluoropropyl}-3-phenyl-carbazole
(±)-4-[3-(3,6-Dibromocarbazol-9-yl)-2-hydroxypropyl]-N-(4-fluorophenyl)piperazine-1-carboxamide
(±)-1-(3,6-Dibromo-carbazol-9-yl)-3-[4-(thien-2-ylsulfonyl)piperazin-1-yl]propan-2-ol
(±)-1-[4-(Benzylsulfonyl)piperazin-1-yl]-3-(3,6-dibromo-carbazol-9-yl)propan-2-ol
(±)-1-(3,6-Dibromo-carbazol-9-yl)-3-[4-(3,4-dichlorobenzyl)piperazin-1-yl]propan-2-ol
(±)-1-(3,6-Dibromo-carbazol-9-yl)-3-[4-(2-morpholin-4-ethyl)piperazin-1-yl]propan-2-ol
(±)-1-[4-(4-Fluorobenzyl)piperazin-1-yl]-3-(3-thien-2-yl-carbazol-9-yl)-propan-2-ol
(±)-1-(3,6-Dibromo-carbazol-9-yl)-3-{4-[3,4-diethoxyphenyl)sulfonyl]piperazin-1-yl}propan-2-ol
(±)-1-[4-(Cyclohexylmethyl)piperazin-1-yl]-3-(3,6-dichloro-carbazol-9-yl)propan-2-ol
(±)-4-[3-(3,6-Dichlorocarbazol-9-yl)-2-hydroxypropyl]-piperazine-1-carboxylic tert-butyl ester
(±)-1-(3,6-Dichlorocarbazol-9-yl)-3-piperazin-1-yl-propan-2-ol
(±)-4-[3-(3,6-Dibromocarbazol-9-yl)-2-oxopropyl]-piperazine-1-carboxylic tert-butyl ester
(±)-3,6-Dibromo-9-(2,2-difluoro-3-piperazin-1-ylpropyl)-carbazole
(±)-4-[3-(3,6-dibromocarbazol-9-yl)-2,2-difluoropropyl]-piperazine-1-carboxylic tert-butyl ester
(±)-1-(3-Bromo-carbazol-9-yl)-3-[4-(2-phenylethyl)piperazin-1-yl]propan-2-ol
(±)-1-(3-Bromo-carbazol-9-yl)-3-[4-(2,3-dihydro-1,4-benzodioxin-6-ylmethyl)piperazin-1-yl]propan-2-ol
(±)-1-(3-Bromo-carbazol-9-yl)-3-[4-(4-fluorobenzyl)piperazin-1-yl]propan-2-ol
(±)-1-(3-Bromo-carbazol-9-yl)-3-[4-(3,4-dichlorobenzyl)piperazin-1-yl]propan-2-ol
(±)-1-(3-Bromo-carbazol-9-yl)-3-{4-[4-(difluoromethoxy)benzyl]piperazin-1-yl}propan-2-ol
(±)-1-(3-Bromo-carbazol-9-yl)-3-[4-(cyclohexylmethyl)piperazin-1-yl]propan-2-ol
(±)-1-[4-(1,3-Benzodioxol-5-ylmethyl)piperazin-1-yl]-3-(3-bromo-carbazol-9-yl)propan-2-ol
(±)-1-(3-Bromocarbazol-9-yl)-3-[4-(4-methoxybenzyl)piperazin-1-yl]propan-2-ol
(±)-1-(3-Bromocarbazol-9-yl)-3-[4-(4-trifluoromethylbenzyl)piperazin-1-yl]propan-2-ol
(±)-1-(3-Bromo-carbazol-9-yl)-3-[4-(3,5-dichlorobenzyl)piperazin-1-yl]propan-2-ol
(±)-1-(3-Bromo-carbazol-9-yl)-3-[4-(4-tert-butylbenzyl)piperazin-1-yl]propan-2-ol
(±)-1-(3-Bromo-carbazol-9-yl)-3-[4-(2-furylmethyl)piperazin-1-yl]propan-2-ol
(±)-1-(3-Bromo-carbazol-9-yl)-3-[4-(2-furylmethyl)piperazin-1-yl]propan-2-ol
(±)-1-(3-Bromo-carbazol-9-yl)-3-[4-(2-pyridin-ylmethyl)piperazin-1-yl]propan-2-ol
(±)-1-(3-Bromo-Carbazol-9-yl)-3-[4-(3-pyridin-ylmethyl)piperazin-1-yl]propan-2-ol
(±)-1-(3-Bromo-carbazol-9-yl)-3-[4-(4-pyridin-ylmethyl)piperazin-1-yl]propan-2-ol
(±)-1-(3-Bromo-carbazol-9-yl)-3-[4-(quinolin-2-ylmethyl)piperazin-1-yl]propan-2-ol
(±)-1-(3-Bromo-carbazol-9-yl)-3-[4-(2-furyl-4-bromomethyl)piperazin-1-yl]propan-2-ol
(±)-1-(3-Bromo-carbazol-9-yl)-3-[4-(1-naphtylmethyl)piperazin-1-yl]propan-2-ol
(±)-1-{4-[(6-Bromo-1,3-benzodioxol-5-yl)methyl]piperazin-1-yl}-3-(3-bromo-carbazol-9-yl)propan-2-ol
(±)-1-{4-[(6-Chloro-1,3-benzodioxol-5-yl)methyl]piperazin-1-yl}-3-(3-bromo-carbazol-9-yl)propan-2-ol
(±)-1-(3-Chlorocarbazol-9-yl)-3-[4-(4-fluorobenzyl)piperazin-1-yl]propan-2-ol
(±)-1-(3-Chlorocarbazol-9-yl)-3-[4-(2-morpholin-4-ethyl)piperazin-1-yl]propan-2-ol
(±)-1-(3,6-Dibromocarbazol-9-yl)-3-[4-(3-piperidin-1-yl-propyl)piperazin-1-yl]propan-2-ol
(±)-1-(3-Chlorocarbazol-9-yl)-3-(4-cyclohexylpiperazin-1-yl)propan-2-ol
(±)-1-(3-Bromocarbazol-9-yl)-3-[4-(quinolin-4-ylmethyl)piperazin-1-yl]propan-2-ol
(±)-4-[3-(3-Chlorocarbazol-9-yl)-2-hydroxypropyl]-3,5-dimethylpiperazine-1-carboxylic tert-butyl ester
(±)-1-[4-(Cyclohexylmethyl)piperazin-1-yl]-3-(3,6-dichlorocarbazol-9-yl)acetone
(±)-1-[4-(Cyclohexylmethyl)piperazin-1-yl]-3-(3,6-dibromocarbazol-9-yl)acetone
(±)-1-(3,6-Dichlorocarbazol-9-yl)-3-[4-(2-morpholin-4-ethyl)piperazin-1-yl]propan-2-ol
(±)-1-[4-(Cyclohexylmethyl)piperazin-1-yl]-3-(3-phenyl carbazol-9-yl)acetone
(±)-1-(3-Bromocarbazol-9-yl)-3-[4-(2-morpholin-4-ethyl)piperazin-1-yl]propan-2-ol
(±)-1-(3-Chlorocarbazol-9-yl-)-3-(3,5-dimethylpiperazine-1-yl)propan-2-ol
(±)-1-(3-Chlorocarbazol-9-yl-)-3-(2,6-dimethylpiperazin-1-yl)propan-2-ol
(±)-1-(3,6-Dibromocarbazol-9-yl-)-3-piperazin-1-ylpropan-2-amine
(±)-4-[3-(3,6-Dibromocarbazol-9-yl)-2-aminopropyl]-piperazine-1-carboxylic tert-butyl ester
(±)-N-Benzyl-N-[2-(3,6-dibromocarbazol-9-yl)-1-(piperazin-1-ylmethyl)ethyl]amine
(±)-4-[3-(3,6-Dibromocarbazol-9-yl)-2-benzylaminopropyl]-piperazine-1-carboxylic tert-butyl ester
(±)-1-(3,6-Dibromocarbazol-9-yl)-3-[4-(2-morpholin-4-yl-2-oxoethyl)piperazin-1-yl]propan-2-ol
(±)-1-(3,6-Dibromocarbazol-9-yl)-3-{[4-(4,4-difluoro-1,3,5,7-tetramethyl-4-bora-3a,4a-diaza-s-indacene-8-yl)methyl]piperazin-1-yl}propan-2-ol
(±)-1-(3,6-Dibromocarbazol-9-yl)-3-[4-(N-(4,4-difluoro-5,7-dimethyl-4-bora-3a,4a-diaza-s-indacene-3-yl)methylacetamide)piperazin-1-yl]propan-2-ol
(±)-1,6-Dibromocarbazol-9-yl)-3-[4-(N-(4,4-difluoro-1,5,7-tetramethyl-4-bora-3a,4a-diaza-s-indacene-2-yl)acetamide)piperazin-1-yl]propan-2-ol
(±)-4-[({-[3-(3,6-Dibromocarbazol-9-yl)-2-hydroxypropyl]piperazin-1-yl}acetyl)amino]-2-(6-hydroxy-3-oxo-3H-xanthen-9-yl)benzoic acid
(±)-4-({-[3-(3,6-Dibromocarbazol-9-yl)-2-hydroxypropyl]piperazin-1-yl}methyl)-6,7-dimethoxy-2H-chromen-2-one (±)-1-(3,6-Dibromocarbazol-9-yl)-3-{4-[3-(4,4-difluoro-1,3,5,7-tetramethyl-4-bora-3a,4a-diaza-s-indacene-8-yl)-propionyl]piperazin-1-yl}propan-2-ol
(±)-1-[4-(4-Nitro-2,1,3-benzoxadiazol-7-yl)-piperazin-1-yl]-3-(3,6-dibromocarbazol-9-yl)-propan-2-ol Thereby, the most preferred compounds are those which are selected from the group consisting of:
(±)-1-(3,6-Dibromo-carbazol-9-yl)-3-[4-(4-fluoro-benzyl)-piperazin-1-yl]-propan-2-ol
(±)-1-(3-Phenyl carbazol-9-yl)-3-piperazin-1-yl-propan-2-ol;
(±)-3,6-Dibromo-9-(2-fluoro-3-piperazin-1-yl-propyl)-carbazole
(±)-1-(3,6-Dibromo-carbazol-9-yl)-3-piperazin-1-yl-propan-2-one
(±)-1-(3,6-Dibromocarbazol-9-yl)-3-[4-(thien-3-ylmethyl)piperazin-1-yl]propan-2-ol
(±)-1-(3,6-Dibromocarbazol-9-yl)-3-[4-(4-methoxybenzyl)piperazin-1-yl]propan-2-ol
(±)-1-(3,6-Dibromo-carbazol-9-yl)-3-[4-(2-morpholin-4-ethyl)piperazin-1-yl]propan-2-ol
(±)-1-(3-Bromo-carbazol-9-yl)-3-{4-[4-(difluoromethoxy-benzyl]piperazin-1-yl}propan-2-ol
(±)-1-(3,6-Dichlorocarbazol-9-yl)-3-[4-(2-morpholin-4-ethyl)piperazin-1-yl]propan-2-ol
(±)-1-(3,6-Dibromo-carbazol-9-yl-)-3-piperazin-1-ylpropan-2-amine
(R)-1-(3,6-Dibromo-carbazol-9-yl)-3-[4-(4-fluoro-benzyl)-piperazin-1-yl]-propan-2-ol;
(R)-1-(3-Phenylcarbazol-9-yl)-3-piperazin-1-yl-propan-2-ol
(R)-3,6-Dibromo-9-(2-fluoro-3-piperazin-1-yl-propyl)-carbazole
(R)-1-(3,6-Dibromo-carbazol-9-yl)-3-piperazin-1-yl-propan-2-one
(R)-1-(3,6-Dibromocarbazol-9-yl)-3-[4-(thien-3-ylmethyl)piperazin-1-yl]propan-2-ol
(R)-1-(3,6-Dibromocarbazol-9-yl)-3-[4-(4-methoxybenzyl)piperazin-1-yl]propan-2-ol
(R)-1-(3,6-Dibromo-carbazol-9-yl)-3-[4-(2-morpholin-4-ethyl)piperazin-1-yl]propan-2-ol
(R)-1-(3-Bromo-carbazol-9-yl)-3-{4-[4-(difluoromethoxy-benzyl]piperazin-1-yl}propan-2-ol
(R)-1-(3,6-Dichlorocarbazol-9-yl)-3-[4-(2-morpholin-4-ethyl)piperazin-1-yl]propan-2-ol
(R)-1-(3,6-Dibromo-carbazol-9-yl-)-3-piperazin-1-ylpropan-2-amine
(S)-1-(3,6-Dibromo-carbazol-9-yl)-3-[4-(4-fluoro-benzyl)-piperazin-1-yl]-propan-2-ol
(S)-1-(3-Phenylcarbazol-9-yl)-3-piperazin-1-yl-propan-2-ol
(S)-3,6-Dibromo-9-(2-fluoro-3-piperazin-1-yl-propyl)-carbazole
(S)-1-(3,6-Dibromo-carbazol-9-yl)-3-piperazin-1-yl-propan-2-one
(S)-1-(3,6-Dibromocarbazol-9-yl)-3-[4-(thien-3-ylmethyl)piperazin-1-yl]propan-2-ol
(S)-1-(3,6-Dibromocarbazol-9-yl)-3-[4-(4-methoxybenzyl)piperazin-1-yl]propan-2-ol
(S)-1-(3,6-Dibromo-carbazol-9-yl)-3-[4-(2-morpholin-4-ethyl)piperazin-1-yl]propan-2-ol
(S)-1-(3-Bromo-carbazol-9-yl)-3-{4-[4-(difluoromethoxy-benzyl]piperazin-1-yl}propan-2-ol
(S)-1-(3,6-Dichlorocarbazol-9-yl)-3-[4-(2-morpholin-4-ethyl)piperazin-1-yl]propan-2-ol
(S)-1-(3,6-Dibromo-carbazol-9-yl-)-3-piperazin-1-ylpropan-2-amine A further aspect of the present invention is related to the use of the piperazine derivatives of carbazole according to formula I for the preparation of pharmaceutical compositions and their use for treating diseases including Alzheimer's disease, Parkinson's disease, diseases associated with polyglutamine tracts including Huntington's disease, spinocerebellar ataxias and dentatorubral-pallidoluysian atrophy; amyotrophic lateral, sclerosis, Crohn's disease, retinitis pigmentosa and multiple sclerosis, epilepsy), ischemia (stroke, myocardial infarction and reperfusion injury), infertility (like premature menopause, ovarian failure or follicular atresia), cardiovascular disorders (arteriosclerosis, heart failure and heart transplantation), renal hypoxia, hepatitis and AIDS.

According to a preferred embodiment, the above cited diseases or disease states are treated by the modulation of the Bax function, or the modulation (e.g. the inhibition) of the activation or expression of Bax, respectively, via the use of compounds of formula I, whereby the term Bax function notably comprises the actually active form of Bax as an oligomer (see B. Antonsson et al. in 2000 *Biochem. J.*, Vol. 345, 271-278). Through the modulation of the Bax function, a convenient method of treatment of disorders mediated by Bax is expected, including in particular neuronal disorders and/or disorders of the immune system. Said modulation could notably involve the inhibition of the activity (activation) and/or of the expression of Bax. Also, said modulation of the Bax function or activity could actually comprise the inhibition or disruption for instance of the Bid interaction with Bax, which has been shown to play a role within the context of the Bax activation leading to cytochrome c release (see J. C. Martinou et al. in 1999 *The Journal of Cell Biology*, 144(5), 891-901). As a result of the inhibition of the Bax activation by Bid upon using the compounds according to formula I, the cytochrome c release could be inhibited or essentially blocked, thus providing a convenient means to modulate the above described apoptosis pathways. As a result, by said modulation of the apoptosis pathways a whole variety of disorders associated with abnormal apoptosis is expected to be treated.

It is reported herein that the compounds of formula I are suitable to be used as a medicament, i.e. they are suitable for use in treating disorders of the autoimmune system and neuronal system of mammals, notably of human beings. More specifically, the compounds according to formula I, alone or in the form of a pharmaceutical composition, are useful for the modulation, in particular for the inhibition, of the Bax function and/or the Bax activation. More specifically, the compounds according to formula I, alone or in the form of a pharmaceutical composition, are useful for the treatment or prevention of disorders associated with abnormal expression or activation of Bax. The compounds according to formula I could be employed alone or in combination with further pharmaceutical agents. The compounds of formula I are suitable to be used as a medicament alone or in the form of a pharmaceutical composition together with suitable carriers, diluents or excipients. The compounds of formula I are suitable to be used for the preparation of orally administrated pharmaceutical compositions.

Thus, according to the present invention, compounds pursuant to formula I are particularly useful for the treatment or prevention of immuno- and/or neuronal-related diseases or pathological states in which preferably the modulation, in particular the inhibition, of the Bax function and/or the Bax activation plays a crucial role, such as neurodegenerative diseases (e.g. Alzheimer's disease, Parkinson's disease, diseases associated with polyglutamine tracts including Huntington's disease, spinocerebellar ataxias and dentatorubral-pallidoluysian atrophy; amyotrophic lateral sclerosis, Crohn's disease, retinitis pigmentosa and multiple sclerosis, epilepsy), ischemia (stroke, myocardial infarction and reperfusion injury), infertility (like premature menopause, ovarian failure or follicular atresia), cardiovascular disorders (arteriosclerosis, heart failure and heart transplantation), renal hypoxia, hepatitis and AIDS.

As a matter of fact, prior to the herein reported surprisingly found pharmaceutically active pyrrolidine derivatives according to formula I, nothing was known in respect of the use of small molecule chemical compounds as active inhibitors of the pro-apoptosis agent Bax. Nothing was known in respect of the possibility to disrupt or to substantially block—with small molecules—the activation of Bax, for instance via Bid (being another Bcl-2 family member which is involved in the pathways leading to the release of cytochrome c).

A further aspect of the present invention consists in the use of piperazine derivatives of carbazole for the preparation of a pharmaceutical composition for the treatment or prevention of disorders associated with an abnormal Bax function or abnormal (e.g. elevated) Bax activation, an abnormal expression or activity of Bax as well as said pharmaceutical compositions themselves. Hence, such piperazine derivatives of carbazole useful for the preparation of a pharmaceutical composition for the treatment or prevention of disorders associated with the modulation of the Bax function or activation, in particular with the abnormal expression or activity of Bax have the above set out general formula I. Also, the piperazine derivatives of carbazole of the present invention are useful for the treatment of neurodegenerative diseases (e.g. Alzheimer's disease, Parkinson's disease, diseases associated with polyglutamine tracts including Huntington's disease, spinocerebellar ataxias and dentatorubral-pallidoluysian atrophy; amyotrophic lateral sclerosis, Crohn's disease, retinitis pigmentosa and multiple sclerosis, epilepsy), ischemia (stroke, myocardial infarction and reperfusion injury), infertility (like premature menopause, ovarian failure or follicular atresia), cardiovascular dis-orders (arteriosclerosis, heart failure and heart transplantation), renal hypoxia, hepatitis and AIDS.

Still a further aspect of the present invention consists in the actually novel carbazole derivatives of formula I, i.e. those carbazole derivatives according to formula I that have not been disclosed by the prior art. Thereby, a few compounds have been disclosed by 3 different companies, i.e. by the AsInEx Company, by the Bioscreen Company and by the Chembridge Company in as far as they have been mentioned in their company catalogue, without any application and most notably without any indication concerning a potential medical use, though.

Said compounds are the following:
(±)-1-(4-Benzyl-piperazin-1-yl)-3-carbazol-9-yl-propan-2-ol
(±)-1-Carbazol-9-yl-3-[4-(9H-fluoren-9-yl)-piperazin-1-yl]-propan-2-ol
(±)-1-(4-Benzyl-piperazin-1-yl)-3-(3-chloro-carbazol-9-yl)-propan-2-ol
(±)-1-(3,6-Dibromo-carbazol-9-yl)-3-piperazin-1-yl-propan-2-ol
(±)-1-(3,6-Dibromo-carbazol-9-yl)-3-[4-((E)-3-phenyl-allyl)-piperazin-1-yl]-propan-2-ol
(±)-1-(3,6-Dichloro-carbazol-9-yl)-3-[4-((E)-3-phenyl-allyl)-piperazin-1-yl]-propan-2-ol
(±)-1-(4-Benzyl-piperazin-1-yl)-3-(3,6-dichloro-carbazol-9-yl)-propan-2-ol
(±)-1-(3-Bromo-carbazol-9-yl)-3-piperazin-1-yl-propan-2-ol
(±)-1-Carbazol-9-yl-3-(4-pyridin-2-yl-piperazin-1-yl)-propan-2-ol
(±)-1-[4-(3-Carbazol-9-yl-2-hydroxy-propyl)-piperazin-1-yl]-1-phenyl-methanone
(±)-2-{4-[3-(3,6-Dichloro-carbazol-9-yl)-2-hydroxy-propyl]-piperazin-1-yl}-ethanol
(±)-2-[4-(3-Carbazol-9-yl)-2-hydroxy-propyl)-piperazin-1-yl]-ethanesulfonic acid
(±)-1-Carbazol-9-yl-3-piperazin-1-yl-propan-2-ol
(±)-1-(3,6-Dibromo-carbazol-9-yl)-3-[4-(9H-fluoren-9-yl)-piperazin-1-yl]-propan-2-ol
(±)-1-(3,6-Dichloro-carbazol-9-yl)-3-(4-pyridin-2-yl-piperazin-1-yl)-propan-2-ol
(±)-1-Carbazol-9-yl-3-[4-(5,5-dimethyl-4,5-dihydro-thiazol-2-yl)-piperazin-1-yl]-propan-2-ol
(±)-1-(3-Bromo-carbazol-9-yl)-3-[4-(5,5-dimethyl-4,5-dihydro-thiazol-2-yl)-piperazin-1-yl]-propan-2-ol
(±)-1-(3-Bromo-carbazol-9-yl)-3-(4-thiazol-2-yl-piperazin-1-yl)-propan-2-ol
(±)-1-Carbazol-9-yl-3-(4-thiazol-2-yl-piperazin-1-yl)-propan-2-ol
(±)-1-(4-1,3-Benzodioxol-5-ylmethyl-piperazin-1-yl)-3-carbazol-9-yl-propan-2-ol
(±)-1-(4-1,3-Benzodioxol-5-ylmethyl-piperazin-1-yl)-3-(3-bromo-carbazol-9-yl)-propan-2-ol
(±)-1-(4-1,3-Benzodioxol-5-ylmethyl-piperazin-1-yl)-3-(3-chloro-carbazol-9-yl)-propan-2-ol
(±)-1-(3-Bromo-carbazol-9-yl)-3-(4-methyl-piperazin-1-yl)-propan-2-ol
(±)-1-(3-Chloro-carbazol-9-yl)-3-(4-methyl-piperazin-1-yl)-propan-2-ol
(±)-1-(4-Benzyl-piperazin-1-yl)-3-(3,6-dibromo-carbazol-9-yl)-propan-2-ol Furthermore, the following 2 compounds have been disclosed in SU-1584341 of the Physico-Organic Institute in the former Soviet Union in Donetsk,
(±)-1-Carbazol-9-yl-3-piperazin-1-yl-propan-2-ol which has already been cited above as a compound disclosed in a catalogue of the AsInEx company, and (±)-1-(4-Methyl-piperazin-1-yl)-3-carbazol-9-yl-propan-2-ol.

Said 2 compounds of SU-1584341 were described to have an anxiolytic activity.

Hence, the entirely novel carbazole derivatives of the present invention are those of the above set out general formula I, whereby the above identified compounds are excluded. Furthermore, those compounds being novel in the sense of having no known medical use are those of the above set out general formula I, whereby the above identified 2 compounds of SU-1584341 are excluded.

A further document disclosing piperazine derivatives of carbazole is FR-1,167,510 of July 1954. In said document, the piperazine derivatives of carbazole have the general formula V

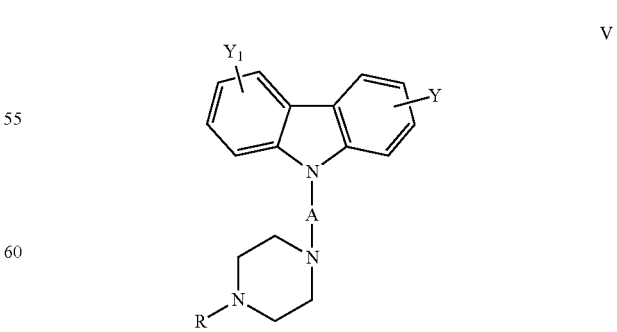

wherein A represents a divalent, saturated aliphatic hydrocarbon radical with a straight or branched chain containing 2 to 6 carbon atoms.

Since within the compounds according to formula I of the present invention, A corresponds to a residue —(CH$_2$)$_n$—X—(CH$_2$)$_m$— wherein X is a substituted, methylene group, more specifically a group of the formula —(CR'R")—, whereby at least one of R', R" is not hydrogen, but a moiety containing at least one heteroatom, i.e. a group comprising or consisting of a substituted $C_1$-$C_6$-alkyl, aryl or heteroaryl, a $C_1$-$C_6$-alkoxy, $C_2$-$C_6$-alkenyl, $C_2$-$C_6$-alkynyl, a primary, secondary or tertiary amino, an acylamino, aminocarbonyl, $C_1$-$C_6$-alkoxycarbonyl, a carboxylic ester acid or amide, halogen, hydroxy, sulfonyl, sulfonamide, $C_1$-$C_6$-thioalkyl, $C_1$-$C_6$-thioalkoxy or where X could be a C=O or a C=S group, the above identified compounds of formula V (FR-1,167,510) are therefore not included by the generic formula I of the present invention.

Also, in the South African patent No. 78/7352, a carbazole compound according to the above formula V of the trade designation "Rimcazole" (an anxiolytic agent), where A is —(CH$_2$)$_3$— and whereby the piperazine moiety is di-substituted with a methyl group is disclosed. Further compounds according to formula V that do have a non-substituted alkyl bridge between the piperazine and the carbazole moiety, wherein R is a diphenylmethyl or an ethylester radical or hydrogen are described by Komissarenko et al. in *Khim.-Farm. Zh*, 24(10), 54-56; 1990 as well as Harfenist et al. in *J. Org. Chem.*, 50(9), 1356; 1985. Such compounds are equally not at all included by the formula I.

The compounds of formula I may contain one or more asymmetric centers and may therefore exist as enantiomers or diasteroisomers. It is to be understood that the invention includes both mixtures and separate individual isomers or enantiomers of the compounds of formula I. In a particularly preferred embodiment the carbazole derivatives according to formula I are obtained in an enantiomeric excess of at least 52% ee, preferably of at least 92-98% ee.

A further aspect of the present invention consists in the use of carbazole derivatives for the preparation of a pharmaceutical composition for the treatment or prevention of disorders associated with abnormal Bax function or Bax activation, an abnormal expression or activity of Bax as well as said pharmaceutical compositions themselves. Such a composition could be prepared by using both the novel and known compounds according to formula I including those of FR-1,167,510 according to formula V as well as those of SU-1584341 and South African patent No. 78/7352. Hence, such piperazine derivatives of carbazole useful for the preparation of a pharmaceutical composition for the treatment or prevention of disorders associated with the modulation of the Bax function or activation, in particular with the abnormal expression or activity of Bax have the general formula

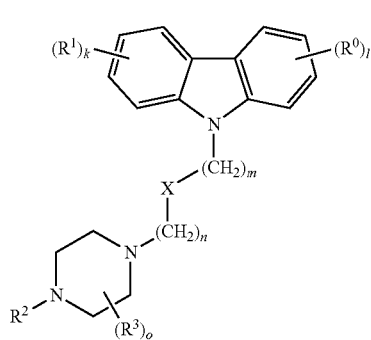

as well as the pharmaceutically acceptable salts and thereof, in racemic or essentially enantiomeric pure form, wherein $R^0$, $R^1$, $R^2$, $R^3$, k, l, m, n and o as well as X are as above defined, i.e. according to the general definition of formula I.

Still a further object of the present invention is the use of carbazole compounds of formula I, wherein $R^2$ is a fluorescent moiety, as a pharmacological tool. Thereby, the preferred fluorescent moieties $R^2$ include (4,4-difluoro-1,3,5,7-tetramethyl-4-bora-3a,4a-diaza-s-indacene-2-yl)acetamide, [(4,4-difluoro-5,7-dimethyl-4-bora-3a,4a-diaza-s-indacene-3-yl)methyl]acetamide, (4,4-difluoro-1,3,5,7-tetramethyl-4-bora-3a,4a-diaza-s-indacen-8-yl)methyl, 2-(6-hydroxy-3-oxo-3H-xanthen-9-yl)-4-(aminoacetyl)benzoic acid, (6,7-dimethoxy-2H-chromen-2-one)-4-methyl, 4,4-difluoro-1,3,5,7-tetramethyl-4-bora-3a,4a-diaza-s-indacene-8-propionyl, 4-nitro-(2,1,3-benzoxadiazol)-7-yl. The fluorescent labelled compounds can be used to study interactions with target proteins, cell permeability and the intracelleular localisation. This is helpful for understanding the mode of action of the Bax inhibiting compounds.

Still a further object of the present invention is a process for preparing the novel piperazine derivatives of carbazole according to formula I which have been set out above.

The piperazine derivatives of carbazole of this invention can be prepared from readily available starting materials using the following general methods and procedures.

It will be appreciated that where typical or preferred experimental conditions (i.e. reaction temperatures, time, moles of reagents, solvents, etc.) are given, other experimental conditions can also be used unless otherwise stated. Optimum reaction conditions may vary with the particular reactants or solvent used, but such conditions can be determined by a person skilled in the art by routine optimisation procedures.

Generally, the piperazine derivatives of the carbazole compound according to the general formula I could be obtained following to Protocol A, i.e. by reacting a carbazole derivative of formula II

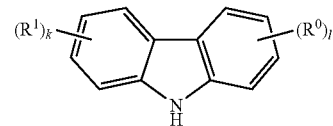

whereby the substituents $R^0$, $R^1$, k and l are as above defined, with a piperazine derivative according to the general formula

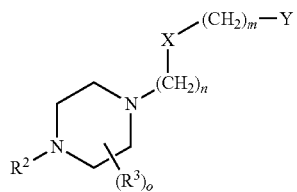

whereby $R^2$ and $R^3$, m, n and o are as above defined, while Y could be any appropriate leaving group. Particularly preferred leaving groups are those selected from the group comprising or consisting of halogen, an aliphatic or aromatic sulfonyloxy group such as methanesulfonyloxy or 4-toluenesulfonyloxy or 3-nitro-benzenesulfonyloxy group.

A particularly preferred method to prepare compounds of formula I in which m=1 and X=CH(OH), is the condensation of compound of formula II and the compound of formula IV.

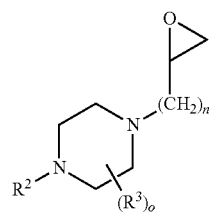

IV

The reaction is carried out between compound III or IV and an anion of compound H which can be formed by reaction of compound II and a base such as sodium hydride, n-butyl lithium in a suitable organic solvent, such as dimethylformamide (DMF) or tetrahydrofuran (THF) for several hours, e.g. 2 hours to 16 hours at room temperature or e.g. at 60° C.

Compounds of formula I can be prepared as individual enantiomers or in an enantiomeric enriched form from the appropriate enantiomer of formula III or as a racemic mixture from the appropriate racemic compound of formula III. Individual enantiomers of the invention can be prepared from racemates by resolution using methods known in the art for the separation of racemic mixtures into their constituent enantiomers, for example using HPLC on a chiral column such as Chiralpak AD, Chiralcel OJ, or using separation of salts of diastereomers.

Compounds of formula II are commercially available compounds or prepared by standard synthetic techniques as hereinafter described in the Examples.

Compounds of formula III can be prepared from the exposure of the corresponding piperazine compounds of formula VI and compounds of formula VIII:

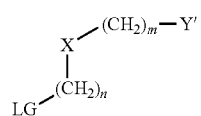

VIII

In which LG is any good leaving group suitably e.g. halogen such as chlorine, bromine or iodine, or an aliphatic or aromatic sulfonyloxy group such as methanesulfonyloxy or 4-toluenesulfonyloxy or 3-nitro-benzenesulfonyloxy or 4-nitro-benzenesulfonyloxy group. X is as previously defined or can be protected by any suitable protecting group. Y' is a precursor of Y, e.g. a protected form of an alcohol, which, after the condensation with the piperazine compound of formula VI, will be transformed into Y, according to procedures known by a person skilled in the art. For all the protection, de-protection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley-Interscience, 1991.

The reaction provides racemic compounds of formula III. (R) as well as (S) enantiomers can be obtained depending upon whether (R) or (S) compound of formula VIII was used as the starting material.

Compounds of formula IV can be prepared from the exposure of the corresponding piperazine compound VI to the compound of formula VII containing any good leaving group (LG) suitably e.g. halogen such as bromine or iodine, or an aliphatic or aromatic sulfonyl-oxy group such as methanesulfonyloxy or 4-toluenesulfonyloxy or 3-nitrobenzenesulfonyloxy or 4-nitro-benzenesulfonyloxy group in the presence of a base such as potassium carbonate in a suitable solvent e.g. acetonitrile.

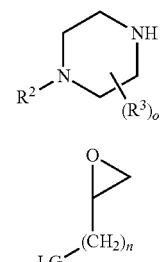

VI

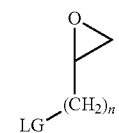

VII

The reaction provides racemic compounds of formula IV. (R) as well as (S) enantiomers can be obtained depending upon whether (R) or (S) compound of formula VII was used as the starting material.

Compounds of formula VI, VII and VIII are commercially available or prepared by standard synthetic techniques as hereinafter described in the examples.

An alternative method of preparation of the carbazole compounds of formula I consists in the following Protocol B. Thereby, the piperazine derivatives of the carbazole compound according to the general formula I could be obtained by reacting a carbazole derivative of formula IX

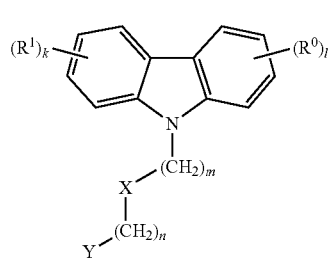

IX whereby the substituents $R^0$, $R^1$, k, l, m and n are as above defined, while Y could be any appropriate leaving group with a piperazine derivative according to the general formula VI. Particularly preferred leaving groups are those selected from the group comprising or consisting of halogen, an aliphatic or aromatic sulfonyloxy group such as methanesulfonyloxy or 4-toluenesulfonyloxy or 3-nitro-benzenesulfonyloxy group.

The preferred method to prepare compounds of formula I in which m=1 and X=CH(OH), is the condensation of compound of formula VI and the compound of formula X.

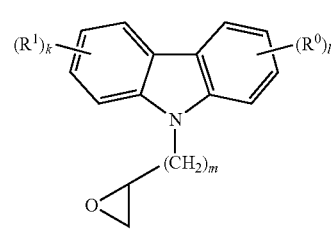

X

The reaction is carried out between compound Ix or XIII and an compound VI in a suitable organic solvent, such as ethanol (EtOH), acetonitrile (ACN) or a mixture of EtOH/tetrahydrofuran (THF) (1/1) for several hours, e.g. 2 hours to 16 hours at room temperature or at 60° C. or at 80° C.

Compounds of formula I can be prepared as individual enantiomers or in an enantiomeric enriched form from the appropriate enantiomer of formula XIII or as a racemic mixture from the appropriate racemic compound of formula X. Individual enantiomers of the invention can be prepared from racemates by resolution using methods known in the art for the sepa-ration of racemic mixtures into their constituent enantiomers, for example using HPLC on a chiral column such as Chiralpak AD, Chiralcel OJ, or using separation of salts of diastereo-mers.

Compounds of formula IX can be prepared from the exposure of the corresponding carbazole compounds of formula II and compounds of formula XI:

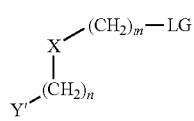

XI

In which LG is any suitable leaving group including halogen such as chlorine, bromine or iodine, or an aliphatic or aromatic sulfonyloxy group such as methanesulfonyloxy or 4-toluenesulfonyloxy or 3-nitro-benzenesulfonyloxy or 4-nitro-benzenesulfonyloxy group. X is as previously defined or can be protected by any suitable protecting group. Y' is a precursor of Y, e.g. a protected form of an alcohol, which, after the condensation with the carbazole compound of formula II, will be transformed into Y, according to procedures known by a person skilled in the art. For all the protection, de-protection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley-Interscience, 1991.

The reaction provides racemic compounds of formula IX. (R) as well as (S) enantiomers can be obtained depending upon whether (R) or (S) compound of formula XII was used as the starting material.

Compounds of formula X may be prepared by contacting the corresponding carbazole compound H with the compound of formula XII containing a suitable leaving group (LG) including for instance halogen such as bromine or iodine, or an aliphatic or aromatic sulfonyl-oxy group such as methanesulfonyloxy or 4-toluenesulfonyloxy or 3-nitro-benzenesulfonyl-oxy or 4-nitro-benzenesulfonyloxy group in the presence of a base such as sodium hydride in a suitable solvent e.g. THF or acetonitrile.

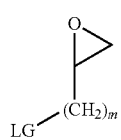

XII

The reaction provides racemic compounds of formula XIII (R) as well as (S) enantiomers can be obtained depending upon whether (R) or (S) compound of formula XII was used as the starting material.

Compound of formula XI and XII are commercially available compounds or may be prepared upon using standard synthetic techniques as hereinafter described in the examples.

A more preferred preparation of compound XIII is the exposure of the corresponding carbazole compound II to the compound of formula XII when LG is an hydroxy group. The reaction is carried out by standard Mitsunobu reaction conditions i.e. diethyl (E)-1,2-diazenedicarboxylate (DEAD), PPh$_3$ in anhydrous THF or using (E)-N$^1$,N$^1$,N$^2$,N$^2$-tetramethyl-1,2-diazenedicarboxamide (TMAD) and PBu$_3$, or (trimethyl phosphoranylidene)acetonitrile (CMMP) which is prepared according to the protocol of Tetsuto, Tsunoda *Tett. Lett.* 1996, 37(14), 2459-2462, or (tributylphosphoranylidene) acetonitrile (CMBP) in a suitable anhydrous solvent such as toluene or THF.

Following a third approach (Protocol C), a one-step-procedure, the piperazine derivatives of carbazole compound according to the general formula I could be obtained by reacting the carbazole derivative of formula II, the compound of formula VII containing any good leaving group suitably e.g. halogen such as bromine or iodine, or an aliphatic or aromatic sulfonyloxy group such as methanesulfonyloxy or 4-toluenesulfonyloxy or 3-nitrobenzenesulfonyloxy or 4-nitrobenzenesulfonyloxy group, e.g. (±)-3-nitrobenzene sulfonic acid oxiranylmethyl ester, and the piperazine derivative of formula VI. The reaction is carried out in a basic medium, such as ethanol, THF or ACN in the presence of a suitable base e.g. NaH.

The method of preparation of the carbazole compounds of formula I according to Protocole B and C has the specific advantage of being more convenient and economic, in the sense that it comprises less steps.

Compounds of formula XI and XII are commercially available or prepared by synthetic techniques as hereinafter described in Examples.

Particularly preferred intermediate compounds of formula II, III, IV, IX and XIII for the pre-paration of a compound according to formula I are selected from the group consisting of:

(t)-1-Benzyl-4-oxiranylmethyl-piperazine
(s)-4-Oxiranylmethyl-piperazine-1-carboxylic acid tert-butyl ester
(R)-4-Oxiranylmethyl-piperazine-1-carboxylic acid tert-butyl ester
(±)-1-(3,4-Dichloro-phenyl)-4-oxiranylmethyl-piperazine
(±)-1-(1,3-Benzodioxol-5-ylmethyl)-4-oxiranylmethyl-piperazine
(±)-1-(4-Fluoro-benzyl)-4-oxiranylmethyl-piperazine
3-Phenyl-9H-carbazole
3,6-Diphenyl-9H-carbazole
(±)-1-Oxiranylmethyl-4-(3-phenyl-propyl)-piperazine
(±)-1-Oxiranylmethyl-4-(3-phenyl-1,2,4-thiadiazol-5-yl)-piperazine
(±)-1-(Cyclohexylmethyl)-4-(oxiran-2-ylmethyl)piperazine
(±)-1-(4-Fluorophenyl)-4-oxiran-2-ylmethyl)piperazine
3-[4-(Trifluoromethyl)phenyl]-9H-carbazole
3-[4-(Trifluoromethoxy)phenyl]-9H-carbazole
(±)-3,6-Dibromo-9-(oxiran-2-ylmethyl)carbazole
3-Thien-2-yl-9H-carbazole
(±)-3-Chloro-9-(oxiran-2-ylmethyl)carbazole
(±)-1-(Oxiran-2-ylmethyl)-4-(3-piperidin-1-ylpropyl)piperazine
(±)-3-Nitro-9-(oxiran-2-ylmethyl)carbazole
3-Nitro-9-[(1E)-3-(3-nitrocarbazol-9-yl)propen-1-enyl]carbazole.

The above mentioned novel intermediate compounds are a further aspect of the present invention.

According to a further general process, compounds of formula I can be converted to alternative compounds of formula I, employing suitable interconversion techniques such as hereinafter described in the Examples.

If the above set out general synthetic methods are not applicable for obtaining compounds according to formula I and/or necessary intermediates for the synthesis of compounds of formula I, suitable methods of preparation known by a person skilled on the art should be used. In general, the synthesis pathways for any individual compound of formula I will depend on the specific substitutents of each molecule and upon the ready availability of intermediates necessary; again such factors being appreciated by those of ordinary skill in the art.

Compounds of this invention can be isolated in association with solvent molecules by crystallization from evaporation of an appropriate solvent. The pharmaceutically acceptable acid addition salts of the compounds of formula I, which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula I with a suitable base. Both types of salt may be formed or interconverted using ion-exchange resin techniques.

A final aspect of the present invention is related to the formulations containing the active compounds according to formula I. When employed as pharmaceuticals, the carbazole derivatives of the present invention are typically administered in the form of a pharmaceutical composition. Hence, pharmaceutical compositions comprising a compound of formula I and a pharmaceutically acceptable carrier, diluent or excipient therefore are also within the scope of the present invention. A person skilled in the art is aware of a whole variety of such carrier, diluent or excipient compounds suitable to formulate a pharmaceutical composition. Also, the present invention provides compounds for use as a medicament. In particular, the invention provides the compounds of formula I for use as Bax antagonist, for the treatment of disorders of mammals, notably of human beings associated with inappropriate cell death, including neurodegenerative disorders, diseases associated with polyglutamine tracts, epilepsy, ischemia, infertility, cardiovascular disorders, renal hypoxia, hepatitis and AIDS, either alone or in combination with other medicaments.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral administration (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the carbazole derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the carbazole compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like.

Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the carbazole compound or carbazole compounds of formula I in such compositions is/are typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences*, $17^{th}$ Edition, 1985, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples which are not construed to be viewed as limiting the scope of the invention.

EXAMPLES

The following abbreviations are hereinafter used in the accompanying examples: min (minute), hr (hour), g (gram), mmol m.p. (melting point), eq (equivalents), mL (milliliter), μL (microliters), mL (milliliters), DCM (dichloromethane), TFA (trifluoro-acetic acid), rt (room temperature), DMSO (dimethylsulfoxide), DMSO-d$_6$ (deuterated dimethylsulfoxide), THF (tetrahydrofuran), MgSO$_4$ (magnesium sulfate), CDCl$_3$ (deuterated chloroform), TEA (triethyl amine), NaH (sodium hydride), nBuLi (n Butyl Lithium), EtOAc (ethyl acetate), cHex (cyclohexanes), Et$_2$O (diethyl ether), ACN (acetonitrile), PetEther (petroleum ether), NaHCO$_3$ (sodium bicarbonate), HOBt (1-hydroxybenzotriazole), EDCI (1-(3-dimethyl-amino-propyl)-3-ethylcarbodiimide), dimethylformamide (DMF), K$_2$CO$_3$ (potassium carbonate), TMOF (trimethyl ortho formiate), DAST [(diethylamino)sulfur trifluoride], DEAD (diethyl (E)-1,2-diazenedicarboxylate), CMMP (trimethyl phosphoranylidene)acetonitrile.

The below described intermediates 1-19 are novel. They are particularly advantageous for the preparation of the compounds according to formula I, notably for the hereinafter exemplified compounds 1-124.

Intermediate 1

(±)-1-Benzyl-4-oxiranylmethyl-piperazine

To a solution of 2-bromomethyl-oxirane (2.3 mL, 27.5 mmol) in 40 mL of ACN are added K$_2$CO$_3$ (3.8 g, 27.5 mmol) and a solution of 1-benzyl-piperazine (5.81 g, 25 mmol) in 60 mL of ACN. After 24 hr at rt the reaction is judged to be completed by tlc monitoring (SiO$_2$, DCM:MeOH 20:1). The reaction mixture is filtered off and the filtrate is concentrated in vacuo. Flash chromatography on a 7×15 cm$^2$ column of SiO$_2$ using DCM:MeOH (20:1) as eluting solvent and removal of the solvent gives the title compound (4.87 g, 84%) as a colorless oil.

$^1$H NMR (CDCl$_3$, 300 MHz) δ 7.34-7.24 (m, 5H), 3.55 (system AB, 2H, Aa=14.9 Hz, J=13.3 Hz), 3.11 (m, 1H), 2.76 (dd, 1H, J=9.1, 5.1 Hz), 2.70 (dd, 1H, J=13.2, 6.6 Hz), 2.53-2.47 (m, 8H), 2.48 (dd, 1H, J=5.1, 2.7 Hz), 2.31 (dd, 1H, J=13.2, 6.6 Hz).

Intermediate 2

(S)-4-Oxiranylmethyl-piperazine-1-carboxylic acid tert-butyl ester

The same method as employed in the preparation of Intermediate 1 but starting from piperazine-1-carboxylic acid tert-butyl ester and (R)-(−)-3-nitro-benzenesulfonic acid oxiranylmethyl ester gives after flash chromatography the title compound as a yellow oil in a 70% yield.

$^1$H NMR (CDCl$_3$, 300 MHz) δ 3.42 (m, 3H), 3.08 (m, 1H), 2.76 (m, 2H), 2.57-2.45 (m, 6H), 2.25 (dd, 1H, J=13.3, 6.9 Hz), 1.44 (s, 9H). 96% ee (Chiralcel OJ column, rt, hexanes: iPrOH (95:5), 210 nM, 0.5 mL/min).

Intermediate 3

(R)-4-Oxiranylmethyl-piperazine-1-carboxylic acid tert-butyl ester

The same method as employed in the preparation of Intermediate 1 but starting from piperazine-1-carboxylic acid tert-butyl ester and (S)-(+)-3-nitro-benzenesulfonic acid oxiranylmethyl ester gives after flash chromatography the title compound as a yellow oil in a 68% yield.

$^1$H NMR (CDCl$_3$, 300 MHz) δ 3.42 (m, 3H), 3.08 (m, 1H), 2.76 (m, 2H), 2.57-2.45 (m, 6H), 2.25 (dd, 1H, J=13.3, 6.9 Hz), 1.44 (s, 9H). 96% ee (Chiralcel OJ column, rt, hexanes: iPrOH (95:5), 210 nM, 0.5 mL/min).

Intermediate 4

(±)-1-(3,4-Dichloro-phenyl)-4-oxiranylmethyl-piperazine

The same method as employed in the preparation of Intermediate 1 but starting from 1-(3,4-dichloro-phenyl)-piperazine) and 3-nitro-benzenesulfonic acid oxiranylmethyl ester gives after Biotage chromatography the title compound as a yellow oil in a 97% yield.

$^1$H NMR (CDCl$_3$, 300 MHz) δ 725 (d, 1H, J=9.0 Hz), 6.93 (d, 1H, J=2.9 Hz), 6.71 (dd, 1H, J=9.0, 2.9 Hz), 3.17 (m, 4H), 2.84 (m, 1H), 2.79 (dd, 1H, J=13.3, 3.2 Hz), 2.78-2.62 (m, 5H), 2.48 (dd, 1H, J=5.0, 2.7 Hz), 2.26 (dd, 1H, J=13.3, 7.0 Hz).

Intermediate 5

(±)-1-(1,3-Benzodioxol-5-ylmethyl)-4-oxiranylmethyl-piperazine

The same method as employed in the preparation of Intermediate 1 but starting from 1-benzo[1,3]dioxo-5-ylmethylpiperazine gives after flash chromatography the title compound as an orange oil in a 100% yield.

$^1$H NMR (DMSO-d$_6$, 300 MHz) δ 6.82 (m, 2H), 6.72 (dd, 1H, J=7.8, 1.5 Hz), 5.97 (s, 2H), 4.07 (dd, 1H, J=5.4, 5.4 Hz), 3.32 (s, 2H), 2.97 (m, 1H), 2.66 (dd, 1H, J=3.6, 1.3 Hz), 2.57 (dd, 1H, J=13.2, 3.6 Hz), 2.41 (dd, 1H, J=5.1, 2.7 Hz), 2.34 (br s, 8H), 2.17 (dd, 1H, J=13.2, 6.6 Hz).

Intermediate 6

(±)-1-(4-Fluoro-benzyl)-4-oxiranylmethyl-piperazine

The same method as employed in the preparation of Intermediate 1 but starting from 1-(3-fluoro-benzyl)-piperazine gives after flash chromatography the title compound as a colorless oil in a 83% yield.

$^1$H NMR (CDCl$_3$, 300 MHz) δ 7.25 (m, 2H), 6.95 (m, 2H), 3.45 (system AB, 2H, Δα=14.9, J=13.3 Hz), 3.07 (m, 1H), 2.70 (dd, 1H, J=13.2, 3.6 Hz), 2.60-2.44 (m, 10H), 2.26 (dd, 1H, J=13.2, 6.7 Hz).

Intermediate 7

3-Phenyl-9H-carbazole

To a solution of 3-bromo-9H-carbazole (0.4 g, 1.6 mmol) in DMF:H$_2$O (15 mL:2 mL) are added tetrakis(triphenylphosphine)-palladium (0.184 g, 0.1 eq), potassium carbonate (0.66 g, 3 eq) and phenyl boronic acid (0.58 g, 3 eq). The resulting mixture is stirred at 80° C. for 4 hr. After cooling to rt, DCM (10 mL) is added and the reaction mixture is quenched with brine. After extraction, drying over MgSO$_4$ and concentration in vacuo, the residue is purified via flash chromatography using PetEther:EtOAc 10:1 as eluting solvent to give the title compound (0.35 g, 1.44 mmol) as a white powder in a 90% yield. M.p.: 221° C.

$^1$H NMR (CDCl$_3$, 300 MHz) δ 8.17 (d, 1H, J=1.5 Hz), 8.01 (d, 1H, J=7.8 Hz), 7.97 (br s, 1H), 7.81-7.37 (m, 3H), 7.60-7.30 (m, 7H).

Intermediate 8

3,6-Diphenyl-9H-carbazole

The same method as employed in the preparation of Intermediate 7 but starting from 3,6-dibromo-9H-carbazole gives after flash chromatography the title compound as a white solid in a 33% yield. M.p.: 145-147° C.

$^1$H NMR (CDCl$_3$, 300 MHz) δ 8.32 (d, 2H, J=1.2 Hz), 8.09 (s, 1H), 7.72-7.66 (m, 6H), 7.50-7.43 (m, 6H), 7.35-7.30 (m, 2H).

Intermediate 9

(±)-1-Oxiranylmethyl-4-(3-phenyl-propyl)-piperazine

The same method as employed in the preparation of Intermediate 1 but starting from 1-(3-phenylpropyl)-piperazine and 3-nitro-benzenesulfonic acid oxiranylmethyl ester gives after Biotage chromatography the title compound as a yellow oil in a 80% yield.

$^1$H NMR (CDCl$_3$, 300 MHz) δ 7.23-7.09 (m, 5H), 3.02 (m, 1H), 2.72-2.32 (m, 15H), 2.26 (dd, 1H, J=13.2, 6.8 Hz), 1.82 (m, 2H).

Intermediate 10

(±)-1-Oxiranylmethyl-4-(3-phenyl-1,2,4-thiadiazol-5-yl)-piperazine

The same method as employed in the preparation of Intermediate 1 but starting from 1-(3-phenyl-1,2,4-thiadiazol-5-yl)-piperazine and 3-nitro-benzenesulfonic acid oxiranylmethyl ester gives after Biotage chromatography the title compound as a white powder in a 60% yield.

$^1$H NMR (CDCl$_3$, 300 MHz) δ 8.07 (m, 2H), 7.30 (m, 3H), 3.53 (br s, 3H), 3.14-2.20 (m, 10H).

Intermediate 11

(±)-1-(Cyclohexylmethyl)-4-(oxiran-2-ylmethyl)piperazine

The same method as employed in the preparation of Intermediate 1 but starting from 1-cyclohexylmethyl piperazine and (±)-3-nitro-benzenesulfonic acid oxiranylmethyl ester gives after flash chromatography the title compound as a yellow oil in a 92% yield.

$^1$H NMR (CDCl$_3$, 300 MHz) δ 3.02 (m, 1H), 2.72-2.32 (m, 10H), 2.26 (dd, 1H, J=13.2, 6.8 Hz), 2.06 (d, 1H, J=7.2 Hz), 1.82 (m, 6H), 1.4 (m, 1H), 1.4 (m, 4H), 0.8 (m, 2H).

Intermediate 12

(±)-1-(4-Fluorophenyl)-4-oxiran-2-ylmethyl)piperazine

The same method as employed in the preparation of Intermediate 1 but starting from 4-fluorophenylpiperazine, dihydrochloride and (±)-3-nitro-benzenesulfonic acid oxiranylmethyl ester gives after flash chromatography the title compound as a yellow oil in a 25% yield.

$^1$H NMR (CDCl$_3$, 300 MHz) δ 6.97-6.83 (2 d, J=8.3 Hz, 4H), 3.2 (m, 5H), 2.80-2.60 (m, 8H), 2.50 (dd, 1H, J=5.0, 2.7 Hz), 2.3 (dd, 1H, J=13.2, 6.9 Hz).

Intermediate 13

3-[4-(Trifluoromethyl)phenyl]-9H-carbazole

The same method as employed in the preparation of Intermediate 7 but starting from 4-trifluoromethylphenyl boronic acid gives after Biotage chromatography the title compound as a white powder in a 60% yield.

FI-MS (APCI): m/z observed in a negative mode: 310.0.

Intermediate 14

3-[4-(Trifluoromethoxy)phenyl]-9H-carbazole

The same method as employed in the preparation of Intermediate 7 but starting from 4-trifluoromethoxyphenyl boronic acid gives after Biotage chromatography the title compound as a white powder in a 97% yield.

FI-MS (APCI): m/z observed in a negative mode: 325.8.

Intermediate 15

(±)-3,6-Dibromo-9-(oxiran-2-ylmethyl)carbazole

Following Protocol A:

At rt a solution of 3,6-dibromo-9H-carbazole (5.23 g, 16.10 mmol) in anhydrous THF (200 mL) is treated with NaH (0.703 g, 16.10 mmol, 55% in mineral oil) and a solution of (±)-3-nitro-benzene sulfonic acid oxiranyl methyl ester (4.17 g, 16.10 mmol) in anhydrous THF (30 mL). After 16 hours of stirring at rt the reaction mixture is quenched with a saturated aqueous solution of sodium hydrogenocarbonate (200 mL). Extraction with Et$_2$O (500 mL+2×250 mL), drying over MgSO$_4$ and evaporation under reduced pressure gives a yellow solid. Flash chromatography on a 7×27 cm$^2$ column of SiO$_2$ using DCM/Petroleum Ether (1/1) gives the title compound (3.65 g, 9.58 mmol) as a white solid in a 59% yield.

Following Protocol B:

At rt under an inert atmosphere, (±)-glycyclol (0.129 g, 1.74 mmol, 120 uL) is added into a solution of 3,6-dibromo-9-H-carbazole (0.565 g, 1.74 mmol) in anhydrous toluene (10 mL). Then CMMP (which is prepared according to the protocol of Tetsuto, Tsunoda *Tett. Lett.* 1996, 37(14), 2459-2462) (0.20 g, 1.74 mmol) is added. The resulting mixture is allowed to stir at rt for 16 hours. The solvent is evaporated and the crude compound is purified via flash chromatography using Biotage device and Petroleum Ether/DCM (3/1) as eluant to give the title compound in a 60% yield as a white solid and 5% of (±)-3,6-dibromo-9-[(1E)-3-(3,6-dibromocarabazol-9-yl)propen-1-enyl]carbazole as a grey powder.

(±)-3,6-Dibromo-9-(oxiran-2-ylmethyl)carbazole:
$^1$H NMR (CDCl$_3$, 300 MHz) δ 8.11 (d, 2H, J=1.9 Hz), 7.55 (dd, 2H, J=8.7, 1.9 Hz), 7.31 (d, 2H, J=8.7 Hz), 4.62 (dd, J=16.0, 2.7 Hz, 1H), 4.25 (dd, J=16.0, 5.1 Hz, 1H), 3.29 (dddd, J=5.1, 4.0, 2.7, 2.6 Hz, 1H), 2.79 (dd, J=4.7, 4.0 Hz, 1H), 2.47 (dd, 1H, J=4.7, 2.6 Hz, 1H).

(±)-3,6-Dibromo-9-[(1E)-3-(3,6-dibromocarabazol-9-yl)propen-1-enyl]carbazole:
$^1$H NMR (CDCl$_3$, 300 MHz) δ 8.6-8.4 (4H, m), 8.07-7.41 (9H, m), 6.34-6.1 (1H, m), 5.5-5.2 (2H, d, J=6.0 Hz).

FI-MS (APCI): m/z observed in a negative mode: 687.2

Intermediate 16

3-Thien-2-yl-9H-carbazole

Under an inert atmosphere a solution of 3-bromo-2-yl-9H-carbazole (0.100 g, 0.408 mmol) in degassed NMP (10 mL) is treated with triphenyl arsine (0.025 g, 0.0816 mmol, 0.2 equiv.), Pd₂ dba₃ (0.0187 g, 0.0204 mmol, 5 mol %) and tributyl(thien-2-yl)stannane (0.167 mg, 0.449 mmol, 1.1 equiv.). The resulting mixture is allowed to stir for 20 hours at 80° C. The reaction mixture is quenched with a solution of KF (1M) for 1 hour. Extraction with DCM, drying over MgSO₄ and evaporation under reduced pressure gives a residue. HPLC purification and recrystallization from Et₂O gives the title compound as a yellow solid in a 20% yield.

FI-MS (APCI): m/z observed in a negative mode: 248.0.

Intermediate 17

(±)-3-Chloro-9-(oxiran-2-ylmethyl)carbazole

The same method as employed in the preparation of Intermediate 15 but starting from 3-chloro-9H-carbazole gives after Biotage chromatography the title compound as a yellow oil in a 78% yield.

¹H NMR (CDCl₃, 300 MHz) δ 8.03 (m, 1H), 7.49-7.25 (m, 6H), 4.62 (dd, 1H, J=16.0, 2.7 Hz), 4.25 (dd, 1H, J=16.0, 5.1 Hz), 3.29 (dddd, 1H, J=5.1, 4.0, 2.7, 2.6 Hz), 2.79 (dd, 1H, J=4.7, 4.0 Hz), 2.47 (d, 1H, J=4.7, 2.6 Hz).

Intermediate 18

(±)-1-(Oxiran-2-ylmethyl)-4-(3-piperidin-1-ylpropyl)piperazine

The same method as employed in the preparation of Intermediate 1 but starting from 1-(3-piperidin-1-ylpropyl)piperazine and (±)-3-nitro-benzenesulfonic acid oxiranylmethyl ester gives after flash chromatography the title compound as an orange oil in a 64% yield.

¹H NMR (CDCl₃, 300 MHz) δ 2.9 (m, 1H), 2.6-2.1 (m, 20H), 1.61 (m, 2H), 1.4 (m, 4H), 1.2 (m, 2H).

FI-MS (APCI): m/z observed in a positive mode: 268.2.

Intermediate 19

(±)-3-Nitro-9-(oxiran-2-ylmethyl)carbazole

Protocol B (using DEAD, PPh₃):

At rt under an inert atmosphere, (±)-glycyclol (0.018 g, 20 uL, 0.24 mmol) is added into a solution of 3-nitro-9H-carbazole (0.050 g, 0.24 mmol) in anhydrous THF (5 mL). Then PPh₃ (0.126 g, 0.48 mmol, 2.0 equiv.) is added neat. The resulting mixture is allowed to cool to 0° C. (ice bath) and DEAD (0.084 g, 0.48 mmol, 2.0 equiv.) is added. The resulting reaction mixture is allowed to stir at rt for 16 hours. The solvent is evaporated and the crude compound is purified via flash chromatography using Biotage device and EtOAc/cyclohexane (1/3) as eluant to give the title compound in a 95% yield as a yellow solid. ¹H NMR (DMSO d-₆, 300 MHz) δ 9.20 (d, 1H, J=2.26 Hz), 8.47-8.40 (m, 1H), 8.34 (dd, 1H, J=9.04, 2.26 Hz), 7.93-7.74 (m, 2H), 7.65-7.53 (m, 1H), 4.96 (dd, 1H, $J_{AB}$=15.64 Hz, $J_{AX}$=2.83 Hz), 4.54 (dd, 1H, $J_{AB}$=15.64 Hz, $J_{AX}$=5.84 Hz), 3.43-3.35 (m, 1H), 2.79 (t, 1H, J=4.52 Hz), 2.58 (dd, 1H, J=4.9, 2.64 Hz).

Protocol B (using CMMP):

The same method as employed in the preparation of Intermediate 15 but starting from 3-nitro-9H-carbazole gives the title compound in a 50% yield as a yellow powder. Heating up the reaction mixture in THF up to 80° C. leads to the formation of 3-nitro-9-[(1E)-3-(3-nitrocarbazol-9-yl)propen-1-enyl]carbazole in a 10% yield. Using glycyclol (1 equiv.), CMMP (2 equiv.) and 3-nitro-9H-carbazole (2 equiv.) in toluene at 110° C. gives 3-nitro-9-[(1E)-3-(3-nitrocarabazol-9-yl)propen-1-enyl]carbazole in a 90% yield.

3-Nitro-9-[(1E)-3-(3-nitrocarbazol-9-yl)propen-1-enyl]carbazole:

¹H NMR (DMSO d-₆, 300 MHz) δ 9.26 (d, 1H, J=2.26 Hz), 9.15 (d, 1H, J=2.07 Hz), 8.5-8.24 (m, 4H), 8.09 (d, 1H, J=9.03 Hz), 8.04 (d, 1H, J=8.28 Hz), 7.99-7.74 (m, 3H), 7.70-7.45 (m, 2H), 7.44-7.2 (m, 2H), 6.5-6.35 (dt, 1H, J=13.94 Hz, 6.92 Hz), 5.47 (d, 2H, J=6.6 Hz)

FT-MS (APCI) m/z observed in a negative mode: 461.0.

Example 1

(±)-1-(4-Benzyl-piperazin-1-yl)-3-(2-methyl-carbazol-9-yl)-propan-2-ol

To a solution of 2-methyl-9H-carbazole (0.5 g, 2.76 mmol) in 10 mL of THF is added n-BuLi (1.6 M in hexanes, 1.8 mL, 1.1 eq) under inert atmosphere. After 15 min of stirring at rt a solution of Intermediate 1 in 4 mL of THF is added. After 16 hr at rt the reaction is judged to be completed by tlc monitoring (SiO₂, cHex:EtOAc 80:20) and is quenched with 10 mL of a saturated aqueous solution of K₂CO₃. The reaction mixture is extracted with DCM, washed with brine (10 mL), dried over MgSO₄ and concentrated in vacuo. Flash chromatography on a 2×20 cm² column using cHex:EtOAc (80:20) as eluting solvent and removal of the solvent in vacuo gives the title compound as a foam. Slow addition of HCl (10 mL, 1M in Et₂O) into a solution of the above compound in EtOH (3 mL) gives the hydrochloride salt of the title compound (0.39 g) as a beige powder in a 35% yield.

Mp: 239° C. (decomposition).
Analysis for C₂₇H₃₁N₃O. 2HCl:
Calculated: C, 66.66; H, 6.84; N, 8.64;
Found: C, 66.45; H, 6.92; N, 8.51%:

Example 2

(±)-4-(3-Carbazol-9-yl-2-hydroxy-propyl)-piperazine-1-carboxylic tert-butyl ester The same method as employed in the preparation of Example 1 but starting from 9H-carbazole and (±)-4-oxiranylmethyl-piperazine-1-carboxylic acid tert-butyl ester (prepared according to the procedure of Toldy, L. et al., WO 97/14685) gives after flash chromatography the title compound as a pale yellow foam in a 82% yield.

¹H NMR (CDCl₃, 300 MHz) δ 8.07 (d, 2H, J=7.8 Hz), 7.45 (m, 4H), 7.20 (m, 2H), 4.37 (d, 2H, J=5.3 Hz), 4.20 (m, 1H), 3.38 (br s, 5H), 2.54-2.44 (m, 4H), 2.40 (m, 2H), 1.44 (s, 9H).

Example 3

(±)-1-Carbazol-9-yl-3-piperazin-1-yl-propan-2-ol

At rt to a solution of Example 2 (3.4 g, 8.30 mmol) in DCM (120 mL) is added TFA (30 mL). The resulting mixture is stirred at rt for 30 min. Concentration in vacuo gives an oily residue. Flash chromatography on a 7×18 cm² column of SiO₂ using DCM:MeOH:TEA (40:5:3) as eluting solvent and removal of the solvent gives the title compound (3.12 g, 92%) as a white foam. Slow addition of HCl (30 mL, 4 eq, 1M in Et₂O) into a solution of the above compound in EtOH (40 mL) gives the hydrochloride salt of the title compound as beige crystals in a quantitative yield.

M.p.: 245-250° C. (decomposition).

Analysis for C₁₉H₂₃N₃O. 2HCl. 0.65H₂O:
Calculated: C, 57.91; H, 6.73; N, 10.60; Cl, 17.99;
Found: C, 57.93; H, 6.67; N, 10.61; Cl, 18.03%.

Example 4

(±)-4-[3-(3,6-Dibromocarbazol-9-yl)-2-hydroxy-propyl]-piperazine-1-carboxylic tert-butyl ester The same method as employed in the preparation of Example 1 but starting from 3,6-dibromo-9H-carbazole, (±)-4-oxiranylmethyl-piperazine-1-carboxylic acid tert-butyl ester and sodium hydride gives after flash chromatography the title compound as a white foam in a 72% yield. M.p: 90-95° C.
$^1$H NMR (CDCl₃, 300 MHz) δ 8.08 (d, 2H, J=1.9 Hz), 7.51 (dd, 2H, J=8.7, 1.9 Hz), 7.32 (d, 2H, J=8.7 Hz), 4.3-4.1 (m, 3H), 3.36 (br s, 4H), 2.50 (m, 2H), 2.36 (m, 2H), 2.26 (m, 2H), 1.45 (s, 9H).

Example 5

(±)-1-(3,6-Dibromocarbazol-9-yl)-3-piperazin-1-yl-propan-2-ol

The same method as employed in the preparation of Example 3 but starting from (±)-4-[3-(3,6-dibromocarbazol-9-yl-2-hydroxy-propyl)-piperazine-1-carboxylic tert-butyl ester gives after flash chromatography the trifluoro acetate salt of the title compound as a white solid in a 63% yield.
M.p.: 133° C.
$^1$H NMR (DMSO-d₆, 300 MHz) δ 8.84 (br s, 2H), 8.46 (d, 2H, J=1.7 Hz), 7.67-7.58 (m, 4H), 4.43-4.30 (m, 2H), 4.18 (br s, 1H), 3.18 (br s, 4H), 2.93 (br s, 6H).
Analysis for C₁₉H₂₁Br₂N₃O. 2CF₃CO₂H. 0.13Et₂O:
Calculated: C, 40.05; H, 3.46; N, 5.97;
Found: C, 40.43; H, 3.85; N, 6.33%.

Example 6

(±)-1-(4-Benzyl-piperazin-1-yl)-3-(3,6-dibromo-carbazol-9-yl)-propan-2-ol

The same method as employed in the preparation of Example 1 but starting from 3,6-dibromo-9H-carbazole and sodium hydride gives after flash chromatography the title compound as a white foam in a 66% yield. M.p.: 70-75° C.
Analysis for C₂₆H₂₇Br₂N₃O:
Calculated: C, 56.03; H, 4.88; N, 7.54;
Found: C, 55.81; H, 4.97; N, 7.36%.

Example 7

(±)-1-(4-Benzyl-piperazin-1-yl)-3-carbazol-9-yl-propan-2-ol

The same method as employed in the preparation of Example 1 but starting from 9H-carbazole gives the title compound as white crystals in a 66% yield.
M.p.: 205-210° C. (decomposition).
Analysis for C₂₆H₂₉N₃O. 2HCl. 0.4H₂O. 0.13EtOAc:
Calculated: C, 64.86; H, 6.74; N, 8.56; Cl, 14.44;
Found: C, 64.74; H, 6.83; N, 8.42; Cl, 14.54%.

Example 8

(±)-4-[3-(3-Bromo-carbazol-9-yl)-2-hydroxy-propyl]-piperazine-1-carboxylic tert-butyl ester The same method as employed in the preparation of Example 1 but starting from 3-bromo-9H-carbazole (prepared according to the procedure of Smith, K. et al *Tetrahedron* 1992, 48(36); pp 7474-7488), (±)-4-oxiranylmethyl-piperazine-1-carboxylic acid tert-butyl ester and sodium hydride gives after flash chromatography the title compound as a pale yellow foam in a 62% yield. M.p.: 65-75° C.
$^1$H NMR (CDCl₃, 300 MHz) δ 8.16 (d, 1H, J=1.9 Hz), 7.99 (d, 1H, J=7.8 Hz), 7.52 (dd, 1H, J=8.7, 1.9 Hz), 7.47 (m, 1H), 7.36 (d, 1H, J=8.7 Hz), 7.25 (m, 2H), 4.33 (m, 2H), 4.20 (m, 1H), 3.38 (br s, 5H), 2.52 (m, 2H), 2.46 (d, 2H, J=6.7 Hz), 2.32 (m, 2H), 1.44 (s, 9H).

Example 9

(±)-1-(3-Bromocarbazol-9-yl)-3-piperazin-1-yl-propan-2-ol

The same method as employed in the preparation of Example 3 but starting from (±)-4-[3-(3-bromocarbazol-9-yl)-2-hydroxy-propyl]-piperazine-1-carboxylic tert-butyl ester gives the title compound as a white solid in a 63% yield. M.p.: 230-235° C. (decomposition).
$^1$H NMR (DMSO-d6, 300 MHz) δ 8.39 (d, 1H, J=1.8 Hz), 8.18 (d, 1H, J=7.8 Hz), 7.70 (m, 2H), 7.50 (dd, 1H, J=8.7, 1.8 Hz), 7.45 (t, 1H, J=7.5 Hz), 7.22 (t, 1H, J=7.4 Hz), 4.40 (br s, 3H), 3.38 (br s, 10H).

Example 10

(±)-1-(4-Benzyl-piperazin-1-yl)-3-(2-hydroxy-carbazol-9-yl)-propan-2-ol

The same method as employed in the preparation of Example 1 but starting from 9H-carbazol-2-ol and 2 eq of n-BuLi (according to the procedure of Albanese, D. et al *Tetrahedron* 1995, 51(19), pp 5681-5688) gives after flash chromatography and recrystallization from EtOH the title compound as a beige solid in a 30% yield.
M.p.: 202° C.
$^1$H NMR (DMSO-d6, 300 MHz) δ 9.42 (s, 1H), 7.91 (d, 1H, J=7.5 Hz), 7.84 (d, 1H, J=8.4 Hz), 7.48 (d, 1H, J=8.2 Hz), 7.34-7.20 (m, 6H), 7.08 (t, 1H, J=7.1 Hz), 6.89 (d, 1H, J=1.9 Hz), 6.65 (dd, 1H, J=8.3, 2.0 Hz), 4.89 (d, 1H, J=4.9 Hz), 4.32 (dd, 1H, J=14.4, 3.6 Hz), 4.15-4.0 (m, 2H), 3.31 (s, 2H), 3.02-2.34 (m, 10H).

Example 11

(S)-4-[3-(3,6-Dibromocarbazol-9-yl)-2-hydroxy-propyl]-piperazine-1-carboxylic tert-butyl ester The same method as employed in the preparation of Example 1 but starting from 3,6-dibromo-9H-carbazole, Intermediate 2 and sodium hydride gives the title compound as a white foam in a 61% yield. M.p.: 90-100° C.
$^1$H NMR (CDCl₃, 300 MHz) δ 8.11 (d, 2H, J=1.9 Hz), 7.54 (dd, 2H, J=8.7, 1.9 Hz), 7.33 (d, 2H, J=8.7 Hz), 4.38-4.22 (m, 3H), 3.41 (br s, 4H), 2.54 (br s, 2H), 2.43-2.33 (m, 4H), 1.41 (s, 9H).

Example 12

(R)-4-[3-(3,6-Dibromocarbazol-9-yl)-2-hydroxy-propyl]-piperazine-1-carboxylic tert-butyl ester The same method as employed in the preparation of Example 1 but starting from 3,6-dibromo-9H-carbazole, Intermediate 3 and sodium hydride gives the title compound as a white foam in a 62% yield. M.p.: 90-100° C.

$^1$H NMR (CDCl$_3$, 300 MHz) δ 8.11 (d, 2H, J=1.9 Hz), 7.54 (dd, 2H, J=8.7, 1.9 Hz), 7.33 (d, 2H, J=8.7 Hz), 4.38-4.22 (m, 3H), 3.41 (br s, 4H), 2.54 (br s, 2H), 2.43-2.33 (m, 4H), 1.41 (s, 9H).

98% ee (ChiralPak AD column, rt, isohexane:EtOH:TEA (90:10:0.1), 240 nM, 1 mL/min).

Example 13

(S)-4-[3-(3-Bromo-carbazol-9-yl)-2-hydroxy-propyl]-piperazine-1-carboxylic tert-butyl ester The same method as employed in the preparation of Example 1 but starting from 3-bromo-9H-carbazole, Intermediate 2 and sodium hydride gives the title compound as a white foam in a 61% yield. M.p.: 75-85° C.

$^1$H NMR (CDCl$_3$, 300 MHz) δ 8.16 (d, 1H, J=1.8 Hz), 8.02 (d, 1H, J=7.0 Hz), 7.52 (dd, 1H, J=8.7, 1.9 Hz), 7.46 (m, 2H), 7.44 (d, 1H, J=8.7 Hz), 7.3 (m, 1H), 4.39-4.24 (m, 3H), 3.41 (br s, 4H), 2.54 (br s, 2H), 2.47-2.34 (m, 4H), 1.41 (s, 9H).

96% ee (ChiralPak AD column, rt, isohexane:EtOH:TEA (90:10:0.1), 240 nM, 1 mL/min).

Example 14

(R)-4-[3-(3-Bromo-carbazol-9-yl)-2-hydroxy-propyl]-piperazine-1-carboxylic tert-butyl ester The same method as employed in the preparation of Example 1 but starting from 3-bromo-9H-carbazole, Intermediate 3 and sodium hydride gives the title compound as a white foam in a 64% yield. M.p.: 75-85° C.

$^1$H NMR (CDCl$_3$, 300 MHz) δ 8.16 (d, 1H, J=1.8 Hz), 8.02 (d, 1H, J=7.0 Hz), 7.52 (dd, 1H, J=8.7, 1.9 Hz), 7.46 (m, 2H), 7.44 (d, 1H, J=8.7 Hz), 7.3 (m, 1H), 4.39-4.24 (m, 3H), 3.41 (br s, 4H), 2.54 (br s, 2H), 2.47-2.34 (m, 4H), 1.41 (s, 9H).

99% ee (ChiralPak AD column, rt, isohexane:EtOH:TEA (90:10:0.1), 240 nM, 1 mL/min).

Example 15

(S)-1-(3,6-Dibromocarbazol-9-yl)-3-piperazin-1-yl-propan-2-ol

The same method as employed in the preparation of Example 3 but starting from (S)-4-[3-(3,6-dibromocarbazol-9-yl)-2-hydroxy-propyl]-piperazine-1-carboxylic tert-butyl ester gives the title compound as a white solid in a 98% yield. M.p.: 304-305° C.

$^1$H NMR (DMSO-d$_6$, 300 MHz) δ 11.0 (br s, 1H), 9.56 (br s, 2H), 8.46 (d, 2H, J=1.9 Hz), 7.72 (d, 2H, J=8.8 Hz), 7.60 (dd, 2H, J=8.8, 1.9 Hz), 5.92 (br s, 1H), 4.40 (br s, 3H), 3.56-3.37 (m, 10H).

96% ee (ChiralPak AD column, rt, isohexane:EtOH:TEA (90:10:0.1), 240 nM, 1 mL/min).

Example 16

(R)-1-(3,6-Dibromocarbazol-9-yl)-3-piperazin-1-yl-propan-2-ol

The same method as employed in the preparation of Example 3 but starting from (R)-4-[3-(3,6-dibromocarbazol-9-yl)-2-hydroxy-propyl]-piperazine-1-carboxylic tert-butyl ester gives the title compound as a white solid in a 99% yield. M.p.: 303-304° C.

$^1$H NMR (DMSO-d6, 300 MHz) δ 11.0 (br s, 1H), 9.56 (br s, 2H), 8.46 (d, 2H, J=1.9 Hz), 7.72 (d, 2H, J=8.8 Hz), 7.60 (dd, 2H, J=8.8, 1.9 Hz), 5.92 (br s, 1H), 4.40 (br s, 3H), 3.56-3.37 (m, 10H).

98% ee (ChiralPak AD column, rt, isohexane:EtOH:TEA (90:10:0.1), 240 nM, 1 mL/min).

Example 17

(S)-1-(3-Bromocarbazol-9-yl)-3-piperazin-1-yl-propan-2-ol

The same method as employed in the preparation of Example 3 but starting from (S)-4-[3-(3-bromocarbazol-9-yl)-2-hydroxy-propyl]-piperazine-1-carboxylic tert-butyl ester gives the title compound as a white solid in a 97% yield. M.p.: 77° C. (decomposition).

$^1$H NMR (DMSO-d$_6$, 300 MHz) δ 10.96 (br s, 1H), 9.59 (br s, 2H), 8.39 (d, 1H, J=1.7 Hz), 8.20 (d, 1H, J=7.7 Hz), 7.70 (m, 2H), 7.57 (dd, 1H, J=8.7, 1.7 Hz), 7.47 (t, 1H, J=7.4 Hz), 7.22 (t, 1H, J=7.3 Hz), 5.91 (br s, 1H), 4.41 (br s, 3H), 3.54-3.36 (m, 10H).

96% ee (ChiralPak AD column, rt, isohexane:EtOH:TEA (80:20:0.1), 266 nM, 1 mL/min).

Example 18

(R)-1-(3-Bromocarbazol-9-yl)-3-piperazin-1-yl-propan-2-ol

The same method as employed in the preparation of Example 3 but starting from (R)-4-[3-(3-bromocarbazol-9-yl)-2-hydroxy-propyl]-piperazine-1-carboxylic tert-butyl ester gives the title compound as a white solid in a 97% yield. M.p.: 70-74° C.

$^1$H NMR (DMSO-d$_6$, 300 MHz) δ 10.96 (br s, 1H), 9.59 (br s, 2H), 8.39 (d, 1H, J=1.7 Hz), 8.20 (d, 1H, J=7.7 Hz), 7.70 (m, 2H), 7.57 (dd, 1H, J=8.7, 1.7 Hz), 7.47 (t, 1H, J=7.4 Hz), 7.22 (t, 1H, J=7.3 Hz), 5.91 (br s, 1H), 4.41 (br s, 3H), 3.54-3.36 (m, 10H).

98% ee (ChiralPak AD column, rt, isohexane:EtOH:TEA (80:20:0.1), 266 nM, 1 mL/min).

Example 19

(±)-1-[(3,4-Dichloro-phenyl)-piperazin-1-yl]-3-(2-methyl-carbazol-9-yl)-propan-2-ol The same method as employed in the preparation of Example 1 but starting from Intermediate 4 gives the title compound as a pale pink powder in a 20% yield.
M.p.: 140° C.
Analysis for $C_{26}H_{27}N_3OCl_2$. 2HCl. 0.9H$_2$O:
Calculated: C, 56.01; H, 5.57; N, 7.54;
Found: C, 56.02; H, 5.35; N, 7.67%.

Example 20

(±)-1-[(3,4-Dichloro-phenyl)-piperazin-1-yl]-3-(carbazol-9-yl)-propan-2-ol

The same method as employed in the preparation of Example 1 but starting from 9H-carbazole and Intermediate 4 gives the title compound as white crystals in a 26% yield. M.p.: 244° C. (decomposition).
Analysis for $C_{25}H_{25}N_3OCl_2$. HCl. 1.45$H_2O$. 0.16DCM:
Calculated: C, 56.96; H, 5.55; N, 7.92;
Found: C, 56.60; H, 5.12; N, 7.89%.

Example 21

(±)-1-(4-Benzo[1,3]dioxol-5ylmethyl-piperazin-1-yl)-4-carbazol-9-yl)-propan-2-ol The same method as employed in the preparation of Example 1 but starting from 9H-carbazole and Intermediate 5 gives the title compound as a beige solid in a 27% yield. M.p.: 170° C. (decomposition).
Analysis for $C_{27}H_{29}N_3O_3$. 1.9HCl. 0.7$H_2O$:
Calculated: C, 61.51; H, 6.21; N, 7.97;
Found: C, 61.38; H, 6.50; N, 7.88%.

Example 22

(±)-1-Carbazol-9-yl-3-[4-(4-fluoro-benzyl)-piperazin-1-yl]-propan-2-ol

The same method as employed in the preparation of Example 1 but starting from 9H-carbazole and Intermediate 6 gives the title compound as a beige solid in a 35% yield. M.p.: 251° C. (decomposition).
Analysis for $C_{26}H_{28}FN_3O$. 2HCl. $H_2O$:
Calculated: C, 61.42; H, 6.34; N, 8.26;
Found: C, 61.21; H, 6.42; N, 8.18%.

Example 23

(±)-1-(3,6-Dibromo-carbazol-9-yl)-3-[4-(4-fluoro-benzyl)-piperazin-1-yl]-propan-2-ol The same method as employed in the preparation of Example 1 but starting from 3,6-dibromo-9H-carbazole, Intermediate 6 and sodium hydride gives the title compound as white crystals in a 60% yield. M.p.: 297° C. (decomposition).
Analysis for $C_{26}H_{26}Br_2FN_3O$. 2HCl:
Calculated: C, 48.17; H, 4.35; N, 6.48;
Found: C, 47.91; H, 4.55; N, 6.21%.

Example 24

(±)-1-[4-(4-Fluoro-benzyl)-piperazin-1-yl]-3-(3-phenyl-carbazol-9-yl)-propan-2-ol The same method as employed in the preparation of Example 1 but starting 9H-carbazole, Intermediate 7 and Intermediate 6 gives the title compound as white crystals in a 40% yield. M.p.: 188° C.
Analysis for $C_{32}H_{32}FN_3O$. 2HCl. 2$H_2O$:
Calculated: C, 63.78; H, 6.36; N, 6.97;
Found: C, 63.76; H, 6.23; N, 7.02%.

Example 25

(±)-9-(2-Hydroxy-3-piperazin-1-yl-propyl)-carbazole-3,6-dicarbonitrile

The same method as employed in the preparation of Example 3 but starting from (±)-4-[3-(3,6-dicyanocarbazol-9-yl)-2-hydroxy-propyl]-piperazine-1-carboxylic tert-butyl ester gives the title compound as a white solid in a 63% yield. M.p.: 295° C. (decomposition).
Analysis for $C_{21}H_{21}N_5O$. 2HCl. 1.8$H_2O$:
Calculated: C, 54.27; H, 5.77; N, 15.07;
Found: C, 54.25; H, 6.08; N, 14.98%.
4-[3-(3,6-Dicyanocarbazol-9-yl)-2-hydroxy-propyl]piperazine-1-carboxylic tert-butyl ester (0.38 g, 52%) is obtained as a yellow solid using the same method as employed in the preparation of Example 1 but starting from 4-oxiranylmethyl-piperazine-1-carboxylic acid tert-butyl ester (0.20 g, 0.83 mmol), 9H-carbazole-3,6-dicarbonitrile (0.20 g, 0.92 mmol) (prepared according to the procedure of Patrick, D. A. et al *Eur. J. Med. Chem.* 1997, 32, pp 781-793) and sodium hydride (40 mg, 0.92 mmol).
$^1$H NMR (CDCl$_3$, 300 MHz) δ 8.33 (d, 2H, J=1.3 Hz), 7.71 (dd, 2H, J=8.6, 1.3 Hz), 7.30 (d, 2H, J=8.6 Hz), 4.42 (dd, 1H, J=15.1, 3.1 Hz), 4.34 (dd, 1H, J=15.1, 6.3 Hz), 4.18 (br s, 1H), 3.56 (br s, 1H), 3.37 (m, 4H), 2.56-2.36 (m, 6H), 1.44 (s, 9H).

Example 26

(±)-1-(3-Nitrocarbazol-9-yl)-3-piperazin-1-yl-propan-2-ol

The same method as employed in the preparation of Example 3 but starting from (±)-4-[3-(3-nitrocarbazol-9-yl)-2-hydroxy-propyl]-piperazine-1-carboxylic tert-butyl ester gives the title compound as a yellow solid in a 95% yield. M.p.: 112° C. (decomposition).
$^1$H NMR (DMSO-d$_6$:D$_2$O (700:40), 300 MHz) δ 9.17 (d, 1H, J=2.1 Hz), 8.40 (d, 1H, J=7.7 Hz), 8.34 (dd, 1H, J=9.1, 2.1 Hz), 7.84 (d, 1H, J=9.1 Hz), 7.80 (d, 1H, J=8.3 Hz), 7.57 (t, 1H, J=7.6 Hz), 7.33 (t, 1H, J=7.5 Hz), 4.50 (m, 2H), 4.36 (br s, 1H), 3.47-3.08 (m, 10H).
(±)-4-[3-(3-Nitrocarbazol-9-yl)-2-hydroxy-propyl]-piperazine-1-carboxylic tert-butyl ester (0.135 g, 43%) is obtained as a yellow foam using the same method as employed in the preparation of Example 1 but starting from 3-nitro-9H-carbazole (0.218 g, 1.03 mmol) (prepared according to the procedure of Kyziol, J. B. et al *Tetrahedron* 1984, 40(10), pp 1857-1861), (±)-4-oxiranylmethyl-piperazine-1-carboxylic acid tert-butyl ester (0.166 g, 0.685 mmol) and sodium hydride (0.045 g, 1.027 mmol).
$^1$H NMR (CDCl$_3$, 300 MHz) δ 8.93 (d, 1H, J=3.1 Hz), 8.34 (dd, 1H, J=9.1, 2.7 Hz), 8.10 (d, 1H, J=7.9), 7.53-7.49 (m, 3H), 7.30 (ddd, 1H, J=7.8, 6.6, 1.6 Hz), 4.43 (dd, 1H, J=15.1, 4.3 Hz), 4.34 (dd, 1H, J=15.1, 5.8 Hz), 4.20 (m, 1H), 3.37 (m, 4H), 2.54 (m, 2H), 2.37 (m, 2H), 2.30 (m, 2H), 1.44 (s, 9H).
Alternatively, the same method as employed in the preparation of Example 73 could be employed, but starting from Intermediate 19 and piperazine in EtOH gives the hydrochloride of the title compound as a yellow compound in a one step procedure in 98% yield.
M.p.: 112° C.
$^1$H NMR (DMSO-d6, 300 MHz) δ 9.17 (d, 1H, J=2.1 Hz), 8.40 (d, 1H, J=7.7 Hz), 8.34 (dd, 1H, J=9.1, 2.1 Hz), 7.84 (d, 1H, J=9.1 Hz), 7.80 (d, 1H, J=8.3 Hz), 7.57 (t, 1H, J=7.6 Hz), 7.33 (t, 1H, J=7.5 Hz), 4.50 (m, 2H), 4.36 (br s, 1H), 3.47-3.08 (m, 10H).

Example 27

(±)-1-(3-Phenylcarbazol-9-yl)-3-piperazin-1-yl-propan-2-ol

The same method as employed in the preparation of Example 3 but starting from (±)-4-[3-(3-phenylcarbazol-9-yl)-2-hydroxy-propyl]-piperazine-1-carboxylic tert-butyl ester gives the title compound as a white solid in a 78% yield. M.p.: 120° C.
$^1$H NMR (DMSO-d$_6$:D$_2$O (700:40), 300 MHz) δ 8.46 (s, 1H), 8.24 (d, 1H, J=7.7 Hz), 7.78-7.76 (m, 4H), 7.70 (d, 1H, J=8.2 Hz), 7.48 (m, 3H), 7.32 (t, 1H, J=7.3 Hz), 7.22 (t, 1H, J=7.5 Hz), 4.40 (m, 3H), 3.42-3.31 (m, 10H).
(±)-4-[3-(3-Phenylcarbazol-9-yl)-2-hydroxy-propyl]piperazine-1-carboxylic tert-butyl ester (0.135 g, 35%) is obtained as a white foam using the same method as employed in the preparation of Example 1 but starting from Intermediate 7 (0.182 g, 0.75 mmol) and (±)-4-oxiranylmethyl-piperazine-1-carboxylic acid tert-butyl ester (0.165 g, 0.68 mmol).
$^1$H NMR (CDCl$_3$, 300 MHz) δ 8.30 (d, 1H, J=1.7 Hz), 8.12 (d, 1H, J=7.7 Hz), 7.71 (m, 3H), 7.53-726 (m, 7H), 4.38 (m, 2H), 4.22 (m, 1H), 3.52 (br s, 4H), 2.54-2.42 (m, 4H), 2.30 (m, 2H), 1.44 (s, 9H).

Example 28

(±)-1-(2-Hydroxycarbazol-9-yl)-3-piperazin-1-yl-propan-2-ol

The same method as employed in the preparation of Example 3 but starting from (±)-4-[3-(2-hydroxycarbazol-9-yl)-2-hydroxy-propyl]-piperazine-1-carboxylic tert-butyl ester gives the title compound as a beige solid in a 10% yield.
$^1$H NMR (DMSO-d$_6$, 300 MHz) δ 9.50 (br s, 1H), 7.65 (d, 1H, J=7.4 Hz), 7.86 (d, 1H, J=8.3 Hz), 7.55 (d, 1H, J=8.2 Hz), 7.30 (t, 1H, J=7.2 Hz), 7.12 (t, 1H, J=7.4 Hz), 6.96 (s, 1H), 6.68 (dd, 1H, J=8.3, 1.6 Hz), 4.27 (br s, 3H), 2.49 (m, 10H).
(±)-4-[3-(2-Hydroxycarbazol-9-yl)-2-hydroxy-propyl]-piperazine-1-carboxylic tert-butyl ester is obtained as an oil which is used without purification using the same method as employed in the preparation of Example 1 but starting from 2-hydroxy-9H-carbazole (0.182 g, 0.75 mmol), 2 eq of n-BuLi (2.2 mL, 1.6 M in Hexanes) (according to the procedure of Albanese, D. et al *Tetrahedron* 1995, 51(19), pp 5681-5688) and 4-oxiranyl-methyl-pipera-zine-1-carboxylic acid tert-butyl ester (0.210 g, 0.87 mmol).

Example 29

(±)-1-(3,6-Diphenylcarbazol-9-yl)-3-piperazin-1-yl-propan-2-ol

The same method as employed in the preparation of Example 3 but starting from 4-[3-(3,6-diphenylcarbazol-9-yl-2-hydroxy-propyl]-piperazine-1-carboxylic tert-butyl ester gives the title compound as a white solid in a 88% yield. M.p.: 270-288° C.
$^1$H NMR (DMSO-d$_6$, 300 MHz) δ 8.39 (s, 2H), 7.56 (m, 8H), 7.27 (m, 4H), 7.11 (t, 2H, J=7.3 Hz), 4.25 (m, 3H), 3.30 (m, 10H).
4-[3-(3,6-Diphenylcarbazol-9-yl)-2-hydroxy-propyl]-piperazine-1-carboxylic tert-butyl ester (0.110 g, 60%) is obtained as a white solid using the same method as employed in the preparation of Example 1 but starting from Intermediate 8 (0.114 g, 0.36 mmol), (±)-4-oxiranylmethyl-piperazine-1-carboxylic acid tert-butyl ester (0.079 g, 0.326 mmol) and sodium hydride (0.017 g, 0.39 mmol).
$^1$H NMR (CDCl$_3$, 300 MHz) δ 8.32 (d, 2H, J=1.2 Hz), 7.73-7.69 (m, 6H), 7.54-7.27 (m, 8H), 4.43 (br s, 2H), 4.11 (s, 1H), 3.34 (br s, 4H), 2.45 (br s, 4H), 2.02 (br s, 2H), 1.44 (s, 9H).

Example 30

(±)-1-(3,6-Dibromo-carbazol-9-yl)-3-[4-(3-phenyl-propyl)-piperazin-1-yl]-propan-2-ol The same method as employed in the preparation of Example 1 but starting from 3,6-dibromo-9H-carbazole, Intermediate 9 and sodium hydride gives the title compound as a white solid in a 35% yield. M.p.: 255° C.
Analysis for C$_{28}$H$_{31}$BrN$_3$O. 2HCl. 0.7H$_2$O:
Calculated: C, 50.13; H, 5.17; N, 6.26;
Found: C, 50.09; H, 5.54; N, 5.92%.

Example 31

(±)-1-Carbazol-9-yl-3-[4-(3-phenyl-propyl)-piperazin-1-yl]-propan-2-ol

The same method as employed in the preparation of Example 1 but starting from 9H-carbazole, Intermediate 9 and sodium hydride gives the title compound as a white solid in a 35% yield. M.p.: 265° C.
Analysis for C$_{28}$H$_{33}$N$_3$O. 2HCl. 0.5H$_2$O:
Calculated: C, 66.01; H, 7.12; N, 8.25;
Found: C, 66.11; H, 7.26; N, 8.27%.

Example 32

(±)-3,6-Dibromo-9-(2-fluoro-3-piperazin-1-yl-propyl)-carbazole

The same method as employed in the preparation of Example 3 but starting from (±)-4-[3-(3,6-dibromo-carbazol-9-yl)-2-fluoro-propyl]-piperazine-1-carboxylic tert-butyl ester gives the title compound as a white solid in a 61% yield. M.p.: 270° C.
Analysis for C$_{19}$H$_{20}$Br$_2$FN$_3$. 2HCl. 0.5H$_2$O:
Calculated: C, 41.41; H, 4.21; N, 7.62;
Found: C, 41.29; H, 4.17; N, 7.51%.
(±)-4-[3-(3,6-Dibromo-carbazol-9-yl)-2-fluoro-propyl]-piperazine-1-carboxylic tert-butyl ester (0.05 g, 80%) is obtained as a colorless oil from the reaction of Example 4 (0.100 g, 0.176 mmol) and DAST (100 µL, 0.763 mmol) in DCM (4 mL) at 0° C. Quenching with a saturated aqueous solution of NaHCO$_3$, extraction with DCM, drying over MgSO$_4$, flash chromatography on a 2×15 cm$^2$ column of SiO$_2$ using DCM:MeOH (100:1.5) as eluting solvent and concentration in vacuo gives the above compound.
$^1$H NMR (CDCl$_3$, 300 MHz) δ 8.05 (d, 2H, J=1.9 Hz), 7.50 (dd, 2H, J=8.7, 1.9 Hz), 7.29 (d, 2H, J=8.7 Hz), 4.93 (dm, 1H, J=47.3 Hz), 4.85 (m, 0.5H), 4.53-4.46 (m, 2H), 3.45 (m, 4H), 2.54 (m, 2H), 2.41 (br s, 4H), 1.44 (s, 9H).

Example 33

(±)-1-(3-Amino-carbazol-9-yl)-3-piperazin-1-yl-propan-2-ol

The same method as employed in the preparation of Example 3 but starting from (±)-4-[3-(3-amino-carbazol-9- yl)-2-hydroxy-propyl]-piperazine-1-carboxylic tert-butyl ester gives after the title compound as a beige solid in a 61% yield. M.p.: 220° C.

$^1$H NMR (DMSO-d$_6$, 300 MHz) δ 10.49 (br s, 2H), 9.79 (br s, 1H), 8.18 (d, 1H, J=7.7 Hz), 8.11 (d, 1H, J=1.7 Hz), 7.83 (d, 1H, J=8.7 Hz), 7.75 (d, 1H, J=8.3 Hz), 7.50 (m, 2H), 7.27 (m, 2H), 7.06 (s, 1H), 5.88 (br s, 1H), 4.44 (br s, 3H), 3.49-3.15 (m, 10H).

(±)-4-[3-(3-Amino-carbazol-9-yl)-2-hydroxy-propyl]-piperazine-1-carboxylic tert-butyl ester is obtained from the reduction of (±)-4-[3-(3-nitrocarbazol-9-yl)-2-hydroxy-propyl]-piperazine-1-carboxylic tert-butyl ester (0.100 g, 0.22 mmol) using SnCl$_2$.H$_2$O (0.248 g, 1.10 mmol) in EtOH (2 mL) at 70° C. for 2 hours. Addition of an aqueous saturated solution of NaHCO$_3$ until pH=7-8, extraction with EtOAc, drying over MgSO$_4$ and concentration in vacuo gives a brown oil. Purification via flash chromatography on a 2×15 cm$^2$ column (SiO$_2$, DCM:MeOH (97:3)) gives the above compound as an orange oil in a 58% yield.

$^1$H NMR (CDCl$_3$, 300 MHz) δ 7.97 (d, 1H, J=7.7 Hz), 7.42-7.38 (m, 3H), 7.27 (d, 1H, J=8.5 Hz), 7.15 (m, 1H), 6.88 (dd, 1H, J=8.5, 2.2 Hz), 4.31 (m, 2H), 4.20 (m, 1H), 3.37 (m, 4H), 2.55-2.40 (m, 4H), 2.27 (m, 2H), 1.41 (s, 9H).

Example 34

(±)-N-[9-(2-Hydroxy-3-piperazin-1-yl-propyl)-carbazol-3-yl]-acetamide

The same method as employed in the preparation of Example 3 but starting from (±)-4-[3-(3-acetylamino-carbazol-9-yl)-2-hydroxy-propyl]-piperazine-1-carboxylic tert-butyl ester gives the title compound as a pale grey powder in a 63% yield. M.p.>180° C. (decomposition).

$^1$H NMR (DMSO-d$_6$:D$_2$O (700:40), 300 MHz) δ 8.34 (d, 1H, J=1.8 Hz), 8.03 (d, 1H, J=7.7 Hz), 7.66 (d, 1H, J=8.3 Hz), 7.62 (d, 1H, J=8.8 Hz), 7.55 (dd, 1H, J=8.8, 1.8 Hz), 7.39 (t, 1H, J=7.5 Hz), 7.17 (t, 1H, J=7.5 Hz), 4.49 (m, 1H), 4.37 (m, 2H), 3.64-3.28 (m, 10H), 2.06 (s, 3H).

(±)-4-[3-(3-Acetylamino-carbazol-9-yl)-2-hydroxy-propyl]-piperazine-1-carboxylic tert-butyl ester is obtained from the reaction of (±)-4-[3-(3-amino-carbazol-9-yl)-2-hydroxy-propyl]-piperazine-1-carboxylic acid tert-butyl ester (0.139 g, 0.33 mmol) and acetic acid (21 µL, 0.33 mmol) in the presence of HOBt (0.056 g, 0.36 mmol), EDCI.HCl (0.069 g, 0.36 mmol), TEA (50 µL, 0.33 mmol) in DCM. Standard quenching and work-up gives the above compound as a brown foam.

$^1$H NMR (CDCl$_3$, 300 MHz) δ 8.16 (d, 1H, J=1.9 Hz), 7.90 (m, 2H), 7.37 (m, 3H), 7.27 (d, 1H, J=8.7 Hz), 7.13 (m, 1H), 4.30-4.06 (m, 3H), 3.32 (m, 4H), 2.43 (m, 2H), 2.34 (m, 2H), 2.22 (m, 2H), 2.13 (s, 3H), 1.42 (s, 9H).

Example 35

(±)-1-[4-(3-Carbazol-9-yl-2-hydroxy-propyl)-piperazin-1-yl]-2-phenoxy-ethanone

To a solution of Example 3 (0.200 g, 0.6 mmol) in 25 mL of DCM are added TEA (90 µL, 1 eq), EDCI (0.124 g, 1 eq), HOBT (0.087 g, 1 eq) and phenoxy-acetic acid (0.099 g, 1 eq). After 12 hr of stirring at rt the reaction is judged to be complete by tlc monitoring (SiO$_2$, DCM:MeOH (95:5)) and is quenched with 10 mL of water. The reaction mixture is extracted with DCM, washed with brine (5 mL), dried over MgSO$_4$ and concentrated in vacuo. Flash chromatography on a 2.5×12 cm$^2$ column of silica gel using DCM:MeOH (95:5) as eluting solvent and removal of the solvent in vacuo gives the title compound as a white foam. Slow addition of HCl (5 mL, 1M in Et$_2$O) into a solution of the above compound in DCM (2 mL) gives the hydrochloride salt of the title compound (0.39 g) as a beige powder in a 66% yield.

M.p.: 130° C.

$^1$H NMR (CDCl$_3$, 300 MHz) δ 10.22 (br s, 1H), 8.14 (d, 2H, J=8.2 Hz), 7.68 (d, 2H, J=8.2 Hz), 7.46 (tr, 2H, J=7.2 Hz), 7.42-7.18 (m, 4H), 6.95-6.89 (m, 3H), 6.00 (br s, 1H), 4.83 (s, 2H), 4.4-3.9 (m, 5H), 3.7-3.1 (m, 8H).

Example 36

(±)-1-[4-(3-Carbazol-9-yl-2-hydroxy-propyl)-piperazin-1-yl]-1-phenyl-methanone

The same method as employed in the preparation of Example 35 but starting from benzoic acid gives the title compound as a white powder in a 56% yield. M.p.: 153° C.

Analysis for C$_{26}$H$_{27}$N$_3$O$_2$. HCl. 1.3H$_2$O:

Calculated: C, 65.97; H, 6.51; N, 8.88;

Found: C, 65.96; H, 6.35; N, 8.86%.

Example 37

(±)-1-[4-(3-Carbazol-9-yl-2-hydroxy-propyl)-piperazin-1-yl]-2-(4-hydroxy-phenoxy)-ethanone The same method as employed in the preparation of Example 35 but starting from 4-hydroxyphenoxy acetic acid gives the title compound as a white powder in a 27% yield. M.p.: 155° C.

$^1$H NMR (DMSO-d$_6$, 300 MHz) δ 10.25 (br s, 1H), 9.96 (s, 1H), 8.14 (d, 2H, J=7.7 Hz), 7.67 (d, 2H, J=8.2 Hz), 7.47-7.42 (m, 2H), 7.29-7.18 (m, 4H), 6.80 (d, 2H, J=8.6 Hz), 6.01 (br s, 1H), 4.48 (m, 3H), 4.11 (br s, 2H), 3.52-3.10 (m, 10H).

Example 38

(±)-1-[4-(3-Carbazol-9-yl-2-hydroxy-propyl)-piperazin-1-yl]-1-(4-hydroxy-phenyl)-methanone The same method as employed in the preparation of Example 35 but starting from 4-hydroxybenzoic acid gives the title compound as a white powder in a 68% yield.

M.p.: 184° C.

$^1$H NMR (DMSO-d$_6$, 300 MHz) δ 9.96 (br s, 1H), 8.89 (s, 1H), 8.09 (d, 2H, J=7.7 Hz), 7.61 (d, 2H, J=8.2 Hz), 7.43-7.37 (m, 2H), 7.15 (m, 2H), 6.69-6.57 (m, 4H), 5.95 (br s, 1H), 4.63 (s, 1H), 4.30 (br m, 3H), 3.47-3.04 (m, 10H).

Example 39

(±)-1-[4-(3-Carbazol-9-yl-2-hydroxy-propyl)-piperazin-1-yl]-1-(4-fluorophenyl)-methanone The same method as employed in the preparation of Example 35 but starting from 4-fluoro-benzoic acid gives the title compound as a white powder in an 86% yield.

M.p.: 70-80° C.

Analysis for C$_{26}$H$_{26}$N$_3$O$_2$. HCl. 0.5H$_2$O. 0.17Et$_2$O:

Calculated: C, 65.46; H, 6.11; N, 8.58;

Found: C, 65.27; H, 6.38; N, 8.41%.

Example 40

(±)-1-(4-Benzenesulfonyl-piperazin-1-yl)-3-carbazol-9-yl-propan-2-ol

To a solution of Example 3 (0.200 g, 0.6 mmol) in 20 mL of DMF were added TEA (100 µL, 1 eq) and benzene sulfonyl chloride (0.114 g, 1 eq). After 12 hr of stirring at rt the reaction is judged to be complete by tlc monitoring (SiO$_2$, DCM:MeOH (95:5)) and is concentrated in vacuo. The residue is taken up in DCM (10 mL), washed with brine (5 mL) and extracted. The combined organic layers were dried over MgSO$_4$ and concentrated in vacuo. Flash chromatography on a 2.5×12 cm$^2$ column of silica gel using DCM:MeOH (95:5) as eluting solvent and removal of the solvent in vacuo gives the title compound as a white powder. Slow addition of HCl (4 eq, 1M in Et$_2$O) into a solution of the above compound in DCM (2 mL) gives the hydrochloride salt of the title compound (0.39 g) as white crystals in a 92% yield. M.p.: 130° C.

Analysis for C$_{25}$H$_{27}$N$_3$O$_3$S. HCl. 0.5H$_2$O:
Calculated: C, 60.66; H, 5.90; N, 8.49;
Found: C, 60.53; H, 5.94; N, 8.34%.

Example 41

(±)-9-[3-(4-Benzyl-piperazin-1-yl)-2-methoxy-propyl]-carbazole

To a solution of Example 7 (0.200 g, 0.50 mmol) in 5 mL of THF are added NaH (0.068 g, 1.56 mmol) and methyl iodide (125 µL, 2.0 mmol). After 2 hr of stirring at rt the reaction is judged to be complete by tlc monitoring (SiO$_2$, DCM:MeOH (100:3)) and is quenched with a saturated aqueous solution of Na$_2$CO$_3$ (5 mL). Extraction with DCM, drying over MgSO$_4$, concentration in vacuo, flash chromatography on a 2.5×12 cm$^2$ column of silica gel using DCM:MeOH (95:5) as eluting solvent and removal of the solvent in vacuo gives the title compound as an oil. Slow addition of HCl (4 eq, 1M in Et$_2$O) into a solution of the above compound in EtOH (2 mL) gives the hydrochloride salt of the title compound (0.39 g) as white crystals in a 60% yield. M.p.: 272° C.

$^1$H NMR (DMSO-d$_6$, 300 MHz) δ 8.14 (d, 2H, J=7.7 Hz), 7.67 (d, 2H, J=8.2 Hz), 7.60 (br s, 2H), 7.46 (m, 5H), 7.20 (tr, 2H, J=7.4 Hz), 4.40 (br s, 2H), 4.32 (br s, 3H), 3.75-3.10 (br m, 8H), 3.04 (s, 3H).

Example 42

(±)-1-(3,6-Dibromo-carbazol-9-yl)-3-piperazin-1-yl-propan-2-one

The same method as employed in the preparation of Example 3 but starting from (±)-4-[3-(3,6-dibromo-carbazol-9-yl)-2-oxo-propyl]-piperazine-1-carboxylic tert-butyl ester gives the title compound as a white solid in a 83% yield. M.p.: 175° C.

$^1$H NMR (DMSO-d$_6$, 300 MHz) δ 9.31 (br s, 2H), 8.48 (d, 2H, J=1.6 Hz), 7.59 (dd, 2H, J=8.8, 1.6 Hz), 7.54 (d, 2H, J=8.8 Hz), 5.52 (s, 2H), 4.18 (m, 2H), 3.25-3.13 (m, 8H).

(±)-4-[3-(3,6-Dibromocarbazol-9-yl)-2-oxo-propyl]-piperazine-1-carboxylic tert-butyl ester (0.0.38 g, 38%) is obtained as a colorless oil by Swern oxidation of Example 4 (0.100 g, 0.176 mmol) using oxalyl chloride (20 µL, 0.211 mmol), DMSO (31 µL, 0.44 mmol) and TEA (125 µL, 0.90 mmol) in DCM (1 mL) at −78° C.

$^1$H NMR (CDCl$_3$, 300 MHz) δ 8.09 (d, 2H, J=1.9 Hz), 7.51 (dd, 2H, J=8.7, 1.9 Hz), 7.10 (d, 2H, J=8.7 Hz), 4.99 (s, 2H), 3.39 (m, 4H), 3.03 (s, 2H), 2.30 (m, 4H), 1.43 (s, 9H).

Example 43

(±)-1-(3,6-Dibromo-carbazol-9-yl)-3-[4-(2-hydroxy-3-methylamino-propyl)-piperazin-1-yl]-propan-2-ol To (±)-1-(3,6-dibromo-carbazol-9-yl)-3-(4-oxiranylmethyl-piperazin-1-yl)-propan-2-ol (0.110 g, 0.21 mmol) is added methyl amine (3 mL, 2M in MeOH). The resulting mixture was stirred for 16 hr at rt. Concentration in vacuo, flash chromatography on a 2×14 cm$^2$ column of SiO$_2$ using (ACN:(aqueous NH$_4$OH-25%)) (5:1) as eluting solvent gives the title compound as a white foam in a 90% yield. M.p.: 65-75° C. Slow addition of HCl (1 mL, 1M in Et$_2$O) into a solution of the above compound in DCM (2 mL) gives the hydrochloride salt of the title compound (0.39 g) as a white solid in a 35% yield.

M.p.>200° C.

$^1$H NMR (DMSO-d$_6$, 300 MHz) δ 8.78 (br s, 2H), 8.41 (d, 2H, J=1.8 Hz), 7.66 (d, 2H, J=8.8 Hz), 7.54 (dd, 2H, J=8.8, 1.8 Hz), 4.36-2.83 (m, 18H), 2.43 (s, 3H).

(±)-1-(3,6-Dibromo-carbazol-9-yl)-3-(4-oxiranylmethyl-piperazin-1-yl)-propan-2-ol (0.118 g, 0.24 mmol) is obtained after chromatography on a 2×20 cm$^2$ column of SiO$_2$ using DCM:MeOH (97:3) as eluting solvent, as a white solid using the same method as employed in the preparation of Example 1 but starting from 3,6-dibromo-9H-carbazole (0.30 g, 0.92 mmol), (±)-1,4-bis-oxiranylmethyl-piperazine (prepared according to the procedure of Gerzon et al *J. Med. Pharm. Chem.* 1959, 1, p223) (0.20 g, 1.01 mmol) and sodium hydride.

$^1$H NMR (CDCl$_3$, 300 MHz) δ 8.02 (d, 2H, J=1.9 Hz), 7.50 (dd, 2H, J=8.7, 1.9 Hz), 7.25 (d, 2H, J=8.7 Hz), 4.22 (dd, 1H, J=14.9, 3.9 Hz), 4.13 (dd, 1H, J=14.9, 5.9 Hz), 4.05 (m, 1H), 3.70 (d, 1H, J=11.6 Hz), 3.00 (m, 1H), 2.71 (t, 1H, J=4.5 Hz), 2.65 (ddd, 1H, J=13.3, 7.4, 3.1 Hz), 2.61-2.26 (m, 11H), 2.14 (ddd, 1H, J=13.3, 8.6, 7.0 Hz).

Example 44

(±)-1-(3,6-Dibromo-carbazol-9-yl)-3-[4-(3-phenyl-1,2,4-thiadiazol-5-yl)-piperazin-1-yl]-propan-2-ol The same method as employed in the preparation of Example 1 but starting from 3,6-dibromo-9H-carbazole, Intermediate 10 and sodium hydride gives the title compound as white crystals in a 28% yield. M.p.: 196° C. (decomposition).

$^1$H NMR (DMSO-d$_6$+D$_2$O, 300 MHz) δ 8.22 (d, 2H, J=1.8 Hz), 7.85 (m, 2H), 7.44-7.36 (m, 5H), 7.23 (m, 2H), 4.17 (br s, 3H); 3.7 (br s, 2H), 3.38 (br s, 8H).

Example 45

(±)-1-4-Cyclohexylmethylpiperazin-1-yl)-3-(3,6-dibromo-carbazol-9-yl)-propan-2-ol The same method as employed in the preparation of Example 1 but starting from 3,6-dibromo-9H-carbazole, Intermediate 11 and sodium hydride and heating at 60° C. for 16 hours gives after flash chromatography the title compound as a white foam. Slow addition of HCl (1M in Et$_2$O) into a solution of the above compound in DCM gives the hydrochloride salt of the title compound as a beige solid in a 35% yield.

¹H NMR (DMSO-d₆+D₂O, 300 MHz) δ 8.45 (d, 2H, J=1.9 Hz), 7.68 (d, 2H, J=8.8 Hz), 7.60 (dd, 2H, J=8.7, 1.9 Hz), 4.4-4.3 (m, 3H), 3.6-3.0 (m, 11H), 2.9 (br s, 1H), 1.8-1.5 (m, 6H), 1.2-0.9 (m, 5H).
Mp: 280° C. (decomposition).
Analysis for $C_{26}H_{33}Br_2N_3O \cdot 2HCl \cdot 0.3 H_2O$:
Calculated: C, 48.67; H, 5.69; N, 6.55;
Found: C, 48.46; H, 5.98; N, 6.42%:

Example 46

(±)-1-[(4-Fluorophenyl)-piperazin-1-yl]-3-(3,6-dibromocarbazol-9-yl)-propan-2-ol The same method as employed in the preparation of Example 1 but starting from 3,6-dibromo-9H-carbazole, Intermediate 12 and sodium hydride and heating at 60° C. for 16 hours gives after flash chromatography the title compound as a yellow oil. Slow addition of HCl (1M in Et₂O) into a solution of the above compound in DCM gives the hydrochloride salt of the title compound as a camel-colored solid in a 54% yield.
¹H NMR (DMSO-d₆+D₂O, 300 MHz) δ 8.44 (d, 2H, J=1.7 Hz), 7.67-7.58 (m, 4H), 7.10-6.95 (m, 4H), 4.6-4.2 (m, 5H), 3.8-3.5 (m, 5H), 3.4-3.0 (m, 4H).
Mp: 230° C. (decomposition).
Analysis for $C_{25}H_{24}Br_2FN_3O \cdot 2HCl \cdot 0.5H_2O$:
Calculated: C, 46.68; H, 4.23; N, 6.53;
Found: C, 47.08; H, 4.67; N, 6.50%.

Example 47

(±)-1-(Carbazol-9-yl)-3-[4-(2-fluorobenzyl)piperazin-1-yl]propan-2-ol

A solution of Example 3 (0.05 g, 0.16 mmol) in 25 mL of TMOF under an argon atmosphere is treated with 2-fluorobenzaldehyde (0.06 g, 0.48 mmol) for 4 hours. Then sodium triacetoxy borohydride (0.103 g, 0.48 mmol) is added neat. After 2 hours of stirring at rt, the resulting reaction mixture is quenched with water (10 mL). Extraction with 3×Et₂O (50 mL), drying over MgSO₄ and evaporation under reduced pressure gives an oily residue. Flash chromatography on a 2×20 cm² column of SiO₂ using DCM/MeOH as eluting solvent (95/5) gives the title compound (0.08 g, 0.19 mmol) as a colorless oil in a 60% yield. Slow addition of HCl, (4 mL, 1M in Et₂O) into a solution of the above compound in MeOH (2 mL) gives the hydrochloride salt of the title compound.
Mp: 252° C. (decomposition).
¹H NMR (DMSO-d₆+D₂O, 300 MHz) δ 8.30-8.27 (d, 2H, J=7.7 Hz), 7.81-7.78 (d, 2H, J=8.3 Hz), 7.64-7.54 (m, 4H), 7.41-7.33 (m, 4H), 4.53 (br s, 3H), 4.03 (br s, 2H), 3.7-3.0 (m, 10H).

Example 48

(±)-1-(Carbazol-9-yl)-3-[4-(4-nitrobenzyl)piperazin-1-yl]propan-2-ol

The same method as employed in the preparation of Example 47 but starting from 4-nitrobenzaldehyde and Biotage purification gives an oily compound. Slow addition of HCl (1M in Et₂O) into a solution of the above compound in MeOH gives the hydrochloride salt of the title compound (0.03 g, 0.07 mmol) as a yellow solid in a 20% yield.
Mp: 213° C. (decomposition).
¹H NMR (DMSO-d₆+D₂O, 300 MHz) δ 8.00 (d, 2H, J=8.6 Hz), 7.92 (d, 2H, J=7.8 Hz), 7.40 (tr, 4H, J=8.15, 7.0 Hz), 7.22 (doublet of tr, 2H, J=7.80, 1.0 Hz), 6.99 (tr, 2H, J=7.67, 7.38 Hz), 4.53 (br s, 3H), 3.60 (br s, 2H), 3.4-2.9 (m, 10H).

Example 49

(±)-1-(Carbazol-9-yl)-3-[4-(4-methoxybenzyl)piperazin-1-yl]propan-2-ol

The same method as employed in the preparation of Example 47 but starting from 4-methoxybenzaldehyde and Biotage purification gives an oily compound. Slow addition of HCl (1M in Et₂O) into a solution of the above compound in MeOH gives the hydrochloride salt of the title compound (0.02 g, 0.04 mmol) as a grey blue solid in a 20% yield.
Mp: 220° C. (decomposition).
¹H NMR (DMSO-d₆+D₂O, 300 MHz) δ 7.90 (d, 2H, J=8.6 Hz), 7.41 (d, 2H, J=8.25 Hz), 7.24-7.12 (m, 4H), 7.22 (tr, 2H, J=7.40 Hz), 6.78 (d, 2H, J=8.13 Hz), 4.20 (br s, 3H), 3.90 (br s, 2H), 3.4-2.9 (m, 10H).

Example 50

(±)-1-[4-(4-Fluorobenzyl)piperazin-1-yl]-3-{3-[4-(trifluoromethyl)phenyl]-carbazol-9-yl}propan-2-ol The same method as employed in the preparation of Example 1 but starting from Intermediate 6, Intermediate 13 and sodium hydride and heating at 60° C. for 16 hours gives after Biotage chromatography the title compound as a yellow oil. Slow addition of HCl (1M in Et₂O) into a solution of the above compound in DCM gives the hydrochloride salt of the title compound as a camel-colored solid in a 52% yield.
Mp: 237° C. (decomposition).
¹H NMR (DMSO-d₆+D₂O, 300 MHz) δ 8.54 (d, 1H, J=1.45 Hz), 8.22 (d, 1H, J=7.65 Hz), 7.97 (d, 2H, J=8.22 Hz), 7.82-7.71 (m, 4H), 7.64 (d, 1H, J=8.3 Hz), 7.46-7.42 (tr, 3H, J=7.2 Hz), 7.23-7.18 (tr, 4H, J=7.8 Hz), 4.4-4.2 (m, 3H), 4.0 (m, 1H), 3.4-3.0 (m, 11H).

Example 51

(±)-1-[4-(4-Fluorobenzyl)piperazin-1-yl]-3-{3-[4-(trifluoromethoxy)phenyl]-carbazol-9-yl}propan-2-ol The same method as employed in the preparation of Example 1 but starting from Intermediate 6, Intermediate 14 and sodium hydride and heating at 60° C. for 16 hours gives after Biotage chromatography the title compound as a yellow oil. Slow addition of HCl (1M in Et₂O) into a solution of the above compound in DCM gives the hydrochloride salt of the title compound as a camel-colored solid in a 12% yield.
¹H NMR (DMSO-d₆+D₂O, 300 MHz) δ 8.40 (d, 1H, J=1.28 Hz), 8.15 (d, 1H, J=7.82 Hz), 7.97 (d, 2H, J=8.76 Hz), 7.74-7.62 (m, 2H), 7.58 (d, 1H, J=8.3 Hz), 7.44-7.30 (m, 4H), 7.20-7.03 (m, 3H), 6.75 (d, 1H, J=8.4 Hz), 4.4-4.2 (m, 3H), 4.0 (m, 1H), 3.4-3.0 (m, 11H).

Example 52

(±)-1-(Carbazol-9-yl)-3-[4-(3-fluorobenzyl)piperazin-1-yl]propan-2-ol

The same method as employed in the preparation of Example 47 but starting from 3-fluorobenzaldehyde using a parallel Quest 210 synthesizer (0.32 mmol scale) and Biotage purifica-tion gives an oily compound. Slow addition of HCl (1M in Et$_2$O) into a solution of the above compound in MeOH gives the hydrochloride salt of the title compound (0.128 g) as a beige-colored solid in a 95% yield.

Mp: 154° C. (decomposition).

$^1$H NMR (DMSO-d$_6$+D$_2$O, 300 MHz) δ 8.13 (d, 2H, J=7.6 Hz), 7.65 (m, 2H), 7.46-7.18 (m, 8H), 4.63 (br s, 2H), 4.38 (br s, 1H), 3.42-3.12 (m, 12H).

Example 53

(±)-1-(Carbazol-9-yl)-3-[4-(thien-2-ylmethyl)piper-azin-1-yl]propan-2-ol

The same method as employed in the preparation of Example 47 but starting from thiophene-2-carboxaldehyde using a parallel Quest 210 synthesizer (0.32 mmol scale) and Biotage purification gave an oily compound. Slow addition of HCl (1M in Et$_2$O) into a solution of the above compound in MeOH gives the hydrochloride salt of the title compound (0.080 g) as a beige-colored solid in a 61% yield.

Mp: 248° C. (decomposition).

$^1$H NMR (DMSO-d$_6$+D$_2$O, 300 MHz) δ 8.12 (d, 2H, J=7.7 Hz), 7.63 (m, 3H), 7.43 (tr, 2H, J=7.4, 7.9 Hz), 7.19 (tr, 3H, J=7.3 Hz), 7.05 (m, 1H), 4.37 (br s, 2H), 4.25 (br s, 1H), 3.52-2.93 (m, 12H).

Example 54

(±)-1-(4-Butylpiperazin-1-yl)-(3-carbazol-9-yl)pro-pan-2-ol

The same method as employed in the preparation of Example 47 but starting from butanal using a parallel Quest 210 synthesizer (0.32 mmol scale) and Biotage purification gives an oily compound. Slow addition of HCl (1M in Et$_2$O) into a solution of the above compound in MeOH gives the hydrochloride salt of the title compound (0.017 g) as a white solid in a 15% yield.

Mp: 242° C. (decomposition).

$^1$H NMR (DMSO-d$_6$+D$_2$O, 300 MHz) δ 8.12 (d, 2H, J=7.7 Hz), 7.62 (d, 2H, J=8.2 Hz), 7.42 (tr, 2H, J=7.21, 8.1 Hz), 7.19 (tr, 2H, J=7.4 Hz), 4.39 (br s, 2H), 4.31 (br s, 1H), 3.52-3.01 (m, 12H), 1.6 (m, 2H), 1.34 (m, 2H), 0.87 (tr, 3H, J=7.25 Hz).

Example 55

(±)-4-({4-[3-carbazol-9-yl-2-hydroxypropyl]piper-azin-1-yl}methyl)phenol

The same method as employed in the preparation of Example 47 but starting from 4-hydroxybenzaldehyde using a parallel Quest 210 synthesizer (0.32 mmol scale) and Biotage purification gives an oily compound. Slow addition of HCl (1M in Et$_2$O) into a solution of the above compound in MeOH gives the hydrochloride salt of the title compound (0.085 g) as a white solid in a 63% yield.

Mp: 207° C. (decomposition).

$^1$H NMR (DMSO-d$_6$+D$_2$O, 300 MHz) δ 8.12 (d, 2H, J=7.7 Hz), 7.64 (d, 2H, J=8.2 Hz), 7.43 (tr, 2H, J=7.23, 8.1 Hz), 7.31 (d, 2H, J=8.12), 7.19 (tr, 2H, J=7.4 Hz), 6.80 (d, 2H, J=8.45 Hz), 4.39 (br s, 2H), 4.17 (br s, 1H), 3.45-3.28 (br m, 12H).

Example 56

(±)-1-[4-(4-tert-Butylbenzyl)piperazin-1-yl]-3-(car-bazol-9-yl)propan-2-ol

The same method as employed in the preparation of Example 47 but starting from 4-tert-butylbenzaldehyde using a parallel Quest 210 synthesizer (0.32 mmol scale) and Biotage purification gives an oily compound. Slow addition of HCl (1M in Et$_2$O) into a solution of the above compound in MeOH gives the hydrochloride salt of the title compound (0.085 g) as a white solid in a 57% yield.

Mp: 246° C. (decomposition).

$^1$H NMR (DMSO-d$_6$+D$_2$O, 300 MHz) δ 8.12 (d, 2H, J=7.7 Hz), 7.64 (d, 2H, J=8.2 Hz), 7.43 (m, 6H), 7.19 (tr, 2H, J=7.4 Hz), 4.39 (br s, 2H), 4.17 (br s, 1H), 3.45-3.28 (br m, 12H), 1.27 (s, 9H).

Example 57

(±)-1-(Carbazol-9-yl)-3-[4-(3,4-dichlorobenzyl)pip-erazin-1yl]propan-2-ol

The same method as employed in the preparation of Example 47 but starting from 3,4-dichlorobenzaldehyde using a parallel Quest 210 synthesizer (0.32 mmol scale) and Biotage purification gives an oily compound. Slow addition of HCl (1M in Et$_2$O) into a solution of the above compound in MeOH gives the hydrochloride salt of the title compound (0.084 g) as a grey solid in a 56% yield.

Mp: 110° C. (decomposition).

$^1$H NMR (DMSO-d$_6$+D$_2$O, 300 MHz) δ 8.12 (d, 2H, J=7.7 Hz), 7.69 (s, 1H), 7.67 (m, 3 H), 7.54 (m, 3H), 7.19 (tr, 2H, J=7.4 Hz), 4.39 (br s, 2H), 4.17 (br s, 1H), 3.45-3.20 (br m, 12H).

Example 58

(±)-1-(Carbazol-9-yl)-3-{4-[4-(methylsulfonyl)ben-zyl])piperazin-1-yl}propan-2-ol The same method as employed in the preparation of Example 47 but starting from 4-(methylsulfonyl)benzalde-hyde using a parallel Quest 210 synthesizer (0.32 mmol scale) and Biotage purification gave an oily compound. Slow addi-tion of HCl (1M in Et$_2$O) into a solution of the above com-pound in MeOH gives the hydrochloride salt of the title com-pound (0.091 g) as a white solid in a 59% yield.

Mp: 85° C. (decomposition).

$^1$H NMR (DMSO-d$_6$+D$_2$O, 300 MHz) δ 8.12 (d, 2H, J=7.7 Hz), 7.90 (d, 2H, J=8.2 Hz), 7.6-7.62 (m, 4H), 7.46-7.40 (tr, 2H, J=8.2 Hz), 7.19 (tr, 2H, J=7.4 Hz), 4.39 (br s, 2H), 4.17 (br s, 1H), 3.45-3.20 (br m, 12H), 3.18 (s, 3H).

Example 59

(±)-1-(3,6-Dibromocarbazol-9-yl)-3-[4-(thien-2-ylmethyl)piperazin-1-yl]propan-2-ol The same method as employed in the preparation of Example 47 but starting from Example 5 and thiophene-2-carboxaldehyde using a parallel Quest 210 synthesizer (0.21 mmol scale) and Biotage purification gave an oily compound. Slow addition of HCl (1M in Et$_2$O) into a solution of the above compound in MeOH gives the hydrochloride salt of the title compound (0.066 g) as an off-white solid in a 57% yield.

Mp: 262° C. (decomposition).

$^1$H NMR (DMSO-d$_6$+D$_2$O, 300 MHz) δ 8.54 (d, 2H, J=1.71 Hz), 7.69-7.57 (m, 5H), 7.15 (s, 1H), 7.05 (tr, 1H, J=4.69, 3.67 Hz), 4.37 (br s, 2H), 4.25 (br s, 1H), 3.52-2.93 (m, 12H).

Example 60

(±)-1-(3,6-Dibromocarbazol-9-yl)-3-[4-(thien-3-ylmethyl)piperazin-1-yl]propan-2-ol The same method as employed in the preparation of Example 47 but starting from Example 5 and thiophene-3-carboxaldehyde using a parallel Quest 210 synthesizer (0.21 mmol scale) and Biotage purification gives an oily compound. Slow addition of HCl (1M in Et$_2$O) into a solution of the above compound in MeOH gives the hydrochloride salt of the title compound (0.09 g) as a pale yellow solid in a 76% yield.

Mp: 268-271° C. (decomposition).

$^1$H NMR (DMSO-d$_6$+D$_2$O, 300 MHz) δ 8.46 (d, 2H, J=1.82 Hz), 7.74-7.57 (m, 6H), 7.28 (d, 1H, J=4.64 Hz), 4.4-4.2 (br s, 2H), 4.1 (dd, 1H, J=5.2, 1.7 Hz), 3.52-2.93 (m, 12H).

Example 61

(±)-1-(3,6-Dibromocarbazol-9-yl)-3-[4-(pyridin-3-ylmethyl)piperazin-1-yl]propan-2-ol The same method as employed in the preparation of Example 47 but starting from Example 5 and nicotinaldehyde using a parallel Quest 210 synthesizer (0.21 mmol scale) and Biotage purification gives an oily compound. Slow addition of HCl (1M in Et$_2$O) into a solution of the above compound in MeOH gives the hydrochloride salt of the title compound (0.057 g) as a hygroscopic salmon-colored powder in a 30% yield.

$^1$H NMR (DMSO-d$_6$+D$_2$O, 300 MHz) δ 8.8 (m, 2H), 8.47 (2 d, 2H, J=8.3, 1.8 Hz), 8.32 (d, 1H, J=7.92 Hz), 8.01 (dd, 1H, J=8.0 Hz), 7.82 (m, 1H), 7.69-7.57 (m, 3H), 4.4-4.2 (br s, 2H), 4.1 (dd, 1H, J=5.2, 1.7 Hz), 3.52-2.93 (m, 12H).

Example 62

(±)-1-(3,6-Dibromocarbazol-9-yl)-3-[4-(4-methoxybenzyl)piperazin-1-yl]propan-2-ol The same method as employed in the preparation of Example 47 but starting from Example 5 and 4-methoxybenzaldehyde using a parallel Quest 210 synthesizer (0.21 mmol scale) and Biotage purification gives an oily compound. Slow addition of HCl (1M in Et$_2$O) into a solution of the above compound in MeOH gives the hydrochloride salt of the title compound (0.053 g) as a white powder in a 43% yield.

Mp: 251° C. (decomposition).

$^1$H NMR (DMSO-d$_6$+D$_2$O, 300 MHz) δ 8.45 (d, 2H, J=1.7 Hz), 7.70-7.57 (m, 4H), 7.42 (d, 2H, J=7.9 Hz), 6.98 (d, 2H, J=8.48 Hz), 4.4-4.2 (br s, 2H), 4.1 (dd, 1H, J=5.2, 1.7 Hz), 3.9 (s, 3H), 3.52-2.93 (m, 12H).

Example 63

(±)-1-(3,6-Dibromocarbazol-9-yl)-3-[4-(4-tert-butylbenzyl)piperazin-1-yl]propan-2-ol The same method as employed in the preparation of Example 47 but starting from Example 5 and 4-tert-butyl benzaldehyde using a parallel Quest 210 synthesizer (0.21 mmol scale) and Biotage purification gives an oily compound. Slow addition of HCl (1M in Et$_2$O) into a solution of the above compound in MeOH gives the hydrochloride salt of the title compound (0.061 g) as a white powder in a 48% yield.

Mp: 242° C. (decomposition).

$^1$H NMR (DMSO-d$_6$+D$_2$O, 300 MHz) δ 8.46 (d, 2H, J=1.7 Hz), 7.68 (d, 2H, J=8.8 Hz), 7.61-7.58 (dd, 2H, J=8.7, 1.85 Hz), 7.47 (br s, 4H), 4.4-4.2 (br s, 3H), 3.52-2.93 (m, 12H), 1.27 (s, 9H).

Example 64

(±)-1-(3,6-Dibromocarbazol-9-yl)-3-[4-(4-trifluoromethylbenzyl)piperazin-1-yl]propan-2-ol The same method as employed in the preparation of Example 47 but starting from Example 5 and 4-trifluoromethylbenzaldehyde using a parallel Quest 210 synthesizer (0.21 mmol scale) and Biotage purification gives an oily compound. Slow addition of HCl (1M in Et$_2$O) into a solution of the above compound in MeOH gives the hydrochloride salt of the title compound (0.058 g) as a pale yellow powder in a 44% yield.

Mp: 243° C. (decomposition).

$^1$H NMR (DMSO-d$_6$+D$_2$O, 300 MHz) δ 8.46 (d, 2H, J=1.7 Hz), 7.88-7.50 (m, 8H), 4.4-4.2 (br s, 2H), 4.12 (br s, 1H), 3.52-2.93 (m, 12H).

Example 65

(±)-1-[4-(1,3-Benzodioxol-5-ylmethyl)piperazin-1-yl]-3-(3,6-dibromo-carbazol-9-yl)propan-2-ol The same method as employed in the preparation of Example 47 but starting from Example 5 and 1,3-benzodioxole-5-carboxaldehyde using a parallel Quest 210 synthesizer (0.21 mmol scale) and Biotage purification gives an oily compound. Slow addition of HCl (1M in Et$_2$O) into a solution of the above compound in MeOH gives the hydrochloride salt of the title compound (0.051 g) as a pale yellow powder in a 40% yield.

Mp: 272° C. (decomposition).

$^1$H NMR (DMSO-d$_6$+D$_2$O, 300 MHz) δ 8.46 (d, 2H, J=1.7 Hz), 7.70-7.57 (m, 4H), 7.11 (s, 1H), 6.97 (s, 2H), 6.046 (s, 2H), 4.4-4.2 (br s, 2H), 4.12 (dd, 1H, J=5.6, 1.8 Hz), 3.52-2.93 (m, 12H).

Example 66

(±)-1-(4-Cyclohexylmethylpiperazin-1-yl)-3-(3-phenylcarbazol-9-yl)-propan-2-ol

The same method as employed in the preparation of Example 1 but starting from Intermediate 7, Intermediate 11 and sodium hydride and heating at 60° C. for 16 hours gives after flash chromatography the title compound as a yellow foam. Slow addition of HCl (1M in Et$_2$O) into a solution of the above compound in DCM gives the hydrochloride salt of the title compound as a white solid in a 90% yield.

Mp: 265-270° C. (decomposition).

$^1$H NMR (DMSO-d$_6$+D$_2$O, 300 MHz) δ 8.46 (s, 1H), 8.24 (d, 2H, J=7.67 Hz), 7.78-7.69 (m, 5H), 7.50-7.45 (m, 3H), 7.32 (tr, 1H, J=7.3 Hz), 7.22 (tr, 1H, J=7.4 Hz), 4.4-4.3 (m, 3H), 3.6-3.0 (m, 11H), 2.9 (br s, 1H), 1.8-1.5 (m, 6H), 1.2-0.9 (m, 5H).

Analysis for $C_{32}H_{39}N_3O \cdot 2HCl \cdot 0.8 H_2O$:
Calculated: C, 67.55; H, 7.55; N, 7.38;
Found: C, 67.61; H, 7.82; N, 7.42%.

Example 67

(±)-3,6-Dibromo-9-{3-[4-(cyclohexylmethyl)piper-azin-1-yl]-2-fluoropropyl}-carbazole Under an inert atmosphere a solution of Example 45 (0.10 g, 0.18 mmol) in anhydrous DCM (8 mL) is treated with DAST (0.77 mmol). The resulting slurry is allowed to warm up to rt. Tlc monitoring ($SiO_2$, DCM/MeOH (95/5) shows formation of a few new UV active compounds and disappearance of the starting material. The reaction mixture is quenched with a saturated aqueous solution of potassium carbonate (10 mL). Extraction with DCM (3×20 mL), drying over $MgSO_4$ and evaporation of the solvent under reduced pressure gives an oil. Purification on a 2×21 cm² $SiO_2$ column using Petroleum Ether/EtOAc/MeOH (6/1/0.15) as eluant gives the title compound (Rf=0.2) as the UV active major product of the reaction. Slow addition of a solution of the above major compound (Rf=0.2) in DCM into a solution of HCl(1M in $Et_2O$) gives the hydrochloride salt of the title compound as a beige solid in a 52% yield.
Mp: 265-270° C. (decomposition).
$^1$H NMR (DMSO-$d_6$+$D_2O$, 300 MHz) δ 8.48 (s, 2H), 7.67 (d, 2H, J=8.9 Hz), 7.62 (d, 2H, J=8.9 Hz), 5.35 (d, 1H, J=51.4 Hz), 4.69 (m, 2H), 3.90-3.10 (m, 10H), 2.97 (d, 2H, J=5.1 Hz), 1.85-1.55 (m, 6H), 1.30-1.05 (m, 3H), 1.05-0.85 (m, 2H).

Example 68

(±)-9-{3-[4-(Cyclohexylmethyl)piperazin-1-yl]-2-fluoropropyl}-3-phenyl-carbazole The same method as employed in the preparation of Example 67 but starting from Example 66 gives a more polar UV active compound (Rf=0.17 using $SiO_2$, Petroleum Ether/EtOAc/MeOH (6/1/0.15) as eluting solvent). Slow addition of HCl into a solution of the above compound in DCM gives the hydrochloride salt of the title compound as a beige solid in a 20% yield.
Mp: 255° C. (decomposition).
FI-MS (APCI): m/z observed in a positive mode: 484.2.
$^1$H NMR (CDCl$_3$, 300 MHz) of the base form of the title compound 88.28 (d, 1H, J=1.5 Hz), 8.12 (d, 1H, J=7.9 Hz), 7.70 (m, 3H), 7.58-7.42 (m, 5H), 7.33 (m, 1H), 7.25 (ddd, 1H, J=7.9, 6.4, 1.5 Hz), 5.04 (dm, 1H, J=47.5 Hz), 4.67 (ddd, 1H, J=22.2, 15.7, 4.1 Hz), 4.54 (ddd, 1H, J=20.3, 15.7, 6.0 Hz), 2.70-2.40 (m, 10H), 2.16 (d, 2H, J=7.2 Hz), 1.81-1.60 (m, 5H), 1.49 (m, 1H), 1.31-1.06 (m, 3H), 0.96-0.77 (m, 2H).

Example 69

(±)-4-[3-(3,6-Dibromocarbazol-9-yl)-2-hydroxypropyl]-N-(4-fluorophenyl)piperazine-1-carboxamide A solution of Example 5 (0.20 g, 0.43 mmol) in DCM (10 mL) is treated with DIEA (80 μL, 1 equiv.) and 1-fluoro-4-isocyanatobenzene (0.06 g, 1 equiv.). The resulting solution is allowed to stir for 4 hours. The solvent is evaporated off. The crude residue is taken up in DCM (5 mL) and is purified via flash chromatography on $SiO_2$ using DCM/MeOH (95/5) as eluting solvent. A by-product is identified as (±)-2-(3,6-dibromocarbazol-9-yl)-1-({4-[4(4-fluoroanilino)carbonyl]piperazin-1-yl}methyl)ethyl 4-fluorophenylcarbamate (Rf=0.45), FI-MS (APCI): m/z observed in a positive mode: 742.4). The major UV active compound (Rf=0.41) is identified as the title compound. Slow addition of HCl (1M in $Et_2O$) into a solution of the above compound (Rf=0.41) in MeOH gives the hydrochloride salt of the title compound (0.125 g) as a white powder in a 48% yield.
Mp: 184° C. (decomposition).
$^1$H NMR (DMSO-$d_6$+$D_2O$, 300 MHz) δ 8.40 (br. s, 2H), 7.60 (d, 2H, J=8.3 Hz), 7.55 (d, 2H, J=8.3 Hz), 7.34 (m, 2H), 7.01 (m, 2H), 4.33 (br. s, 3H), 4.07 (m, 2H), 3.50-2.90 (m, 8H).

Example 70

(±)-1-(3,6-Dibromo-carbazol-9-yl)-3-[4-(thien-2-ylsulfonyl)piperazin-1-yl]propan-2-ol A solution of Example 5 (0.20 g, 0.43 mmol) in DMF (7 mL) is treated with TEA (60 uL, 1 equiv.) and thiophene-2-sulfonyl chloride (0.078 g, 1 equiv.). The resulting solution is allowed to stir for 2 hours. The solvent is evaporated. The crude residue is taken up in DCM (5 mL) and is purified via flash chromatography using DCM/MeOH (95/5) as eluant. Slow addition of HCl (1M in $Et_2O$) into a solution of the purified above compound in MeOH gives the hydrochloride salt of the title compound (0.233 g, 0.36 mmol) as a white powder in a 84% yield.
Mp: 252° C. (decomposition).
Analysis for $C_{23}H_{23}Br_2N_3O_3S \cdot HCl$:
Calculated: C, 42.51; H, 3.72; N, 6.47;
Found: C, 42.26; H, 4.00; N, 6.55%.

Example 71

(±)-1-[4-(Benzylsulfonyl)piperazin-1-yl]-3-(3,6-dibromo-carbazol-9yl)propan-2-ol The same method as employed in the preparation of Example 70 but starting from phenyl methane sulfonyl chloride gives the hydrochloride salt of the title compound as a beige-colored solid in a 71% yield.
Mp: 253° C. (decomposition).
Analysis for $C_{26}H_{27}Br_2N_3O_3S \cdot HCl$:
Calculated: C, 47.47; H, 4.29; N, 6.39;
Found: C, 47.18; H, 4.31; N, 6.32%.

Example 72

(±)-1-(3,6-Dibromo-carbazol-9-yl)-3-[4-(3,4-dichlorobenzyl)piperazin-1-yl]propan-2-ol The same method as employed in the preparation of Example 47 but starting from Example 5 and 3,4-dichlorobenzaldehyde gives the hydrochloride salt of the title compound as a white powder in a 77% yield.
Mp: 287° C. (decomposition).
Analysis for $C_{26}H_{25}Br_2Cl_2N_3O \cdot 2HCl \cdot 0.2H_2O$:
Calculated: C, 44.44; H, 3.93; N, 5.98;
Found: C, 44.13; H, 4.08; N, 5.92%.

Example 73

(±)-1-(3,6-Dibromo-carbazol-9-yl)-3-[4-(2-morpholin-4-ethyl)piperazin-1-yl]propan-2-ol A solution of Intermediate 15 (1.65 g, 4.33 mmol) and 4-(2-piperazin-1-ylethyl)morpholine (2.55 g, 12.79 mmol) in anhydrous THF/absolute EtOH (22.5 mL/22.5 mL) is allowed to stir at 60° C. for 18 hours. The solvents are evaporated. The residue is taken up in EtOAc/MeOH/aqueous ammonia (25%) (8/1.5/0.5) and purified on a 5×27 cm² column of SiO₂ using EtOAc/MeOH/aqueous ammonia (25%) (8/1.5/0.5) as eluant to give the title compound (2.45 g, 4.22 mmol) as a pale yellow foam in a 97% yield. Slow addition of HCl (21.5 mL, 1M in Et₂O) into a solution of the above compound in MeOH/DCM (100 mL/50 mL) gives the hydrochloride of the title compound as a white powder.

Mp: 270° C. (decomposition).

$^1$H NMR (DMSO-d$_6$+MeOD-d$_4$, 300 MHz) δ 8.47 (d, 2H, J=1.9 Hz), 7.72 (d, 2H, J=8.7 Hz), 7.60 (dd, 2H, J=8.7, 1.9 Hz), 4.42 (br s, 3H), 3.88 (br s, 4H), 3.75-2.80 (m, 18H).

Analysis for $C_{25}H_{32}Br_2N_4O_2$. 3HCl:

Calculated: C, 43.53; H, 5.11; N, 8.12;

Found: C, 43.36; H, 5.29; N, 8.06%.

Example 74

(±)-1-[4-(4-Fluorobenzyl)piperazin-1-yl]-3-(3-thien-2-yl-carbazol-9-yl)-propan-2-ol The same method as employed in the preparation of Example 1 but starting from Intermediate 16, Intermediate 6 and sodium hydride and heating at 60° C. for 16 hours gives after flash chromatography the title compound as a yellow oil. Slow addition of HCl (1M in Et₂O) into a solution of the above compound in DCM gives the hydrochloride salt of the title compound as a gummy green solid in a 62% yield.

FI-MS (APCI): m/z observed in a positive mode: 500.4.

Example 75

(±)-1-(3,6-Dibromo-carbazol-9-yl)-3-{4-[3,4-diethoxyphenyl)sulfonyl]piperazin-1-yl}propan-2-ol The same method as employed in the preparation of Example 70 but starting from 3,4-dimethoxybenzenesulfonyl chloride gives the hydrochloride salt of the title compound as a beige solid (0.117 g) in a 84% yield.

Mp: 267° C. (decomposition).

Analysis for $C_{27}H_{29}Br_2N_3O_5S$. HCl:

Calculated: C, 46.07; H, 4.30; N, 5.97;

Found: C, 45.95; H, 4.40; N, 5.88%.

Example 76

(±)-1-[4-(Cyclohexylmethyl)piperazin-1-yl]-3-(3,6-dichloro-carbazol-9-yl)propan-2-ol The same method as employed in the preparation of Example 1 but starting from 3,6-dichloro-9H-carbazole, Intermediate 11 and sodium hydride and heating at 60° C. for 16 hours gives after flash chromatography the title compound (UV active, Rf=0.25 using DCM/MeOH (100/5) as eluant) as a white foam. Slow addition of HCl (1M in Et₂O) into a solution of the above compound in DCM gives the hydrochloride salt of the title compound as a white solid in a 71% yield.

Mp: 302° C. (decomposition).

Analysis for $C_{26}H_{33}Cl_2N_3O$. 2HCl. 0.3 H₂O:

Calculated: C, 56.49; H, 6.49; N, 7.60;

Found: C, 56.48; H, 6.52; N, 7.60%.

Example 77

(±)-4-[3-(3,6-Dichlorocarbazol-9-yl)-2-hydroxypropyl]-piperazine-1-carboxylic tert-butyl ester The same method as employed in the preparation of Example 1 but starting from 3,6-dichloro-9H-carbazole and (±)-4-oxiranylmethyl-piperazine-1-carboxylic acid tert-butyl ester gives after flash chromatography the title compound as a white foam in a 74% yield.

$^1$H NMR (CDCl₃, 300 MHz) δ 7.90 (d, 2H, J=1.32 Hz), 7.39-7.34 (m, 4H), 4.32-4.07 (m, 3H), 3.35 (br s, 4H), 2.52-2.22 (m, 6H), 1.41 (s, 9H).

Example 78

(±)-1-(3,6-Dichlorocarbazol-9-yl)-3-piperazin-1-yl-propan-2-ol

The same method as employed in the preparation of Example 3 but starting from Example 77 gives the hydrochloride salt of title compound as a white solid in a 71% yield.

Mp: 305° C. (decomposition).

Analysis for $C_{19}H_{21}Cl_2Br_2N_3O$. 2HCl. 0.3H₂O:

Calculated: C, 50.18; H, 5.19; N, 9.24;

Found: C, 50.06; H, 5.15; N, 9.12%.

Example 79

(±)-4-[3-(3,6-Dibromocarbazol-9-yl)-2-oxopropyl]-piperazine-1-carboxylic tert-butyl ester At −78° C. a solution of oxalyl chloride (200 μL, 2.34 mmol) in anhydrous DCM (20 mL) is treated with anhydrous DMSO (310 μL, 4.37 mmol). After 15 min of stirring at −78° C., a solution of Example 4 (1.0 g, 1.76 mmol) in anhydrous DCM (5 mL) is added dropwise. The resulting mixture is allowed to stir for 40 min at −78° C. and TEA (1250 μL) is added neat. After 10 min the reaction mixture is allowed to warm up to −30° C. After 1 hour of stirring at −30° C. the reaction mixture is quenched with water (50 mL). Extraction with DCM (3×100 mL), drying over MgSO₄ and evaporation under reduced pressure gives a yellow oil. Flash chromatography on a 4×21 cm² SiO₂ column using Et₂O/MeOH (100/1) mixture then (100/3) as eluant gives the title compound as a pale yellow foam (0.804 g, 1.42 mmol) in a 81% yield.

$^1$H NMR (CDCl₃, 300 MHz) δ 8.12 (d, 2H, J=1.9 Hz), 7.52 (dd, 2H, J=8.6, 1.9), 7.12 (d, 2H, J=8.6), 5.00 (s, 2H), 3.39 (m, 4H), 3.05 (s, 2H), 2.32 (m, 4H), 1.42 (s, 9H).

Example 80

(±)-3,6-Dibromo-9-(2,2-difluoro-3-piperazin-1-yl-propyl)-carbazole

The same method as employed in the preparation of Example 3 but starting from (±)-4-[3-(3,6-dibromocarbazol-9-yl)-2,2-difluoropropyl]piperazine-1-carboxylic tert-butyl-lester gives the hydrochloride salt of title compound as a beige solid in a 71% yield.

Mp: 305° C. (decomposition).

FI-MS (APCI): m/z observed in a positive mode: 488.0

Preparation of (±)-4-[3-(3,6-dibromocarbazol-9-yl)-2,2-difluoropropyl]-piperazine-1-carboxylic tert-butyl ester DAST (100 uL, 0.76 mmol) is added into a solution of from (±)-4-[3-(3,6-dibromocarbazol-9-yl)-2-oxopropyl]-piperazine-1-carboxylic tert-butylester (0.100 g, 0.18 mmol) in anhydrous DCM (4 mL) at rt. The resulting mixture is allowed to stir for 21 hours and quenched with a saturated aqueous solution of sodium hydrogenocarbonate (20 mL). Extraction with DCM (3×40 mL), drying over $MgSO_4$ and evaporation under reduced pressure gives a brown oil. Flash chromatography on a 2×21 $cm^2$ $SiO_2$ column using DCM/MeOH (100/1.5) as eluant gives the title compound as a yellow oil.

$^1$H NMR ($CDCl_3$, 300 MHz) δ 8.09 (d, 2H, J=1.9 Hz), 7.53 (dd, 2H, J=8.7, 1.9 Hz), 7.42 (d, 2H, J=8.7 Hz), 4.67 (t, 2H, J=13.0 Hz), 3.47 (m, 4H), 2.64 (t, 2H, J=13.0 Hz), 2.49 (br. s, 4H), 1.46 (s, 9H).

Example 81

(±)-1-(3-Bromo-carbazol-9-yl)-3-[4-(2-phenylethyl)piperazin-1-yl]propan-2-ol

The same method as employed in the preparation of Example 47 but starting from Example 9 and phenyl acetaldehyde using a parallel Radley synthesizer (0.21 mmol scale) and parallel flash purification (ISCO device) gives an oily compound. Slow addition of HCl (1M in $Et_2O$) into a solution of the above compound in MeOH gives the hydrochloride salt of the title compound as a beige solid in a 62% yield.

Mp: 264° C. (decomposition).
$^1$H NMR (DMSO-$d_6$+$CD_3OD$, 300 MHz) δ 8.39 (d, J=1.88 Hz, 1H), 8.20 (d, J=7.54 Hz, 1H), 7.71 (tr, J=9.04, 9.42 Hz, 2H), 7.57 (dd, J=8.67, 1.9 Hz, 1H), 7.45 (tr, J=7.91, 7.54 Hz, 1H), 7.35-7.20 (m, 6H), 4.42 (br s, 3H), 4.03-3.07 (m, 14H).

Example 82

(±)-1-(3-Bromo-carbazol-9-yl)-3-[4-(2,3-dihydro-1,4-benzodioxin-6-ylmethyl)piperazin-yl]propan-2-ol The same method as employed in the preparation of Example 47 but starting from Example 9 and 2,3-dihydro-1,4-dihydro-1,4-benzodioxine-6-carboxaldehyde using a parallel Radley, synthesizer (0.21 mmol scale) and parallel flash purification (ISCO device) gives an oily compound. Slow addition of HCl (1M in $Et_2O$) into a solution of the above compound in MeOH gives the hydrochloride salt of the title compound as a beige solid in a 49% yield.

Mp: 230° C. (decomposition).
$^1$H NMR (DMSO-$d_6$+$CD_3OD$, 300 MHz) δ 8.38 (br s, 1H), 8.19 (d, 1H, J=7.54 Hz), 7.71 (tr, 2H, J=9.04, 9.42 Hz), 7.57 (dd, 1H, J=8.67, 1.9 Hz), 7.45 (tr, 1H, J=7.91, 7.54 Hz), 7.24 (tr, 1H, J=7.53 Hz), 7.14 (br s, 1H), 7.02 (br s, 1H), 6.90 (d, 1H, J=7.91 Hz), 4.39 (br s, 3H), 4.23 (s, 2H), 4.015 (s, 2H), 4.49-3.3.27 (m, 12H).

Example 83

(±)-1-(3-Bromo-carbazol-9-yl)-3-[4-(4-fluorobenzyl)piperazin-1-yl]propan-2-ol

The same method as employed in the preparation of Example 47 but starting from Example 9 and 4-fluorobenzaldehyde using a parallel Radley synthesizer (0.21 mmol scale) and parallel flash purification (ISCO device) gives an oily compound. Slow addition of HCl (1M in $Et_2O$) into a solution of the above compound in MeOH gives the hydrochloride salt of the title compound as a white solid in a 67% yield.

Mp: 267° C. (decomposition).
$^1$H NMR (DMSO-$d_6$+$CD_3OD$, 300 MHz) δ 8.38 (d, 1H, J=1.88 Hz), 8.19 (d, 1H, J=7.54 Hz), 7.73-7.67 (m, 3H), 7.57 (dd, 1H, J=8.67, 1.9 Hz), 7.45 (tr, 1H, J=7.91, 7.54 Hz), 7.32-7.20 (m, 4H), 7.14 (br s, 1H), 4.40 (br s, 3H), 3.64-3.28 (m, 12H).

Example 84

(±)-1-(3-Bromo-carbazol-9-yl)-3-[4-(3,4-dichlorobenzyl)piperazin-1-yl]propan-2-ol The same method as employed in the preparation of Example 47 but starting from Example 9 and 3,4-dichlorobenzaldehyde using a parallel Radley synthesizer (0.21 mmol scale) and parallel flash purification (ISCO device) gives an oily compound. Slow addition of HCl (1M in $Et_2O$) into a solution of the above compound in MeOH gives the hydrochloride salt of the title compound as a white solid in a 52% yield.

Mp: 183° C. (decomposition).
$^1$H NMR (DMSO-$d_6$+$CD_3OD$, 300 MHz) δ 8.38 (d, 1H, J=1.88 Hz), 8.19 (d, 1H, J=7.54 Hz), 7.88 (br s, 1H), 7.72-7.67 (m, 3H), 7.57 (dd, 2H, J=8.67, 1.9 Hz), 7.45 (tr, 1H, J=7.91, 7.54 Hz), 7.21 (tr, 1H, J=7.53, 7.0 Hz), 4.40 (br s, 3H), 3.64-3.28 (m, 12H).

Example 85

(±)-1-(3-Bromo-carbazol-9-yl)-3-{4-[4-(difluoromethoxybenzyl]piperazin-1-yl}propan-2-ol The same method as employed in the preparation of Example 47 but starting from Example 9 and 4-difluoromethoxy benzaldehyde using a parallel Radley synthesizer (0.21 mmol scale) and parallel flash purification (ISCO device) gives an oily compound. Slow addition of HCl (1M in $Et_2O$) into a solution of the above compound in MeOH gives the hydrochloride salt of the title compound as a white solid in a 37% yield.

Mp: 184° C. (decomposition).
$^1$H NMR (DMSO-$d_6$+$CD_3OD$, 300 MHz) δ 8.38 (d, 1H, J=1.88 Hz), 8.19 (d, 1H, J=7.54 Hz), 7.77-7.66 (m, 4H), 7.57 (dd, 1H, J=8.67, 1.9 Hz), 7.45 (tr, 1H, J=7.91, 7.54 Hz), 7.21 (m, 4H), 4.40 (br s, 3H), 3.64-3.28 (m, 12H).

Example 86

(±)-1-(3-Bromo-carbazol-9-yl)-3-[4-(cyclohexylmethyl)piperazin-1-yl]propan-2-ol

The same method as employed in the preparation of Example 47 but starting from Example 9 and cyclohexanecarboxaldehyde using a parallel Radley synthesizer (0.21 mmol scale) and parallel flash purification (ISCO) gives an oily compound. Slow addition of HCl (1M in $Et_2O$) into a solution of the above compound in MeOH gives the hydrochloride salt of the title compound as a white solid in a 48% yield.

Mp: 271° C. (decomposition).
$^1$H NMR (DMSO-$d_6$+$D_2O$, 300 MHz) δ 8.39 (d, 1H, J=1.88 Hz), 8.20 (d, 1H, J=7.54 Hz), 7.74-7.68 (tr, 2H, J=9.42, 8.66 Hz), 7.57 (dd, 1H, J=8.17, 1.88 Hz), 7.48 (tr, 1H, J=7.54 Hz), 7.22 (tr, 1H, J=7.54, 7.16 Hz), 5.35 (d, 1H, J=51.4

Hz), 4.69 (m, 2H), 3.90-3.10 (m, 10H), 2.97 (d, 2H, J=5.1 Hz), 1.85-1.55 (m, 6H), 1.30-1.05 (m, 3H), 1.05-0.85 (m, 2H).

Example 87

(±)-1-[4-(1,3-Benzodioxol-5ylmethyl)piperazin-1-yl]-3-(3-bromo-carbazol-9-yl)propan-2-ol The same method as employed in the preparation of Example 47 but starting from Example 9 and 1,3-benzodioxole-5-carboxaldehyde using a parallel Radley synthesizer (0.21 mmol scale) and parallel flash purification (ISCO device) gives an oily compound. Slow addition of HCl (1M in $Et_2O$) into a solution of the above compound in MeOH gives the hydrochloride salt of the title compound as a white solid in a 49% yield.

Mp: 199° C. (decomposition).

$^1$H NMR (DMSO-$d_6$+$D_2O$, 300 MHz) δ 8.39 (d, 1H, J=1.88 Hz), 8.20 (d, 1H, J=7.54 Hz), 7.68 (m, 2H), 7.57-7.44 (m, 2H), 7.24 (m, 2H), 6.97 (m, 2H), 6.046 (s, 2H), 4.4-4.2 (br s, 2H), 4.12 (dd, 1H, J=5.6, 1.8 Hz), 3.52-2.93 (m, 12H).

Example 88

(±)-1-(3-Bromocarbazol-9-yl)-3-[4-(4-methoxybenzy)piperazin-1-yl]propan-2-ol

The same method as employed in the preparation of Example 47 but starting from Example 9 and 4-methoxybenzaldehyde using a parallel Radley synthesizer (0.21 mmol scale) and parallel flash purification (ISCO device) gives an oily compound. Slow addition of HCl (1M in $Et_2O$) into a solution of the above compound in MeOH gives the hydrochloride salt of the title compound as a white solid in a 68% yield.

Mp: 212° C. (decomposition).

$^1$H NMR (DMSO-$d_6$+$D_2O$, 300 MHz) δ 8.38 (d, 1H, J=1.88 Hz), 8.20 (d, 1H, J=7.54 Hz), 7.68 (m, 2H), 7.57-7.44 (m, 4H), 7.24 (tr, 1H, J=7.53, 7.16 Hz), 6.9 (d, 2H, J=8.28 Hz), 4.4-4.2 (br s, 2H), 4.12 (dd, 1H, J=5.6, 1.8 Hz), 3.52-2.93 (m, 15H).

Example 89

(±)-1-(3-Bromocarbazol-9-yl)-3-[4-(4-trifluoromethylbenzyl)piperazin-1-yl]propan-2-ol The same method as employed in the preparation of Example 47 but starting from Example 9 and 4-trifluoromethyl benzaldehyde using a parallel Radley synthesizer (0.21 mmol scale). Parallel flash purification (ISCO device) gives an oily compound. Slow addition of HCl (1M in $Et_2O$) into a solution of the above compound in MeOH gives the hydrochloride salt of the title compound as a white solid in a 61% yield.

Mp: 177° C. (decomposition).

$^1$H NMR (DMSO-$d_6$+$D_2O$, 300 MHz) δ 8.38 (br s, 1H), 8.20 (d, 1H, J=7.54 Hz), 7.80-7.65 (m, 6H), 7.57-7.44 (d, 1H, J=8.67 Hz), 7.50-7.44 (tr, 1H, J=7.54 Hz), 7.20 (tr, 1H, J=7.54, 7.16 Hz), 4.4-4.2 (br s, 3H), 3.52-2.93 (m, 12H).

Example 90

(±)-1-(3-Bromo-carbazol-9-yl)-3-[4-(3,5-dichlorobenzyl)piperazin-1-yl]propan-2-ol The same method as employed in the preparation of Example 47 but starting from Example 9 and 3,5-dichlorobenzaldehyde using a parallel Radley synthesizer (0.21 mmol scale) and parallel flash purification (ISCO device) gives an oily compound. Slow addition of HCl (1M in $Et_2O$) into a solution of the above compound in MeOH gives the hydrochloride salt of the title compound as a white solid in a 55% yield.

Mp: 259° C. (decomposition).

$^1$H NMR (DMSO-$d_6$+$CD_3OD$, 300 MHz) δ 8.38 (d, 1H, J=1.88 Hz), 8.19 (d, 1H, J=7.54 Hz), 7.72-7.65 (m, 4H), 7.57 (dd, 2H, J=8.67, 1.9 Hz), 7.45 (tr, 1H, J=7.91, 7.54 Hz), 7.21 (tr, 1H, J=7.53, 7.0 Hz), 4.40 (br s, 3H), 3.64-3.28 (m, 12H).

Example 91

(±)-1-(3-Bromocarbazol-9-yl)-3-[4-(4-tert-butylbenzyl)piperazin-1-yl]propan-2-ol The same method as employed in the preparation of Example 47 but starting from Example 9 and 4-tert-butylbenzaldehyde using a parallel Radley synthesizer (0.21 mmol scale) and parallel flash purification (ISCO device) gives an oily compound. Slow addition of HCl (1M in $Et_2O$) into a solution of the above compound in MeOH gives the hydrochloride salt of the title compound as a white solid in a 49% yield.

Mp: 250° C. (decomposition).

$^1$H NMR (DMSO-$d_6$+$CD_3OD$, 300 MHz) δ 8.38 (br s, 1H), 8.19 (d, 1H, J=7.54 Hz), 7.72-7.65 (tr, 2H, J=8.66 Hz), 4H), 7.57-7.44 (m, 6H), 7.21 (tr, 1H, J=7.53, 7.0 Hz), 4.40 (br s, 3H), 3.64-3.28 (m, 12H), 1.27 (s, 9H).

Example 92

(±)-1-(3-Bromo-carbazol-9-yl)-3-[4-(2-furylmethyl)piperazin-1-yl]propan-2-ol

The same method as employed in the preparation of Example 47 but starting from Example 9 and 2-furaldehyde using a parallel Radley synthesizer (0.21 mmol scale) and parallel flash purification (ISCO device) gives an oily compound. Slow addition of HCl (1M in $Et_2O$) into a solution of the above compound in MeOH gives the hydrochloride salt of the title compound as a yellow solid in a 34% yield.

Mp: 248° C. (decomposition).

$^1$H NMR (DMSO-$d_6$+$CD_3OD$, 300 MHz) δ 8.38 (br s, 1H), 8.19 (d, 1H, J=7.92 Hz), 7.79 (br s, 1H), 7.66 (m, 2H), 7.55 (d, 1H, J=8.1 Hz), 7.47 (tr, 1H, J=7.54, 7.16 Hz), 7.22 (tr, 1H, J=7.53, 7.16 Hz), 6.68 (br s, 1H), 6.54 (br s, 1H), 4.40 (br s, 3H), 3.64-3.28 (m, 12H).

Example 93

(±)-1-(3-Bromo-carbazol-9-yl)-3-[4-(2-furylmethyl)piperazin-1-yl]propan-2-ol

The same method as employed in the preparation of Example 47 but starting from Example 9 and 5-methyl-2-furaldehyde using a parallel Radley synthesizer (0.21 mmol scale) and parallel flash purification (ISCO device) gives an oily compound. Slow addition of HCl (1M in $Et_2O$) into a solution of the above compound in MeOH gives the hydrochloride salt of the title compound as a white solid in a 67% yield.

Mp: 240° C. (decomposition).

$^1$H NMR (DMSO-$d_6$, 300 MHz) δ 8.38 (br s, 1H), 8.19 (d, 1H, J=7.92 Hz), 7.66 (m, 2H), 7.55 (d, 1H, J=8.1 Hz), 7.47 (tr,

1H, J=7.54, 7.16 Hz), 7.22 (tr, 1H, J=7.53, 7.16 Hz), 6.68 (br s, 1H), 6.54 (br s, 1H), 4.40 (br s, 3H), 3.64-3.28 (m, 12H), 2.26 (s, 3H).

Example 94

(±)-1-(3-Bromo-carbazol-9-yl)-3-[4-(2-pyridin-ylmethyl)piperazin-1-yl]propan-2-ol The same method as employed in the preparation of Example 47 but starting from Example 9 and pyridine-2-carboxaldehyde using a parallel Radley synthesizer (0.21 mmol scale) and parallel flash purification (ISCO device) gives an oily compound. Slow addition of HCl (1M in Et$_2$O) into a solution of the above compound in MeOH gives the hydrochloride salt of the title compound as a pale beige solid in a 68% yield.

Mp: 240° C. (decomposition).
$^1$H NMR (DMSO-d$_6$+CD$_3$OD, 300 MHz) δ 8.71 (d, 1H, J=4.15 Hz), 8.38 (s, 1H), 8.22 (d, 1H, J=7.54 Hz), 8.69 (tr, 1H, J=7.54, 7.16 Hz), 7.74 (m, 3H), 7.63-7.54 (m, 2H), 7.47 (tr, 1H, J=7.54 Hz), 7.22 (tr, 1H, J=7.53, 7.16 Hz), 4.40 (br s, 3H), 4.12 (br s, 2H), 3.64-3.28 (m, 10H).

Example 95

(±)-1-(3-Bromo-carbazol-9-yl)-3-[4-(3-pyridin-ylmethyl)piperazin-1-yl]propan-2-ol The same method as employed in the preparation of Example 47 but starting from Example 9 and nicotinaldehyde using a parallel Radley synthesizer (0.21 mmol scale) and parallel flash purification (ISCO device) gives an oily compound. Slow addition of HCl (1M in Et$_2$O) into a solution of the above compound in MeOH gives the hydrochloride salt of the title compound as a white solid in a 73% yield.

Mp: 183° C. (decomposition).
$^1$H NMR (DMSO-d$_6$+CD$_3$OD, 300 MHz) δ 8.95 (s, 1H), 8.84 (d, 1H, J=4.9 Hz), 8.50 (d, 1H, J=7.91 Hz), 8.38 (d, 1H, J=1.13 Hz), 8.19 (d, 1H J=7.92 Hz), 7.90 (tr, 1H, J=6.79, 6.4 Hz), 7.70 (m, 2H), 7.57-7.44 (m, 2H), 7.20 (tr, 1H, J=7.53, 7.16 Hz), 4.41-4.29 (br s, 7H), 3.64-3.28 (m, 8H).

Example 96

(±)-1-(3-Bromocarbazol-9-yl)-3-[4-(4-pyridin-ylmethyl)piperazin-1-yl]propan-2-ol The same method as employed in the preparation of Example 47 but starting from Example 9 and isonicotinaldehyde using a parallel Radley synthesizer (0.21 mmol scale) and parallel flash purification (ISCO device) gives an oily compound. Slow addition of HCl (1M in Et$_2$O) into a solution of the above compound in MeOH gives the hydrochloride salt of the title compound as a pale beige solid in a 87% yield.

Mp: 170° C. (decomposition).
$^1$H NMR (DMSO-d$_6$+CD$_3$OD, 300 MHz) δ 8.87 (m, 2H), 8.39 (d, 1H, J=1.89 Hz), 8.21 (d, 1H, J=7.91 Hz), 7.99 (m, 2H), 7.39-7.53 (m, 3H), 7.47 (tr, 1H, J=7.53 Hz), 7.20 (tr, 1H, J=7.53, 7.16 Hz), 4.41-4.29 (br s, 7H), 3.64-3.28 (m, 8H).

Example 97

(±)-1-(3-Bromo-carbazol-9-yl)-3-[4-(quinolin-2-ylmethyl)piperazin-1-yl]propan-2-ol The same method as employed in the preparation of Example 47 but starting from Example 9 and quinoline-2-carboxaldehyde using a parallel Radley synthesizer (0.21 mmol scale) and parallel flash purification (ISCO device) gives an oily compound. Slow addition of HCl (1M in Et$_2$O) into a solution of the above compound in MeOH gives the hydrochloride salt of the title compound as an orange solid in a 67% yield.

Mp: 167° C. (decomposition).
$^1$H NMR (DMSO-d$_6$+CD$_3$OD, 300 MHz) δ 8.70-7.6 (m, 10H), 7.6-7.4 (m, 2H), 7.20 (tr, 1H, J=7.53, 7.16 Hz), 4.41-4.29 (br s, 5H), 3.64-3.28 (m, 10H).

Example 98

(±)-1-(3-Bromo-carbazol-9-yl)-3-[4-(2-furyl-4-bromomethyl)piperazin-1-yl]propan-2-ol The same method as employed in the preparation of Example 47 but starting from Example 9 and 4-bromo-2-furaldehyde using a parallel Radley synthesizer (0.21 mmol scale) and parallel flash purification (ISCO device) gives an oily compound. Slow addition of HCl (1M in Et$_2$O) into a solution of the above compound in MeOH gives the hydrochloride salt of the title compound as a beige solid in a 68% yield.

Mp: 245° C. (decomposition).
$^1$H NMR (DMSO-d$_6$+CD$_3$OD, 300 MHz) δ 8.38 (d, 1H, J=1.88 Hz), 8.19 (d, 1H, J=7.53 Hz), 8.03 (s, 1H), 7.69 (m, 2H), 7.55 (dd, 1H, J=8.8, 2.0 Hz), 7.47 (tr, 1H, J=7.15 Hz), 7.20 (tr, 1H, J=7.54, 7.16 Hz), 6.83 (s, 1H), 4.39 (br s, 2H), 4.09 (m, 6H), 3.62-3.10 (br m, 7H).

Example 99

(±)-1-(3-Bromocarbazol-9-yl)-3-[4-(1-naphtylmethyl)piperazin-1-yl]propan-2-ol

The same method as employed in the preparation of Example 47 but starting from Example 9 and 1-naphtaldehyde using a parallel Radley synthesizer (0.21 mmol scale) and parallel flash purification (ISCO device) gives an oily compound. Slow addition of HCl (1M in Et$_2$O) into a solution of the above compound in MeOH gives the hydrochloride salt of the title compound as a white solid in a 25% yield.

Mp: 185° C. (decomposition).
$^1$H NMR (DMSO-d$_6$, 300 MHz) δ 8.38 (m, 2H), 8.19 (d, 1H, J=7.54 Hz), 8.03 (br s, 2H), 7.8 7.44 (m, 8H), 7.20 (tr, 1H, J=7.54, 7.16 Hz), 4.39-3.0 (br m, 15H).

Example 100

(±)-1-{4-[(6-Bromo-1,3-benzodioxol-5-yl)methyl]piperazin-1-yl}-3-(3-bromo-carbazol-9-yl)propan-2-ol The same method as employed in the preparation of Example 47 but starting from Example 9 and 6-bromo-1,3-dioxole-5-carboxaldehyde using a parallel Radley synthesizer (0.21 mmol scale) and parallel flash purification (ISCO device) gives an oily compound. Slow addition of HCl (1M in Et$_2$O) into a solution of the above compound in MeOH gives the hydrochloride salt of the title compound as a white solid in a 58% yield.

Mp: 265° C. (decomposition).
$^1$H NMR (DMSO-d$_6$+CD$_3$OD 300 MHz) δ 8.38 (d, 1H, J=1.89 Hz), 8.20 (d, 1H, J=7.91 Hz), 7.70 (br tr, 2H), 7.56 (dd, 1H, J=8.8, 1.7 Hz), 7.49 (tr, 1H, J=7.54 Hz), 7.38 (br s, 1H), 7.30 (s, 1H), 7.20 (tr, 1H, J=7.54 Hz), 6.11 (s, 2H), 4.40 (br s, 3H), 4.09 (br s, 5H), 3.62-3.14 (m, 7H)

Example 101

(±)-1-{4-[(6-Chloro-1,3-benzodioxol-5-yl)methyl]piperazin-1-yl}-3-(3-bromo-carbazol-9-yl)propan-2-ol The same method as employed in the preparation of Example 47 but starting from Example 9 and 6-chloro-1,3-dioxole-5-carboxaldehyde using a parallel Radley synthesizer (0.21 mmol scale) and parallel flash purification (ISCO device) gives an oily compound. Slow addition of HCl (1M in Et$_2$O) into a solution of the above compound in MeOH gives the hydrochloride salt of the title compound as a white solid in a 82% yield.

Mp: 273° C. (decomposition).
$^1$H NMR (DMSO-d$_6$+CD$_3$OD, 300 MHz) δ 8.38 (d, 1H, J=1.89 Hz), 8.20 (d, 1H, J=7.91 Hz), 7.70 (br tr, 2H), 7.56 (dd, 1H, J=8.8, 1.7 Hz), 7.49 (tr, 1H, J=7.54 Hz), 7.38 (br s, 1H), 7.30 (s, 1H), 7.20 (br s, 2H), 6.11 (s, 2H), 4.40 (br s, 3H), 4.09 (br s, 5H), 3.62-3.14 (m, 7H)

Example 102

(±)-1-(3-Chlorocarbazol-9-yl)-3-[4-(4-fluorobenzyl)piperazin-1-yl]propan-2-ol

The same method as employed in the preparation of Example 73 but starting from Intermediate 17 and 1-(4-fluorobenzyl)piperazine gives the hydrochloride salt of the title compound as a white solid in a 27% yield.

Mp: 258.3° C. (decomposition).
$^1$H NMR (DMSO-d$_6$+D$_2$O, 300 MHz) δ 8.26 (d, 1H, J=1.88 Hz), 8.19 (d, 1H, J=7.54 Hz), 7.73-7.61 (m, 4H), 7.48-7.43 (m, 2H), 7.32-7.22 (m, 3H), 4.40 (br s, 2H), 4.13 (br s, 1H), 3.46-3.30 (m, 12H).

Example 103

(±)-1-(3-Chlorocarbazol-9-yl)-3-[4-(2-morpholin-4-ethyl)piperazin-1-yl]propan-2-ol The same method as employed in the preparation of Example 73 but starting from Intermediate 17 gives the hydrochloride salt of the title compound as a white solid in a 57% yield.

Mp: 250.7° C. (decomposition).
$^1$H NMR (DMSO-d$_6$+D$_2$O, 300 MHz) δ 8.26 (d, 1H, J=1.84 Hz), 8.20 (d, 1H, J=7.53 Hz), 7.72 (m, 2H), 7.50 (m, 2H), 7.23 (tr, 2H, J=7.53, 7.14 Hz), 4.42 (br s, 3H), 3.88 (br s, 4H), 3.75-2.80 (m, 18H).

Example 104

(±)-1-(3,6-Dibromocarbazol-9-yl)-3-[4-(3-piperidin-1-yl-propyl)piperazin-1-yl]propan-2-ol The same method as employed in the preparation of Example 1 but starting from 3,6-dibromo-9H-carbazole, Intermediate 18 and sodium hydride and heating at 60° C. for 16 hours gives after flash chromatography the title compound as a white foam. Slow addition of HCl (1M in Et$_2$O) into a solution of the above compound in DCM gives the hydrochloride salt of the title compound as a beige solid in a 53% yield.

Mp: 267° C. (decomposition).
$^1$H NMR (DMSO-d$_6$+D$_2$O, 300 MHz) δ 8.45 (d, 2H, J=1.9 Hz), 7.68 (d, 2H, J=8.8 Hz), 7.60 (dd, 2H, J=8.7, 1.9 Hz), 4.4-4.3 (m, 3H), 3.5-2.6 (m, 18H), 1.9 (m, 2H), 1.4 (m, 4H), 1.3 (m, 2H).

Example 105

(±)-1-(3-Chlorocarbazol-9-yl)-3-(4-cyclohexylpiperazin-1-yl)propan-2-ol

A solution of NaH (0.026 g, 0.60 mmol, 55% in mineral oil) is added into a solution of 3-chloro-9H-carbazole (0.100 g, 0.50 mmol) in anhydrous THF (5 mL). After 30 min of stirring at rt a solution of (±)-3-nitro-benzenesulfonic acid oxiranylmethyl ester in anhydrous THF (0.5 mL) is added. After 90 min of stirring at rt a solution of 1-cyclohexyl piperazine (0.25 g, 1.50 mmol) in anhydrous THF (1 mL) is then added. The resulting mixture is allowed to stir at 60° C. for 15 hours. The reaction mixture is quenched with brine (15 mL) and extracted with Et$_2$O (50 mL+2×25 mL). After drying over MgSO$_4$, evaporation under reduced pressure, the crude compound is purified via flash chromatography on a 3×24 cm$^2$ SiO$_2$ column using EtOAc/MeOH (8/1) and (4/1) as eluant. A solution of the purified above compound (0.088 g, 0.21 mmol, 41%) is treated with HCl (1M in Et$_2$O) to give the title compound hydrochloride (0.085 g, 0.17 mmol) as a white powder in a 34% yield.

Mp: 316° C. (decomposition).
$^1$H NMR (DMSO-d$_6$+MeOD-d$_4$ (35:1), 300 MHz) δ 8.25 (d, 1H, J=2.0 Hz), 8.19 (d, 1H, J=7.9 Hz), 7.74 (d, 1H, J=8.7 Hz), 7.72 (d, 1H, J=7.9 Hz), 7.48 (dd, 1H, J=7.9, 7.5 Hz), 7.45 (dd, 1H, J=8.7, 2.0 Hz), 7.22 (dd, 1H, J=7.9, 7.5 Hz), 4.42 (br s, 3H), 4.20-3.10 (m, 11H), 2.06 (br d, 2H, J=9.4 Hz), 1.81 (br d, 2H, J=12.1 Hz), 1.59 (br d, 1H, J=11.7 Hz), 1.50-1.00 (m, 5H).

Example 106

(±)-1-(3-Bromocarbazol-9-yl)-3-[4-(quinolin-4-ylmethyl)piperazin-1-yl]propan-2-ol The same method as employed in the preparation of Example 47 but starting from Example 9 and quinoline-4-carboxaldehyde using a parallel Radley synthesizer (0.21 mmol scale). Parallel flash purification (ISCO device) gives an oily compound. Slow addition of HCl (1M in Et$_2$O) into a solution of the above compound in MeOH gives the hydrochloride salt of the title compound as a pale yellow solid in a 73% yield.

Mp: 192° C. (decomposition).
$^1$H NMR (DMSO-d$_6$+CD$_3$OD, 300 MHz) δ 9.221 (d, 1H, J=5.28 Hz), 8.53 (d, 1H, J=8.29 Hz), 8.37 (br s, 2H), 8.19 (d, 1H, J=7.53 Hz), 8.07 (m, 2H), 7.89 (tr, 1H, J=7.54 Hz), 7.71 (tr, 2H, J=9.05, 8.66 Hz), 7.50 (d, 1H, J=8.67 Hz), 7.46 (tr, 1H, J=7.54 Hz), 7.24 (tr, 1H, J=7.54, 7.16 Hz), 4.99 (br s, 5H), 3.48-2.93 (m, 10H).

Analysis for C$_{29}$H$_{29}$BrN$_4$O. 2HCl. 2.1H$_2$O:
Calculated: C, 54.41; H, 5.54; N, 8.75;
Found: C, 54.45; H, 5.41; N, 8.64%:

Example 107

(±)-4-[3-(3-Chlorocarbazol-9-yl)-2-hydroxypropyl]-3,5-dimethylpiperazine-1-carboxylic tert-butyl ester The same method as employed in the preparation of Example 73 but starting from Intermediate 17 and 3,5-dimethylpiperazine-1-carboxylic tert-butyl ester gives after flash chromatography the title compound as a white solid in a 85% yield.

$^1$H NMR (CDCl$_3$, 300 MHz) δ 8.13-7.92 (m, 2H), 7.58-7.35 (m, 3H), 7.34-7.16 (m, 2H), 4.43-4.21 (m, 2H), 4.17-3.94 (1H, m), 3.9-3.6 (m, 1H), 3.51 (bs, 1H), 2.8-2.36 (m, 4H), 1.72-1.49 (m, 3H), 1.42 (s, 9H), 1.05-0.8 (m, 6H).

Example 108

(±)-1-[4-(cyclohexylmethyl)piperazin-1-yl]-3-(3,6-dichlorocarbazol-9-yl)acetone

At −78° C. a solution of oxalyl chloride (28 uL, 0.328 mmol) in anhydrous DCM (2 mL) is treated with anhydrous DMSO (43 uL, 0.613 mmol). After 15 min of stirring at −78° C., a solution of Example 76 (0.078 g, 0.164 mmol) in anhydrous DCM (0.5 mL) is added dropwise. The resulting mixture is allowed to stir for 40 min at −78° C. and TEA (125 μL) is added neat. After 10 min the reaction mixture is allowed to warm up to −30° C. After 1 hour of stirring at −30° C. the reaction mixture is quenched with water (15 mL). Extraction with DCM (3×25 mL), drying over MgSO$_4$ and evaporation under reduced pressure gives a yellow oil. Flash chromatography on a 3×25 cm$^2$ SiO$_2$ column using DCM/MeOH (100/5) mixture then (100/3) as eluting solvent gives the title compound as a pale yellow foam (0.045 g) in a 58% yield. Slow addition of HCl (1M in Et2O) is added to a solution of the above compound in DCM to give the hydrochloride salt of the title compound as a white powder.

Mp: 220° C. (decomposition).

$^1$H NMR (DMSO-d$_6$+MeOD-d$_4$ (35:1), 300 MHz) δ 8.34 (br. s, 2H), 7.60 (d, 2H, J=8.7 Hz), 7.48 (br. d, 2H, J=8.7 Hz), 5.55 (br. s, 2H), 4.31 (br. s, 2H), 3.60 (br. s, 2H), 3.32 (br. s, 6H), 2.96 (br. s, 2H), 1.90-1.53 (m, 6H), 1.31-1.07 (m, 3H), 1.03-0.84 (m, 2H).

Example 109

(±)-1-[4-(cyclohexylmethyl)piperazin-1-yl]-3-(3,6-dibromocarbazol-9-yl)acetone

The same method as employed in the preparation of Example 108 but starting from Example 45 gives the hydrochloride salt of the title compound as a white solid in a 64% yield.

Mp: 261° C. (decomposition).

Analysis for C$_{26}$H$_{31}$Br$_2$N$_3$O. 2HCl. 0.7H$_2$O:
Calculated: C, 48.27; H, 5.36; N, 6.50;
Found: C, 48.29; H, 5.50; N, 6.47%:

Example 110

(±)-1-(3,6-Dichlorocarbazol-9-yl)-3-[4-(2-morpholin-4-ethyl)piperazin-1-yl]propan-2-ol The same method as employed in the preparation of Example 73 but starting from (±)-3,6-dichloro-9-(oxiran-2-ylmethyl)-9H-carbazole gives the hydrochloride salt of the title compound as a white solid in a 30% yield.

Mp: 253° C. (decomposition).

Analysis for C$_{22}$H$_{32}$Cl$_2$N$_4$O$_2$. 3HCl. 0.3H$_2$O:
Calculated: C, 49.53; H, 5.92; N, 9.24;
Found: C, 49.56; H, 5.91; N, 9.19%:

Example 111

(±)-1-[4-(Cyclohexylmethyl)piperazin-1-yl]-3-(3-phenylcarbazol-9-yl)acetone

The same method as employed in the preparation of Example 108 but starting from Example 68 gives the hydrochloride salt of the title compound as a beige solid in a 76% yield.

Mp: 231° C. (decomposition).

Analysis for C$_{32}$H$_{37}$N$_3$O. 2HCl. 0.4H$_2$O:
Calculated: C, 68.66; H, 7.17; N, 7.51;
Found: C, 68.69; H, 7.01; N, 7.47%:

Example 112

(±)-1-(3-Bromocarbazol-9-yl)-3-[4-(2-morpholin-4-ethyl)piperazin-1-yl]propan-2-ol The same method as employed in the preparation of Example 105 but starting from 3-bromo-9H-carbazole and 4-(2-piperazin-1-ylethyl)morpholine gives the hydrochloride salt of the title compound as a white powder in a 38% yield.

Mp: 248° C. (decomposition).

$^1$H NMR (DMSO-d$_6$+MeOD-d$_4$ (35:1), 300 MHz) δ 8.39 (br s, 1H), 8.20 (d, 1H, J=7.5 Hz), 7.73 (d, 1H, J=8.7 Hz), 7.70 (d, 1H, J=7.9 Hz), 7.56 (br d, 1H, J=8.7 Hz), 7.48 (dd, 1H, J=7.9, 7.5 Hz), 7.22 (dd, 1H, J=7.5, 7.5 Hz), 4.42 (m, 3H), 3.88 (br s, 4H), 3.75-2.70 (m, 18H).

Example 113

(±)-1-(3-Chloro-carbazol-9-yl-)-3-(3,5-dimethylpiperazine-1-yl)propan-2-ol

The same method as employed in the preparation of Example 73 but starting from Intermediate 17 and 2,6-dimethylpiperazine gives the hydrochloride salt of the title compound as a beige solid in a 99% yield.

Mp: 65° C. (decomposition).

$^1$H NMR (CDCl$_3$, 300 MHz) δ 8.11-7.96 (m, 2H), 7.55-7.35 (m, 4H), 7.31-7.18 (m, 1H), 5.50 (br s, 2H), 4.34 (dd, 2H, J=4.90, 2.26 Hz), 4.25-4.14 (m, 1H), 2.97-2.69 (m, 3H), 2.67-2.53 (m, 1H), 2.47-2.33 (m, 2H), 1.87 (t, 1H, J=10.36 Hz), 1.55 (t, 1H, J=10.17 Hz), 0.99 (dd, 6H, J=5.84, 0.94 Hz)

Example 114

(±)-1-(3-Chlorocarbazol-9-yl-)-3-(2,6-dimethylpiperazin-1-yl)propan-2-ol

The same method as employed in the preparation of Example 3 but starting from Example 107 gives the title compound in a 84% yield as a beige powder.

Mp: 204° C. (decomposition).

$^1$H NMR (CDCl$_3$, 300 MHz) δ 8.10-7.99 (m, 2H), 7.55-7.35 (m, 4H), 7.30-7.20 (m, 1H), 5.37 (br s, 2H), 4.31 (dd, 2H, J=5.46, 2.07 Hz), 4.15-4.00 (m, 1H), 2.91-2.61 (m, 3H), 2.6-2.32 (m, 5H), 0.91 (dd, 6H, J=16.6, 5.65 Hz).

Example 115

(±)-1-(3,6-Dibromo-carbazol-9-yl-)-3-piperazin-1-ylpropan-2-amine

The same method as employed in the preparation of Example 3 but starting from (±)-4-[3-(3,6-dibromocarbazol- 9-yl)-2-aminopropyl]-piperazine-1-carboxylic tert-butyl ester gives the title compound in a 99% yield as a colorless oil. Slow addition of HCl (1M) into a solution of the above compound in DCM gives the title compound as a hydrochloride salt as beige powder.

Mp: 236° C. (decomposition).

$^1$H NMR (DMSO-$d_6$+MeOD-$d_4$ (35:1), 300 MHz) δ 8.45 (d, 2H, J=1.5 Hz), 7.71 (d, 2H, J=8.7 Hz), 7.59 (dd, 2H, J=8.7, 1.5 Hz), 4.59 (m, 2H), 3.75 (m, 1H), 2.91 (m, 4H), 2.80-2.45 (m, 6H).

(±)-4-[3-(3,6-Dibromocarbazol-9-yl)-2-aminopropyl]-piperazine-1-carboxylic tert-butyl ester is obtained from the treatment of a solution of Example 79 (0.05 g, 0.088 mmol) in anhydrous TMOF (1 mL) with ammonia (1.8 mL, 0.5M in 1,4-dioxane). The resulting mixture is stir at 60° C. for 3 hours then at 10° C. were added MeOH (2 mL) and NaBH$_4$ (0.12 g). After 15 hours of stirring at rt the reaction mixture is quenched with a saturated aqueous solution of sodium hydrogenocarbonate (15 mL), extracted with Et$_2$O (3×25 mL). After drying over MgSO$_4$ and evaporation under reduced pressure the crude compound is purified via flash chromatography on a 2×20 cm$^2$ SiO$_2$ column using EtOAc/MeOH/NH$_3$ (25% aqueous) (100/10/1.25) as eluant to give (±)-4-[3-(3,6-dibromocarbazol-9-yl)-2-aminopropyl]-piperazine-1-carboxylic tert-butyl ester (0.029 g, 0.051 mmol, 58% yield) as a yellow oil.

$^1$H NMR (CDCl$_3$, 300 MHz) δ 8.09 (d, 2H, J=1.9 Hz), 7.52 (dd, 2H, J=8.7, 1.9 Hz), 7.34 (d, 2H, J=8.7 Hz), 4.25 (dd, 1H, J=14.7, 4.5 Hz), 4.11 (dd, 1H, J=14.7, 7.9 Hz), 3.51 (m, 1H), 3.39 (m, 4H), 2.37 (m, 6H), 1.46 (br. s, 2H), 1.43 (s, 9H).

Example 116

(±)-N-Benzyl-N-[2-(3,6-dibromocarbazol-9-yl)-1-(piperazin-1-ylmethyl)ethyl]amine The same method as employed in the preparation of Example 3 but starting from (±)-4-[3-(3,6-dibromocarbazol-9-yl)-2-benzylaminopropyl]-piperazine-1-carboxylic tert-butyl ester gives the title compound in a 85% yield as a colorless oil. Slow addition of HCl (1M) into a solution of the above compound in DCM gives the title compound as a hydrochloride salt as a beige powder.

Mp.: 218° C. (decomposition).

$^1$H NMR (DMSO-$d_6$+D$_2$O, 300 MHz) δ 8.52 (d, 2H, J=1.5 Hz), 7.74 (d, 2H, J=8.7 Hz), 7.66 (dd, 2H, J=8.7, 1.5 Hz), 7.52 (m, 2H), 7.43 (m, 3H), 5.00 (dd, 1H, J=15.1, 4.9 Hz), 4.84 (dd, 1H, J=15.1, 8.9 Hz), 4.30 (br s, 2H), 3.79 (m, 1H), 3.02 (dd, 1H, J=13.6, 8.1 Hz), 2.72 (br s, 4H), 2.45-2.15 (m, 5H).

(±)-4-[3-(3,6-Dibromocarbazol-9-yl)-2-benzylaminopropyl]-piperazine-1-carboxylic tert-butyl ester is obtained from the treatment of a solution of Example 79 (0.05 g, 0.088 mmol) in anhydrous TMOF (1 mL) with benzylamine (0.100 mL) at 60° C. for 3 hours. MS monitoring showed formation of the imine intermediate. Then at rt were added MeOH (1 mL) and NaBH$_4$ (0.120 g). The resulting mixture is allowed to stir at rt for 16 hours. The reaction mixture is quenched with a saturated aqueous solution of sodium hydrogenocarbonate (15 mL). Extraction with Et$_2$O (3×25 mL), drying over MgSO$_4$, evaporation under reduced pressure and flash chromatography (SiO$_2$, 2×16 cm$^2$ column), Et$_2$O/MeOH (100/5)) as eluting solvent gives (±)-4-[3-(3,6-dibromocarbazol-9-yl)-2-benzylamino-propyl]-piperazine-1-carboxylic tert-butyl ester as a yellow oil in a 55% yield.

$^1$H NMR (CDCl$_3$, 300 MHz) δ 8.12 (d, 2H, J=1.8 Hz), 7.53 (dd, 2H, J=8.9, 1.8 Hz), 7.26 (m, 5H), 7.04 (m, 2H), 4.29 (dd, 1H, J=14.7, 6.2 Hz), 4.17 (dd, 1H, J=14.7, 6.1 Hz), 3.71 (d, 1H, J=13.6 Hz), 3.52 (d, 1H, J=13.6 Hz), 3.31 (m, 4H), 3.19 (m, 1H), 2.42 (dd, 1H, J=12.2, 9.2 Hz), 2.17 (m, 5H), 2.04 (br. s, 1H), 1.44 (s, 9H).

Example 117

(±)-1-(3,6-Dibromocarbazol-9-yl)-3-[4-(2-morpholin-4-yl-2-oxoethyl)piperazin-1-yl]propan-2-ol The same method as employed in the preparation of Example 73 but starting from Intermediate 15 and 4-(piperazin-1-ylacetyl)morpholine gives the hydrochloride salt of the title compound as a white powder (0.137 g, 0.21 mmol) in a 81% yield.

Mp: 255° C. (decomposition).

$^1$H NMR (DMSO-$d_6$+D$_2$O, 300 MHz) δ 8.41 (d, 2H, J=1.5 Hz), 7.63 (d, 2H, J=8.7 Hz), 7.58 (dd, 2H, J=8.7, 1.5 Hz), 4.33 (m, 3H), 4.02 (br. s, 2H), 3.76 (m, 8H), 3.55 (m, 4H), 3.44 (m, 2H), 3.34 (m, 4H).

Example 118

(±)-1-(3,6-Dibromocarbazol-9-yl)-3-{[4-(4,4-difluoro-1,3,5,7-tetramethyl-4-bora-3a,4a-diaza-s-indacene-8-yl)methyl]piperazin-1-yl}propan-2-ol A solution of Example 5 (0.040 g, 0.029 mmol) in DMF (1 mL) is treated with 8-bromo-methyl-4,4-difluoro-1,3,5,7-tetramethyl-4-bora-3a,4a-diaza-s-indacene (BODIPY 493/503 methyl bromide) (0.01 g, 1 equiv.) and DIEA (14.9 µL). The reaction mixture is kept in the dark and is allowed to stir at rt for 2 d. After evaporation of the solvent the crude compound is purified via flash chromatography using a 2×24 cm$^2$ column of SiO$_2$ and DCM/MeOH/NH$_3$ (25% aqueous) (90/1/0.1) as eluting solvent to give the title compound (Rf=0.24) as a red solid in a 95% yield.

FI-MS (APCI): m/z observed in a negative mode: 726.2.

HPLC (C8 Waters Symmetry Column, 4.6×50 mm$^2$, 254 nm, 2 mL/min, ACN/H$_2$O gradient with 0.1% TFA): retention time of 6.26 min.

Example 119

(±)-1-(3,6-Dibromocarbazol-9-yl)-3-[4-(N-(4,4-difluoro-5,7-dimethyl-4-bora-3a,4a-diaza-s-indacene-3-yl)methylacetamide)piperazin-1-yl]propan-2-ol The same method as employed in the preparation of Example 118 but starting from N-[(4,4-difluoro-5,7-dimethyl-4-bora-3a,4a-diaza-s-indacene-3-yl)methyl]iodoacetamide (BODIPY FL C$_1$-IA) gives the title compound (Rf=0.45, SiO$_2$, ACN/NH$_3$ (25% aqueous) (12/1)) as a red solid in a 84% yield.

FI-MS (APCI): m/z observed in a positive mode: 757.2

FI-MS (APCI): m/z observed in a negative mode: 755.0.

HPLC (C8 Waters Symmetry Column, 4.6×50 mm$^2$, 254 nm, 2 mL/min, ACN/H$_2$O gradient with 0.1% TFA): retention time of 5.47 min.

Example 120

(±)-1-(3,6-Dibromocarbazol-9-yl)-3-[4-(N-(4,4-difluoro-1,3,5,7-tetramethyl-4-bora-3a,4a-diaza-s-indacene-2-yl)acetamide)piperazin-1-yl]propan-2-ol The same method as employed in the preparation of Example 118 but starting from N-(4,4-difluoro-1,3,5,7-tetramethyl-4-bora-3a,4a-diaza-s-indacene-2-yl)iodoacetamide (BODIPY 507/545 IA) gives the title compound (Rf=0.32, SiO$_2$, DCM/MeOH/NH$_3$ (25% aqueous) (90/7/1)) as a red solid in a 68% yield.

FI-MS (Turbo Scan): m/z observed in a negative mode: 769.4.

HPLC (C8 Waters Symmetry Column, 4.6×50 mm$^2$, 254 nm, 2 mL/min, ACN/H$_2$O gradient with 0.1% TFA): retention time of 5.64 min.

Example 121

(±)-4-[({-[3-(3,6-Dibromocarbazol-9-yl)-2-hydroxypropyl]piperazin-1-yl}acetyl)amino]-2-(6-hydroxy-3-oxo-3H-xanthen-9-yl)benzoic acid The same method as employed in the preparation of Example 118 but starting from 2-(6-hydroxy-3-oxo-3H-xanthen-9-yl)-4-[(iodoacetyl)amino]benzoic acid gives after HPLC purification the title compound (Waters Nova-Pack HR C18 column, 25×100 mm$^2$, 6 uM, 60 Å, 30 mL/min, ACN/H$_2$O gradient with 0.1% TFA, 254 nm, retention time of 5.1 min) as an orange powder in a 90% yield.

M.p.: 107° C.
FI-MS (APCI): m/z observed in a negative mode: 853.2

Example 122

(±)-4-({-[3-(3,6-Dibromocarbazol-9-yl)-2-hydroxypropyl]piperazin-1-yl}methyl)-6,7-dimethoxy-2H-chromen-2-one The same method as employed in the preparation of Example 118 but starting from 4-(bromomethyl)-6,7-dimethoxy-2H-chromen-2-one gives after HPLC purification the title compound (Waters Nova-Pack HR C18 column, 25×100 mm$^2$, 6 μM, 60 Å, 30 mL/min, ACN/H$_2$O gradient with 0.1% TFA, 254 nm, retention time of 5.2 min) as a yellow powder in a 32% yield.

M.p.: 112° C.
FI-MS (APCI): m/z observed in a negative mode: 683.8.
FI-MS (APCI): m/z observed in a positive mode: 686.2.
Analysis for C$_{31}$H$_{33}$Br$_2$N$_3$O$_5$. 2(C$_2$F$_3$O$_2$):
Calculated: C, 46.02; H, 3.64; N, 4.60;
Found: C, 46.01; H, 3.69; N, 4.68%/:

Example 123

(±)-1-(3,6-Dibromocarbazol-9-yl)-3-{4-[3-(4,4-difluoro-1,3,5,7-tetramethyl-4-bora-3a,4a-diaza-s-indacene-8-yl)-propionyl]piperazin-1-yl}propan-2-ol A solution of Example 5 (0.017 g, 0.036 mmol) in DMF (1 mL) is treated with 4,4-difluoro-1,3,5,7-tetramethyl-4-bora-3a,4a-diaza-s-indacene-8-propionic acid, succinimidyl ester (BODIPY 493/503, SE) (0.015 g, 1 equiv.). The resulting solution is kept in the dark and allowed to stir at rt for 3 hours. After evaporation of the solvent the crude compound is purified via preparative HPLC (Waters Nova Pack HRC18, 6 μM, 25×100 mm$^2$, retention time of 5.9 min, using a H$_2$O/ACN/TFA (0.1%) gradient to give the title compound as a trifluoroacetate salt as an orange powder in a 95% yield.

M.p.: 160° C.
FI-MS (APCI): m/z observed in a positive mode: 770.2.
$^1$H NMR (DMSO-d$_6$, 300 MHz) δ 9.67 (br s, 1H), 8.49 (s, 2H), 7.72-7.54 (m, 4H), 6.24 (s, 2H), 6.04-5.84 (br s, 1H), 4.5-4.3 (m, 4H), 4.14-3.88 (m, 1H), 3.32-3.12 (m, 6H), 3.4-2.83 (m, 3H), 2.82-2.55 (m, 3H), 2.40 (s, 6H), 2.36 (s, 6H).

Example 124

(±)-1-[4-(4-Nitro-2,1,3-benzoxadiazol-7-yl)-piperazin-1-yl]-3-(3,6-dibromocarbazol-9-yl)-propan-2-ol A solution of Example 5 (0.060 g, 0.128 mmol) in DMSO (1 mL) is treated with 4-fluoro-7-nitro-benz-2-oxa-1,3-diazole (0.024 g, 1 equiv.). The resulting solution is kept in the dark and allowed to stir at rt for 2 hours. After evaporation of the solvent the crude compound is purified via preparative HPLC (Waters Nova Pack HRC18, 6 μM, 25×100 mm$^2$, retention time of 5.52 min, using a H$_2$O/ACWITA (0.1%) gradient to give the title compound as a trifluoroacetate salt as an orange powder in a 87% yield.

M.p.: 247° C.
FI-MS (Turbo Ion): m/z observed in a positive mode: 631.2.
FI-MS (Turbo Ion): m/z observed in a negative mode: 629.0.

Example 125

Preparation of a Pharmaceutical Formulation

The following formulation examples illustrate representative pharmaceutical compositions of this invention containing carbazole derivatives according to formula I. The present invention, however, is not limited to the following pharmaceutical compositions.

Formulation 1—Tablets

A compound of formula I is admixed as a dry powder with a dry gelatin binder in an approximate 1:2 weight ration. A minor amount of magnesium stearate is added as a lubricant. The mixture is formed into 240-270 mg tablets (80-90 mg of active piperazine derivatives of carbazole according to formula I per tablet) in a tablet press.

Formulation 2—Capsules

A compound of formula I is admixed as a dry powder with a starch diluent in an approximate 1:1 weight ratio. The mixture is filled into 250 mg capsules (125 mg of active piperazine derivatives of carbazole according to formula I per capsule).

Formulation 3—Liquid

A compound of formula I (1250 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

The compound of formula I is admixed as a dry powder with a dry gelatin binder in an approximate 1:2 weight ratio. A minor amount of magnesium stearate is added as a lubricant. The mixture is formed into 450-900 mg tablets (150-300 mg of active piperazine derivatives of carbazole according to formula I) in a tablet press.

Formulation 5—Injection

The compound of formula I is dissolved in a buffered sterile saline injectable aqueous medium to a concentration of approximately 5 mg/ml.

In the following the present invention shall be illustrated by means of some examples which are not construed to be viewed as limiting the scope of the invention.

Example 126

Biological Assays a) Production of Recombinant Bax

Human Bax-α lacking 20 amino acids at the COOH-terminus is expressed as a GST fusion protein or a His-tagged protein in *Escherichia coli*, and the protein is purified from the soluble cell fraction. In brief, the GST-Bax fusion protein is applied to a glutathione-Sepharose column, and Bax is released by cleavage with thrombin (0.6 U/mL). Bax is subsequently purified on heparin-Sepharose, followed by fast protein liquid chromatography (FPLC) Mono Q. His-tagged Bax is purified on a Ni-nitriloacetic acid-agarose column followed by FPLC MonoQ:

b) Isolation of Mitochondria

Mitochondria are isolated from mouse liver cells by differential centrifugation. Cells are broken with a dounce homogenizer and the suspension is centrifuged at 2,000 g in an Eppendorf centrifuge at 4° C. This procedure is repeated until almost all the cells are broken. Supernatants from each step are pooled before centrifugation at 13,000 g at 4° C. for 10 min. The pellet is resuspended in 40 mL MB buffer and centrifuged at 2000 g for 2 min. The supernatant is removed and centrifuged at 13 kg for 4 min. The mitochondria are recovered in the 13 k pellet and resuspended in MB buffer at a density of 30 OD600 nm/mL.

c) In Vitro Assay for Cytochrome c Release (Mitochondria Cytochrome c Release Triggered by Bax Activation)

Mitochondria (30 μg) from mouse liver are incubated with 200 nM recombinant Bax in the presence of various compounds (5 μM) in 200 μL of KCl buffer for 20 min at 30° C. and are then centrifuged for 4 min at 13,000 g at 4° C. Mitochondrial pellets corresponding to 1.5 μg proteins are separated by SDS-PAGE using 4-20% Tris-Gly gels (NOVEX) and their respective contents of cytochrome c are estimated by Western blotting using polyclonal anti-cytochrome c antibody (dilution 1:2,500). Antigen-antibody complexes are detected using horseradish peroxidase-conjugated goat anti-rabbit IgG and enhance chemiluminescence detection reagents. The cytochrome c bands are scanned and quantified using a Bio-Rad (GS-700 Imaging Densitometer).

d) Effect of Compounds according to formula I onto the Release of Cytochrome c Triggered by Bid-Induced Bax Activation (Mitochondria Cytochrome c Release Triggered by Bid-Induced Bax Activation)

Concerning the Bid-induced activation of Bax leading to mitochondrial Cytochrome C release, it is referred to the description of Martinou et al. in *The Journal of Cell Biology*, Vol. 144, No. 5, Mar. 8, 1999, pages 891-901. Mitochondria isolated from HeLa cells are incubated for 15 min at 30° C. in 100 μA of KCl buffer in the presence or absence of 10 nM recombinant Bid. The various compounds (10 μM) are pre-incubated for 5 min prior to addition of Bid. Following incubation, mitochondria were centrifuged for 5 min at 13000 g at 4° C. and the supernatant is collected for cytochrome c analysis. Cytochrome c is detected by Western blotting. The cytochrome c bands are scanned and quantified using a Bio-Rad (GS-700 Imaging Densitometer).

The above set out 2 in vitro assays c) and d) involving the determination of mitochondrial cytochrome c release are based on immunochemical methods using the Western blot analysis. Alternatively, said quantitative cytochrome c determinations could be performed by using spectrophotometric means:

I. by recording the difference between reduced and oxidised cytochrome c by dual wavelength double beam spectrophotometry;

by measuring the rather intensive γ or Soret peak in the spectrum of cytochrome c ($\epsilon$=100 mM$^{-1}$ cm$^{-1}$) is used for rapid and quantitative determination of the release of cytochrome c from isolated mitochondria. This technique allows a highly convenient, fast and reliable quantitative determination of the release of cytochrome c.

e) Sympathetic Neuron Culture and Survival Assay (Neuronal Survival)

Sympathetic neurons from superior cervical ganglia (SCG) of newborn rats (p4) are dissociated in dispase, plated at a density of 104 cells/cm$^2$ in 48 well MTT plates coated with rat tail collagen, and cultured in Leibowitz medium containing 5% rat serum, 0.75 g/ml NGF 7S (Boehringer Mannheim Corp., Indianapolis, Ind.) and arabinosine 105M. Cell death is induced at day 4 after plating by exposing the culture to medium containing 10 g/ml of anti NGF antibody (Boehringer Mannheim Corp., Indianapolis, Ind.) and no NGF or arabinosine, in the presence or absence of piperazine derivatives of carbazole inhibitors according to formula I. 24 hours after cell death induction, determination of cell viability is performed by incubation of the culture for 1 hour, at 37° C. in 0.5 mg/ml of 3-(4,5-dimethyl-thiazol-2-yl)2,5diphenyl tetrazolium bromide (MTT). After incubation in MTT, cells are re-suspended in DMSO, transferred to a 96 MTT plate and cell viability is evaluated by measuring optical density at 590 nm.

f) Biological Results—Discussion

The activities of the piperazine derivatives of carbazoles claimed in the formula I were assessed using the above described in vitro biological assays. Representative values are given in the table shown below:

| Compound | Mitochondria Cytochrome c Release Triggered by Bid-Induced Bax Activation (% Inhibition)[a] | Mitochondria Cytochrome c Release Triggered by Bax Activation (% Inhibition)[b] | Neuronal Survival[a] (%) |
| --- | --- | --- | --- |
| 23 | 68 | 51 | 45 |
| 27 | 88 | 40 | 40 |
| 32 | 98 | 43 | 30 |
| 45 | 37 | n.a.[c] | 60 |
| 60 | 60 | n.a.[c] | 40 |
| 62 | 99 | n.a.[c] | 30 |
| 73 | 74 | n.a.[c] | 30 |
| 80 | 73 | n.a.[c] | 20 |
| 110 | 87 | n.a.[c] | 30 |

[a] Compounds were tested at 10 μM
[b] Compounds were tested at 5 μM
[c] n.a. = not available The test compounds are among those described in the Examples 1-124 and their designation is derived therefrom. The above indicated values in column 2 and 3 refer to the inhibition (in %) of the mitochondrial cytochrome c release upon using the corresponding test compounds.

From the above table, it is derived that the test compounds according to the formula I do have a significant effect on the inhibition of release of cytochrome c. According to a preferred embodiment the tested compounds of formula I display an inhibition of the cytochrome c release of at least 40%, more preferred of at least 60% when tested at a concentration of between 2-50 μM, preferably between 5-20 μM and most preferred at 5-10 μM.

According to a preferred embodiment, the tested compounds display a neuronal survival rate of at least 30%, preferably of at least 40%.

The invention claimed is:
1. A compound according to formula I

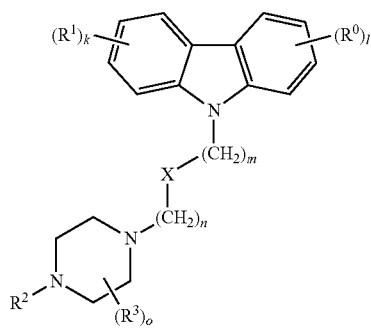

as well as a pharmaceutically acceptable salt thereof, in racemic form or in an enantiomeric excess, wherein $R^0$ and $R^1$ are selected independently from each other and are cyano, sulfonyl of the formula —$SO_2$—R where R is H, aryl, heteraryl, $C_1$-$C_6$ alkyl or $C_1$-$C_6$ alkyl substituted with a halogen, sulfoxy, substituted or unsubstituted $C_1$-$C_6$-thioalkoxy, nitro, primary, secondary or tertiary amine or sulfonamide, aminocarbonyl, amino-thiocarbonyl, hydroxy, substituted or unsubstituted $C_1$-$C_6$-alkoxy, aryloxy, heteroaryloxy, carboxylic amide, alkoxycarbonyl, carboxylic ester, carboxylic acid, substituted or unsubstituted $C_1$-$C_6$-alkyl carbonyl, substituted or unsubstituted arylcarbonyl or heteroarylcarbonyl, substituted or unsubstituted saturated or unsaturated $C_3$-$C_8$-cycloalkylcarbonyl, substituted or unsubstituted $C_1$-$C_6$-alkyl, substituted or unsubstituted $C_2$-$C_6$-alkenyl, substituted or unsubstituted $C_2$-$C_6$-alkynyl, substituted or unsubstituted aryl or heteroaryl, substituted or unsubstituted 3-8 membered saturated or unsaturated cyclic alkyl, a lipophilic substituent selected from the group consisting of bromine, aryl, and $C_1$-$C_6$-alkyl, or a fluorescent moiety selected from the group consisting of (4,4-difluoro-1,3,5,7-tetramethyl-4-bora-3a,4a-diaza-s-indacene-2-yl)acetamide, [(4,4-difluoro-5,7-dimethyl-4-bora-3a,4a-diaza-s-indacene-3-yl)methyl]acetamide, (4,4-difluoro-1,3,5,7-tetramethyl-4-bora-3a,4a-diaza-s-indacen-8-yl)methyl, 2-(6-hydroxy-3-oxo-3H-xanthen-9-yl)-4-(aminoacetyl)benzoic acid, (6,7-dimethoxy-2H-chromen-2-one)-4-methyl, 4,4-difluoro-1,3,5,7-tetramethyl-4-bora-3a,4a-diaza-s-indacene-8-propionyl, and 4-nitro-(2,1,3-benzoxadiazol)-7-yl;

$R^2$ is $C_1$-$C_6$-alkylaryl, $C_1$-$C_6$-alkylheteroaryl, an aryl, or a 5-6-membered heterocyclic group containing at least one of oxygen, nitrogen and sulfur, wherein the aryl and heterocyclic group are substituted by at least one C(=O)ORa, trifluoromethyl, trifluoromethoxy, ORa, OC(=O)Ra, OC(=O)Rc, NRaRb, CH$_2$—NRaRb, NO$_2$, cyano, halogen, SO$_2$NRaRb, SO$_2$NRaRc, NRaSO$_2$Ra, NRaSO$_2$Rc, $C_1$-$C_6$-alkyleneC(=O)ORa, and OSO$_2$-trifluoromethyl, or $R^2$ is $C_1$-$C_6$-alkylaryl or $C_1$-$C_6$-alkylheteroaryl containing at least one heteroatom selected from oxygen, nitrogen and sulfur, wherein said $C_1$-$C_6$-alkylaryl or $C_1$-$C_6$-alkylheteroaryl is substituted by at least one C(=O)ORa, trifluoromethyl, trifluoromethoxy, ORa, ORc, SRa, SRc, OC(=O) Ra, OC(=O) Rc, NRaRb, CH$_2$—NRaRb, NO$_2$, cyano, halogen, SO$_2$NRaRb, SO$_2$NRaRc, NRaSO$_2$Ra, NRaSO$_2$Rc, $C_1$-$C_6$-alkyleneC(=O)ORa or OSO$_2$-trifluoromethyl;

Ra and Rb, in $R^2$, are independently hydrogen or $C_1$-$C_6$-alkyl, optionally substituted by at least one halogen, a $C_1$-$C_6$-alkoxy or an amino group and Rc, in $R^2$, is an unsubstituted or substituted phenyl, an unsubstituted or substituted benzyl or a 3-8-membered unsubstituted or substituted saturated 3-8-membered cyclic alkyl;

$R^3$ is hydrogen, halogen, substituted or unsubstituted $C_1$-$C_6$-alkyl, substituted or unsubstituted $C_2$-$C_6$-alkenyl, substituted or unsubstituted $C_2$-$C_6$-alkynyl, substituted or unsubstituted aryl or hetero-aryl, substituted or unsubstituted 3-8 membered saturated and unsaturated cyclic alkyl, alkoxycarbonyl, carboxylic amide, $C_1$-$C_6$-alkoxy, substituted or unsubstituted aryloxy, substituted or unsubstituted hetero-aryloxy, hydroxy, substituted or unsubstituted $C_1$-$C_6$-alkyl carbonyl, substituted or unsubstituted arylcarbonyl or heteroarylcarbonyl, substituted or unsubstituted saturated or unsaturated $C_4$-$C_8$-cycloalkylcarbonyl, or an oxo (=O) group;

k and l are 1;

X is a group of the formula —(CR'R")—, wherein R' and R" are hydrogen, hydroxyl or a substituted or unsubstituted $C_1$-$C_6$ alkoxy, whereby at least one of R' and/or R" is not hydrogen but hydroxyl or a substituted or unsubstituted $C_1$-$C_6$-alkoxy;

m and n are independently from each other an integer from 1 to 3 and o is an integer from 0 to 8.

2. The compound according to claim 1, wherein $R^0$ and $R^1$ of formula I are selected independently from each other and are cyano, substituted or unsubstituted and $C_1$-$C_6$-alkyl, substituted or unsubstituted 3-8 membered saturated or unsaturated cyclic alkyl, C(=O)ORa, C(=O)NRaRb, C(=O)NRaRc, C(=O)Ra, C(=O)Rc, CRa(=N—N-Rb), CRa(=N—N-Rc), CRa(=N—O-Rb), trifluoromethyl, trifluoromethoxy, ORa, ORc, NRaRb, NRaRc, NRaC(=O)NRaRb, NRaC(=O)NRaRc, NRaC(=O)Rb, NRaC(=O)Rc, OC(=O)Ra, OC(=O)Rc, NRa(SO$_2$Rb), NRa(SO$_2$Rc), SO$_2$NRaRb, SO$_2$NRaRc, NO$_2$, CH$_2$NRaRb, CH$_2$NRaRc, CH$_2$NRaC(=O)NRaRb, SRa, SRc, CH$_2$NRaC(=O)NRaRc, CH$_2$NRaC(=O)Rb, CH$_2$NRaC(=O)Rc, CH$_2$NRa(SO$_2$Rb), CH$_2$NRa(SO$_2$Rc), OSO$_2$-trifluoromethyl; or aryl or a 5-6-membered heteroaryl or heterocyclic group wherein at least one heteroatom in the 5-6 membered heteroaryl or heterocyclic group is oxygen, nitrogen or sulfur, said aryl or heteroaryl or heterocyclic group being optionally substituted by at least one $C_1$-$C_6$-alkyl, C(=O)ORa, trifluoromethyl, trifluoromethoxy, ORa, ORc, SRa, SRc, OC(=O)Ra, OC(=O)Rc, NRaRb, CH$_2$—NRaRb, NO$_2$, cyano, halogen, SO$_2$NRaRb, SO$_2$NRaRc, NRaSO$_2$Ra, NRaSO$_2$Rc, $C_1$-$C_6$-alkyleneC(=O)ORa, OSO$_2$-trifluoromethyl;

with Ra and Rb, in $R^1$, $R^0$ or both, being the same or different, independently selected from hydrogen and $C_1$-$C_6$-alkyl, being optionally substituted by at least one halogen, $C_1$-$C_6$-alkoxy or amino group; and Rc, in $R^1$, $R^0$ or both, is an unsubstituted or substituted phenyl, an unsubstituted or substituted benzyl, a 3-8-membered unsubstituted or substituted saturated 3-8-membered cyclic alkyl, a lipophilic substituents selected from the group consisting of bromine, aryl, and $C_1$-$C_6$-alkyl, or a fluorescent moiety selected from the group consisting of (4,4-difluoro-1,3,5,7-tetramethyl-4-bora-3a,4a-diaza-s-indacene-2-yl)acetamide, [(4,4-difluoro-5,7-dimethyl-4-bora-3a,4a-diaza-s-indacene-3-yl)methyl]acetamide, (4,4-difluoro-1,3,5,7-tetramethyl-4-bora-3a,4a-diaza-s-indacen-8-yl)methyl, 2-(6-hydroxy-3-oxo-3H-xanthen-9-yl)-4-(aminoacetyl)benzoic acid, (6,7-dimethoxy-2H-chromen-2-one)-4-methyl, 4,4-difluoro-1,3,5,7-tetramethyl-4-bora-3a,4a-diaza-s-indacene-8-propionyl, and 4-nitro-(2,1,3-benzoxadiazol)-7-yl.

3. The compound according to claim 1, wherein $R^2$ of formula I is $C_1$-$C_6$-alkylaryl, $C_1$-$C_6$-alkylheteroaryl, or an aryl, wherein the aryl group is substituted by at least one of C(=O)ORa, trifluoromethyl, trifluoromethoxy, ORa, OC(=O)Ra, OC(=O)Rc, NRaRb, $CH_2$—NRaRb, $NO_2$, cyano, halogen, $SO_2$NRaRb, $SO_2$NRaRc, NRa$SO_2$Ra, NRa$SO_2$Rc, $C_1$-$C_6$-alkyleneC(=O)ORa, and O$SO_2$trifluoromethyl;

Ra and Rb, in $R^2$, are independently hydrogen or $C_1$-$C_6$-alkyl, optionally substituted by at least one halogen, a $C_1$-$C_6$-alkoxy or an amino group and Rc, in $R^2$, is an unsubstituted or substituted phenyl, an unsubstituted or substituted benzyl or a 3-8-membered unsubstituted or substituted saturated 3-8-membered cyclic alkyl.

4. The compound according to claim 1, wherein $R^3$ of formula I is hydrogen, $C_1$-$C_6$-alkyl, ORa, ORc, C(=O)ORa, C(=O)ORc C(=O)NRaRb, C(=O)NRaRc, C(=O)Ra, C(=O)Rc, RaC(=O)NRaRc, RaC(=O)Rb, RaC(=O)Rc, Ra($SO_2$Rb), Ra($SO_2$Rc), (=O); or $R^3$ of formula I is an aryl or a 5-6-membered heterocyclic group wherein at least one heteroatom in the 5-6 membered heterocyclic group is selected from the group consisting of oxygen, nitrogen and sulfur, both the aryl, heterocyclic group being optionally substituted by at least one $C_1$-$C_6$-alkyl, C(=O)ORa, C(=O)ORc, trifluoromethyl, trifluoromethoxy, ORa, OC(=O)Ra, OC(=O)Rc, NRaRb, $CH_2$—NRaRb, $NO_2$, cyano, halogen, $SO_2$NRaRb, $SO_2$NRaRc, NRa$SO_2$Ra, NRa$SO_2$Rc, $C_1$-$C_6$-alkyleneC(=O)ORa, O$SO_2$trifluoromethyl;

whereby Ra and Rb are the same or different and they are independently selected from hydrogen and $C_1$-$C_6$-alkyl, being optionally substituted by at least one halogen, a $C_1$-$C_6$-alkoxy or an amino group; and whereby, Rc does represent therein an unsubstituted or substituted phenyl, an unsubstituted or substituted benzyl or a 3-8-membered unsubstituted or substituted saturated 3-8-membered cyclic alkyl.

5. The compound according to claim 1, wherein $R^0$ and $R^1$ represent a lipophilic substitutent selected from the group consisting of bromine, aryl, and $C_1$-$C_6$-alkyl.

6. The compound according to claim 1, wherein $R^3$ is hydrogen or $C_1$-$C_6$-alkyl.

7. The compound according to claim 1, wherein $R^2$ is (4,4-difluoro-1,3,5,7-tetramethyl-4-bora-3a,4a-diaza-s-indacene-2-yl)acetamide, [(4,4-difluoro-5,7-dimethyl-4-bora-3a,4a-diaza-s-indacene-3-yl)methyl]acetamide, (4,4-difluoro-1,3,5,7-tetramethyl-4-bora-3a,4a-diaza-s-indacen-8-yl)methyl, 2-(6-hydroxy-3-oxo-3H-xanthen-9-yl)-4-(aminoacetyl)benzoic acid, (6,7-dimethoxy-2H-chromen-2-one)-4-methyl, 4,4-difluoro-1,3,5,7-tetramethyl-4-bora-3a,4a-diaza-s-indacene-8-propionyl, or 4-nitro-(2,1,3-benzoxadiazol)-7-yl.

8. The compound according to claim 1, which is in an enantiomeric excess of at least 52% ee.

9. The compound according to claim 1 selected from the following group:

(±)-1-[(4-Fluorophenyl)-piperazin-1-yl]-3-(3,6-dibromocarbazol-9-yl)-propan-2-ol;

(±)-1-(3,6-Dibromocarbazol-9-yl)-3-[4-(thien-3-ylmethyl)piperazin-1-yl]propan-2-ol;

(±)-1-(3,6-Dibromo carbazol-9-yl)-3-[4-(4-methoxybenzyl)piperazin-1-yl]propan-2-ol;

(±)-1-(3,6-Dibromocarbazol-9-yl)-3-[4-(4-tert-butylbenzyl)piperazin-1-yl]propan-2-ol;

(±)-4-[3-(3,6-Dibromocarbazol-9-yl)-2-hydroxypropyl]-N-(4-fluorophenyl)piperazine-1-carboxamide;

(±)-1-(3,6-Dibromo-carbazol-9-yl)-3-[4-(3,4-dichlorobenzyl)piperazin-1-yl]propan-2-ol;

(±)-1-(3,6-Dibromo-carbazol-9-yl)-3-[4-(2-morpholin-4-ethyl)piperazin-1-yl]propan-2-ol;

(±)-1-(3,6-Dibromocarbazol-9-yl)-3-[4-(3-piperidin-1-ylpropyl)piperazin-1-yl]propan-2-ol;

(±)-1-(3,6-dibromo-carbazol-9-yl)-3-[4-(4-fluoro-benzyl)-piperazin-1yl]-propan-2-ol;

(±)-1-(3,6-dibromo-carbazol-9-yl)-3-[4-(3-phenyl-propyl)-piperazin-1-yl]-propan-2-ol;

(±)-1-(3,6-dibromo-carbazol-9-yl)-3-[4-(thien-2-ylmethyl)piperazin-1-yl]propan-2-ol;

(±)-1-(3,6-dibromocarbozyl-9-yl)-3-[4-(pyridine-3-ylmethyl)piperazin-1-yl]propan-2-ol;

(±)-1-(3,6-dibromcarbazol-9-yl)-3-[4-trifluoromethylbenzyl]piperazin-1-yl]propan-2-ol; and (±)-1-(3,6-Dibromocarbazol-9-yl)-3-{[4-(4,4-difluoro-1,3,5,7-tetramethyl-4-bora-3a,4a-diaza-s-indacene-8-yl)methyl]piperazin-1-yl}propan-2-ol.

10. A pharmaceutical composition comprising at least one compound according to claim 1 and a pharmaceutically acceptable carrier, diluent or excipient thereof.

11. The compound according to claim 1, which is in an enantiomeric excess of at least 92-98% ee.

12. A pharmaceutical composition comprising at least one compound according to claim 2 and a pharmaceutically acceptable carrier, diluent or excipient thereof.

13. A pharmaceutical composition comprising at least one compound according to claim 3 and a pharmaceutically acceptable carrier, diluent or excipient thereof.

14. A pharmaceutical composition comprising at least one compound according to claim 4 and a pharmaceutically acceptable carrier, diluent or excipient thereof.

15. A pharmaceutical composition comprising at least one compound according to claim 5 and a pharmaceutically acceptable carrier, diluent or excipient thereof.

16. A pharmaceutical composition comprising at least one compound according to claim 6 and a pharmaceutically acceptable carrier, diluent or excipient thereof.

17. A pharmaceutical composition comprising at least one compound according to claim 7 and a pharmaceutically acceptable carrier, diluent or excipient thereof.

18. A pharmaceutical composition comprising at least one compound according to claim 8 and a pharmaceutically acceptable carrier, diluent or excipient thereof.

19. A pharmaceutical composition comprising at least one compound according to claim 9 and a pharmaceutically acceptable carrier, diluent or excipient thereof.

20. A pharmaceutical composition comprising at least one compound according to claim 11 and a pharmaceutically acceptable carrier, diluent or excipient thereof.

* * * * *